US010932933B2

(12) United States Patent
Bardsley et al.

(10) Patent No.: US 10,932,933 B2
(45) Date of Patent: Mar. 2, 2021

(54) IMPLANT DELIVERY SYSTEMS AND METHODS

(71) Applicant: SHANGHAI WALLABY MEDICAL TECHNOLOGIES CO., INC., Shanghai (CN)

(72) Inventors: Earl Bardsley, San Clemente, CA (US); Dean Schaefer, Irvine, CA (US); Jerome Choe, Irvine, CA (US); Tan Dinh, Santa Ana, CA (US); Luis Cardenas, Moreno Valley, CA (US); Mindy Feng, Irvine, CA (US); Cheng Ian, Irvine, CA (US); Paul Dao, Fountain Valley, CA (US); Jonathan Polansky, Beverly, MA (US); J Christopher Flaherty, Auburndale, FL (US); Paul Ehlinger, Huntington Beach, CA (US)

(73) Assignee: SHANGHAI WALLABY MEDICAL TECHNOLOGIES CO., INC., Shanghai (CN)

( * ) Notice: Subject to any disclaimer, the term of this patent is extended or adjusted under 35 U.S.C. 154(b) by 51 days.

(21) Appl. No.: 16/321,440

(22) PCT Filed: May 28, 2017

(86) PCT No.: PCT/US2017/034895
§ 371 (c)(1),
(2) Date: Jan. 28, 2019

(87) PCT Pub. No.: WO2018/022186
PCT Pub. Date: Feb. 1, 2018

(65) Prior Publication Data
US 2020/0229957 A1 Jul. 23, 2020

Related U.S. Application Data

(60) Provisional application No. 62/435,381, filed on Dec. 16, 2016, provisional application No. 62/368,927, filed on Jul. 29, 2016.

(51) Int. Cl.
A61F 2/966 (2013.01)
A61B 17/12 (2006.01)

(52) U.S. Cl.
CPC .... A61F 2/966 (2013.01); A61B 2017/12054 (2013.01); A61F 2002/9665 (2013.01)

(58) Field of Classification Search
CPC ............... A61B 2017/12054; A61B 17/12113
See application file for complete search history.

(56) References Cited

U.S. PATENT DOCUMENTS 5,217,484 A 6/1993 Marks
5,250,071 A * 10/1993 Palermo ............. G02B 26/0825
606/198

(Continued)

FOREIGN PATENT DOCUMENTS

EP 1582152 B1 10/2005
EP 2190359 B1 6/2010

(Continued)

Primary Examiner — Richard G Louis
(74) Attorney, Agent, or Firm — Helen S Liu

(57) ABSTRACT

The present teachings provide a medical system for delivering and deploying a medical implant, and the method of using thereof. Specifically, one aspect of the present teachings provides a medical system having an implant with an engagement loop, and a delivery system having an engagement wire and an interface. During implant delivery, the engagement wire engages the engagement loop of the implant. The engagement wire further interacts with the interface in order to prevent unintended disengagement of the engagement loop from the engagement wire. Certain embodiment of the present teaching also includes an implant release control mechanism fixedly attaching to a proximal end of the engagement wire. During implant delivery, the implant release control mechanism attaches the proximal end of the delivery system. During implant deployment, the (Continued)

implant release control mechanism detaches the proximal end of the delivery system.

14 Claims, 55 Drawing Sheets

(56) References Cited

U.S. PATENT DOCUMENTS

| | | |
|---|---|---|
| 5,312,415 A | 5/1994 | Palermo |
| 5,582,619 A | 12/1996 | Ken |
| 5,833,705 A | 11/1998 | Ken et al. |
| 5,853,418 A | 12/1998 | Ken et al. |
| 6,013,084 A | 1/2000 | Ken et al. |
| 6,193,728 B1 | 2/2001 | Ken et al. |
| 6,936,058 B2 | 8/2005 | Forde et al. |
| 7,166,122 B2 | 1/2007 | Aganon et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,422,569 B2 | 9/2008 | Wilson et al. |
| 7,485,122 B2 | 2/2009 | Teoh |
| 7,572,246 B2 | 8/2009 | Wilson et al. |
| 7,608,058 B2 | 10/2009 | Wilson et al. |
| 7,695,484 B2 | 4/2010 | Wallace et al. |
| 7,708,754 B2 | 5/2010 | Balgobin et al. |
| 7,708,755 B2 | 5/2010 | Davis, III et al. |
| 7,766,933 B2 | 8/2010 | Davis, III et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,883,526 B2 | 2/2011 | Jones et al. |
| 7,901,444 B2 | 3/2011 | Slazas |
| 7,927,348 B2 | 4/2011 | Jones et al. |
| 7,938,845 B2 | 5/2011 | Aganon et al. |
| 7,985,238 B2 | 7/2011 | Balgobin et al. |
| 8,029,464 B2 | 10/2011 | Wilson et al. |
| 8,029,465 B2 | 10/2011 | Wilson et al. |
| 8,029,466 B2 | 10/2011 | Wilson et al. |
| 8,029,467 B2 | 10/2011 | Wilson et al. |
| 8,157,852 B2 | 4/2012 | Bloom et al. |
| 8,162,971 B2 | 4/2012 | Wilson et al. |
| 8,167,838 B2 | 5/2012 | Wilson et al. |
| 8,167,839 B2 | 5/2012 | Wilson et al. |
| 8,172,862 B2 | 5/2012 | Wallace et al. |
| 8,177,746 B2 | 5/2012 | Wilson et al. |
| 8,211,141 B2 | 7/2012 | Davis, III et al. |
| 8,366,665 B2 | 2/2013 | Wilson et al. |
| 8,376,995 B2 | 2/2013 | Wilson et al. |
| 8,376,996 B2 | 2/2013 | Wilson et al. |
| 8,409,139 B2 | 4/2013 | Wilson et al. |
| 8,425,461 B2 | 4/2013 | Wilson et al. |
| 8,439,871 B2 | 5/2013 | Wilson et al. |
| 8,523,811 B2 | 9/2013 | Wilson et al. |
| 8,535,345 B2 | 9/2013 | Desai et al. |
| 8,540,671 B2 | 9/2013 | Wilson et al. |
| 8,608,772 B2 | 12/2013 | Wilson et al. |
| 8,821,441 B2 | 9/2014 | Wilson et al. |
| 8,888,806 B2 | 11/2014 | Desai et al. |
| 8,926,650 B2 | 1/2015 | Que et al. |
| 9,089,333 B2 | 7/2015 | Wilson et al. |
| 9,101,361 B2 | 8/2015 | Wilson et al. |
| 9,204,882 B2 | 12/2015 | Wilson et al. |
| 9,307,999 B2 | 4/2016 | Li et al. |
| 9,339,275 B2 | 5/2016 | Trommeter et al. |
| 9,358,021 B2 | 6/2016 | Losordo et al. |
| 9,375,333 B1 | 6/2016 | Aboytes et al. |
| 9,439,661 B2 | 9/2016 | Johnson et al. |
| 9,480,479 B2 | 11/2016 | Chen et al. |
| 9,486,223 B2 | 11/2016 | Que et al. |
| 9,918,718 B2 | 3/2018 | Lorenzo |
| 10,045,765 B2 | 8/2018 | Rafiee et al. |
| 10,052,108 B2 | 8/2018 | Aguilar et al. |
| 10,098,657 B2 | 10/2018 | Losordo et al. |
| 10,111,682 B2 | 10/2018 | Johnson et al. |
| 10,182,822 B2 | 1/2019 | Freudenthal |
| 10,206,685 B2 | 2/2019 | Trommeter et al. |
| 2003/0032757 A1 | 2/2003 | Lin |
| 2003/0172436 A1 | 9/2003 | Thompson |
| 2003/0211493 A1 | 11/2003 | Baughn et al. |
| 2004/0002732 A1 | 1/2004 | Teoh et al. |
| 2004/0006354 A1 | 1/2004 | Schaefer et al. |
| 2004/0006363 A1 | 1/2004 | Schaefer |
| 2005/0043755 A1* | 2/2005 | Wilson ............ A61B 17/32056 606/200 |
| 2006/0050884 A1 | 3/2006 | O'Brien |
| 2006/0116708 A1 | 6/2006 | Ogawa et al. |
| 2006/0116714 A1 | 6/2006 | Sepetka et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276830 A1 | 12/2006 | Balgobin et al. |
| 2006/0276833 A1 | 12/2006 | Balgobin et al. |
| 2007/0239193 A1 | 10/2007 | Simon et al. |
| 2008/0097462 A1 | 4/2008 | Mitelberg et al. |
| 2008/0306503 A1 | 12/2008 | Que et al. |
| 2010/0137898 A1 | 6/2010 | Teoh |
| 2011/0092997 A1 | 4/2011 | Kang |
| 2011/0213406 A1 | 9/2011 | Aganon et al. |
| 2012/0041472 A1* | 2/2012 | Tan ................. A61B 17/12113 606/200 |
| 2012/0116441 A1 | 5/2012 | Yamanaka et al. |
| 2012/0179194 A1 | 7/2012 | Wilson et al. |
| 2012/0197289 A1 | 8/2012 | Wilson et al. |
| 2012/0253381 A1 | 10/2012 | Forsythe et al. |
| 2013/0138141 A1 | 5/2013 | Wilson et al. |
| 2013/0138142 A1 | 5/2013 | Wilson et al. |
| 2013/0325054 A1 | 12/2013 | Watson |
| 2014/0277341 A1 | 9/2014 | Havel et al. |
| 2014/0330299 A1 | 11/2014 | Rosenbluth et al. |
| 2016/0228124 A1 | 8/2016 | Trommeter et al. |
| 2017/0245865 A1 | 8/2017 | Jones et al. |
| 2018/0161038 A1 | 6/2018 | Lorenzo |
| 2018/0228494 A1 | 8/2018 | Walzman |
| 2018/0303486 A1 | 10/2018 | Rosenbluth et al. |
| 2018/0317924 A1 | 11/2018 | Aguilar et al. |
| 2019/0021755 A1 | 1/2019 | Johnson et al. |

FOREIGN PATENT DOCUMENTS

| | | |
|---|---|---|
| EP | 2422716 A1 | 2/2012 |
| EP | 2674114 A1 | 12/2012 |
| EP | 2668914 A1 | 12/2013 |
| WO | WO200754118 A1 | 5/2007 |
| WO | WO201853314 A1 | 4/2010 |
| WO | WO201548821 A1 | 1/2015 |
| WO | WO201851187 A1 | 3/2018 |
| WO | WO2018210907 A1 | 11/2018 |

* cited by examiner

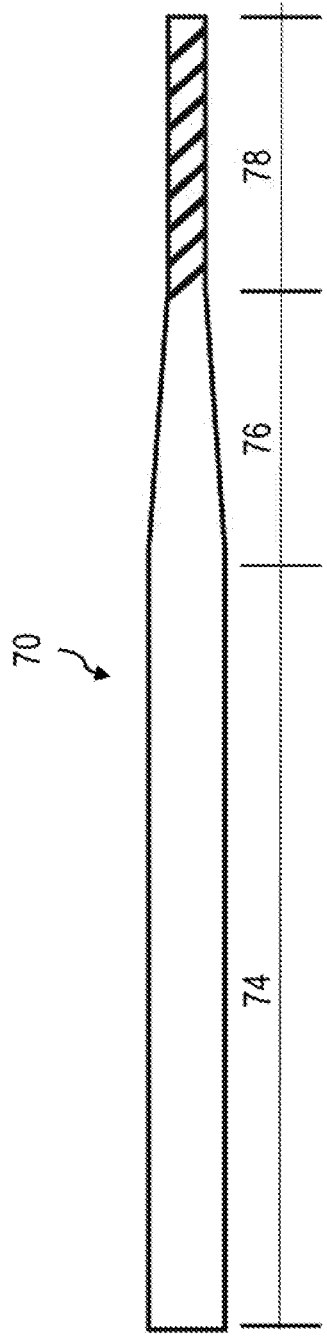
FIG. 2B
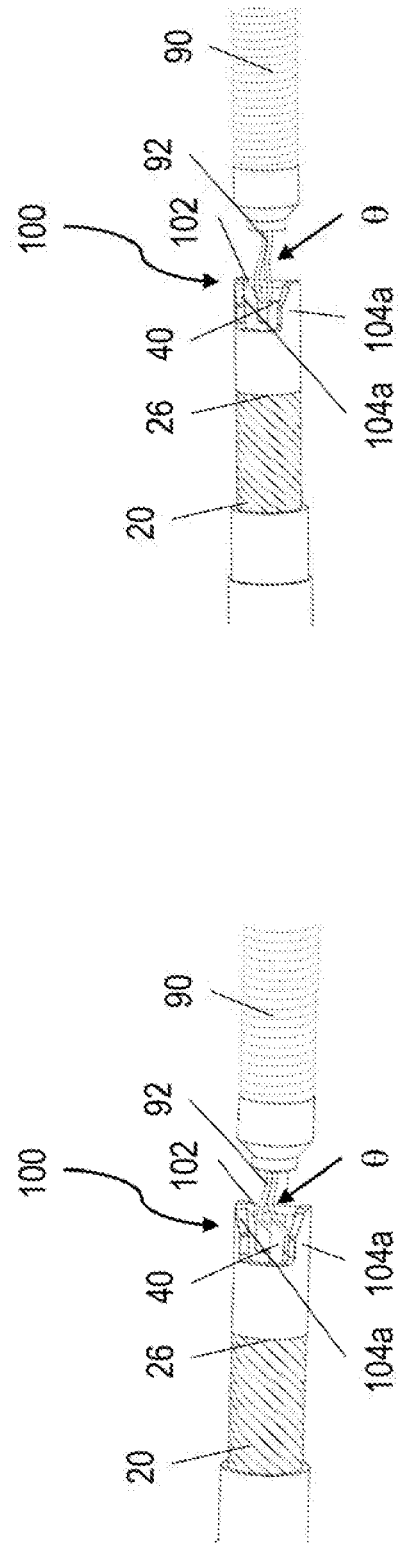
FIG. 4A
FIG. 4B

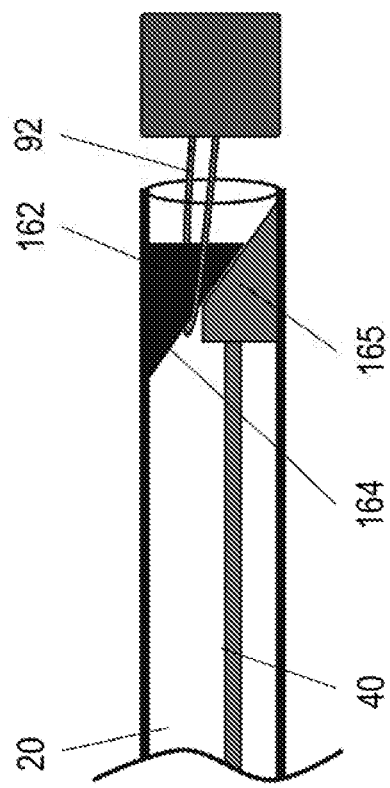
FIG. 9
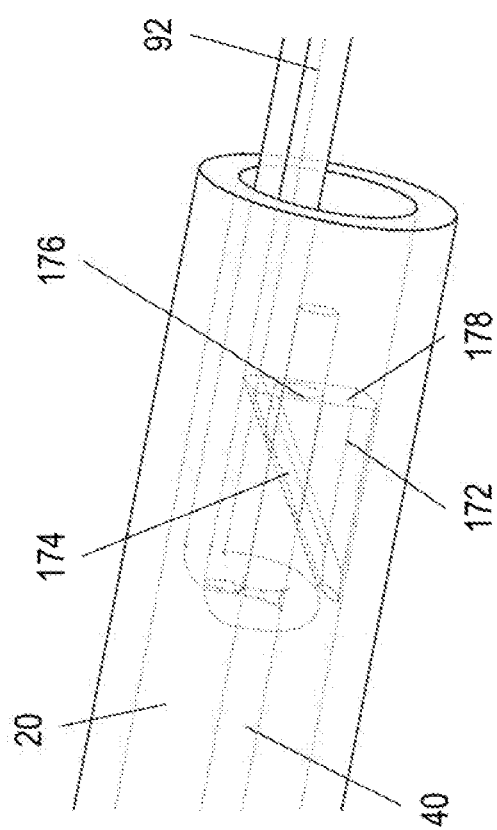
FIG. 10
FIG. 11
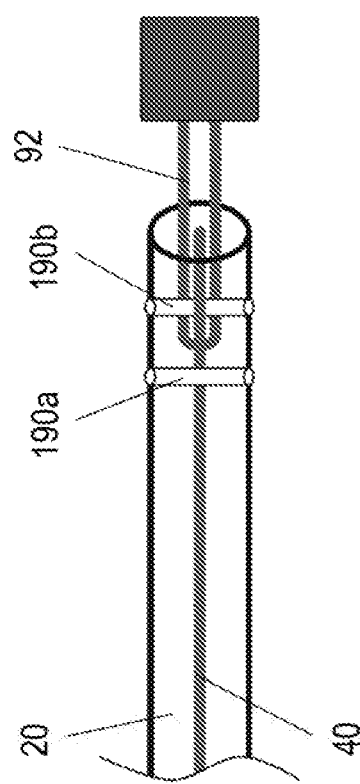
FIG. 12A

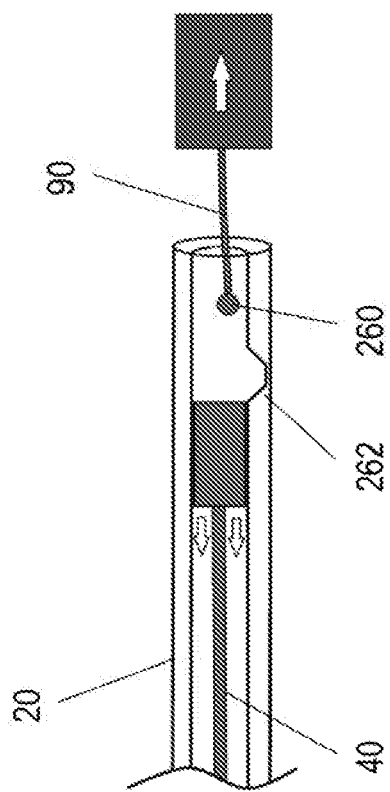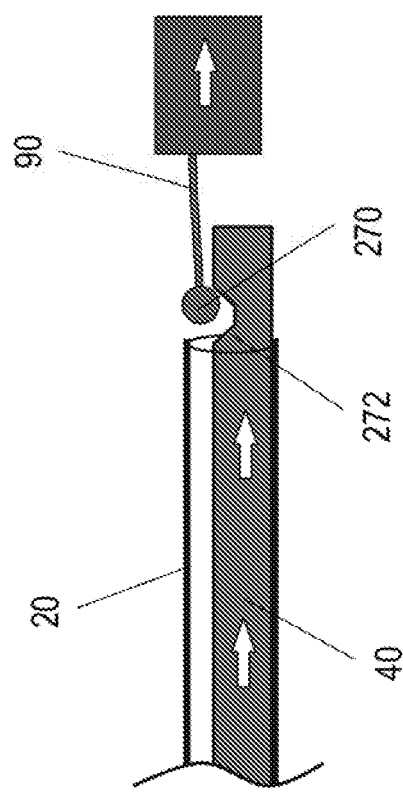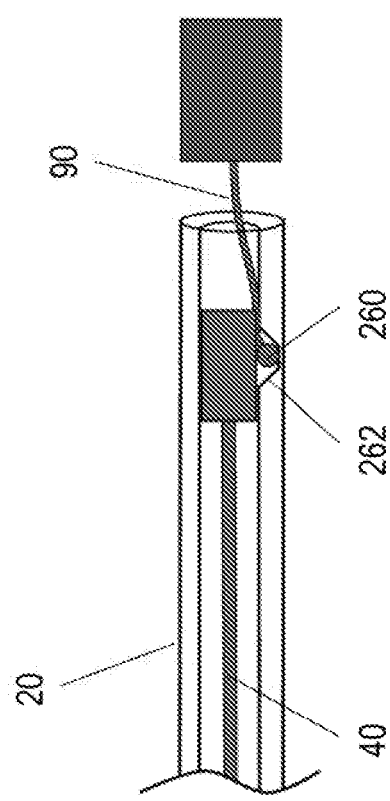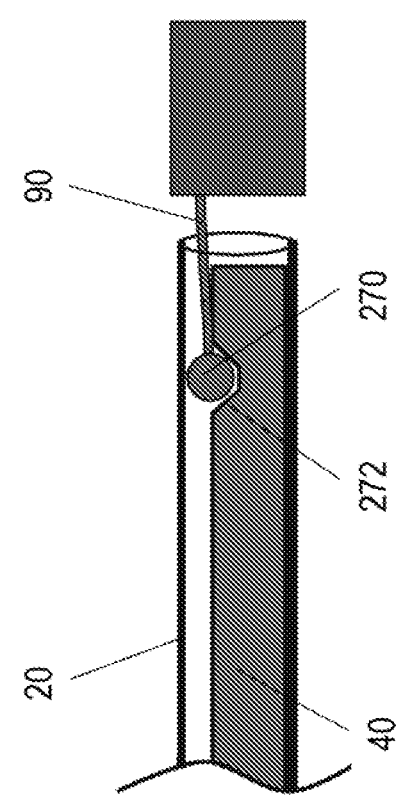

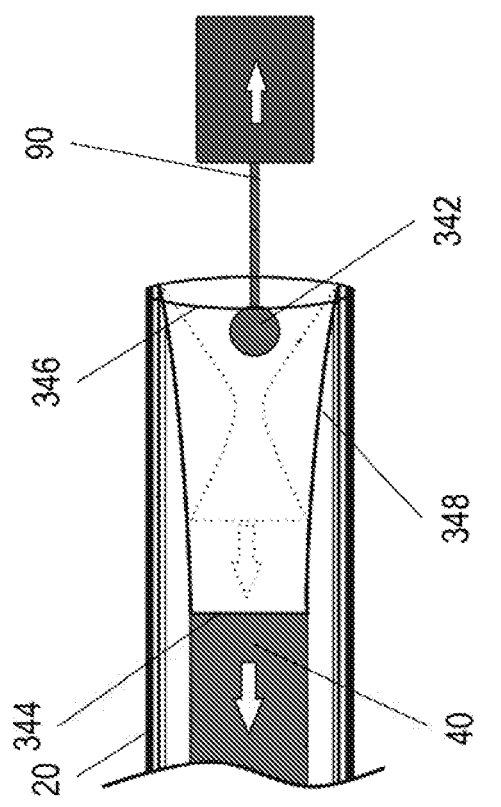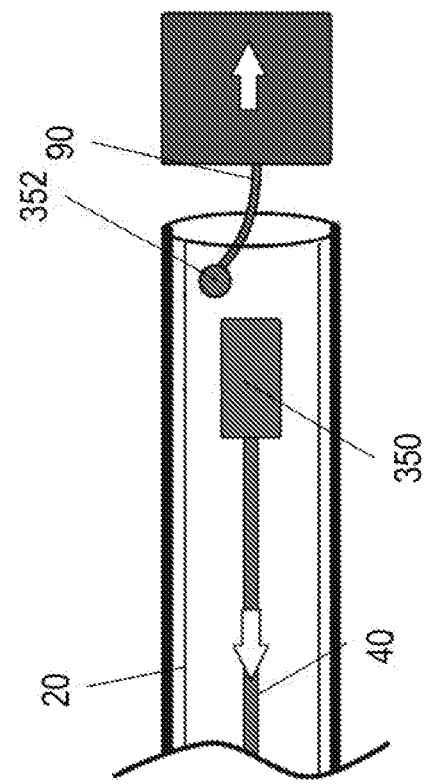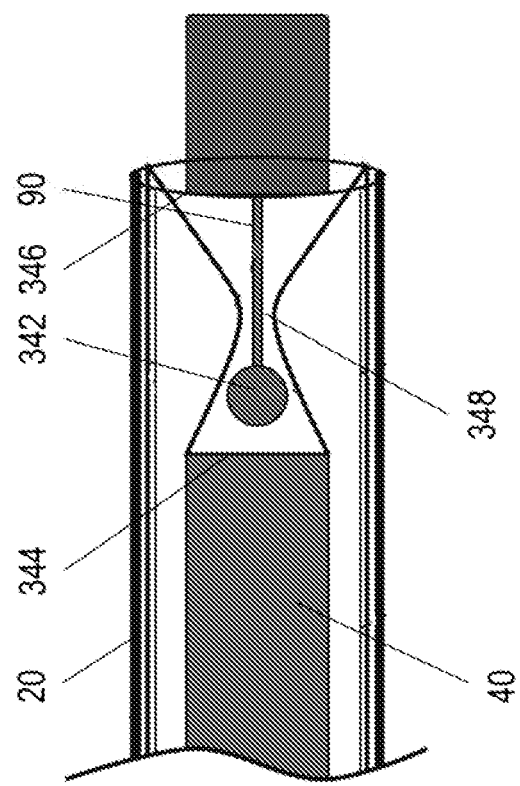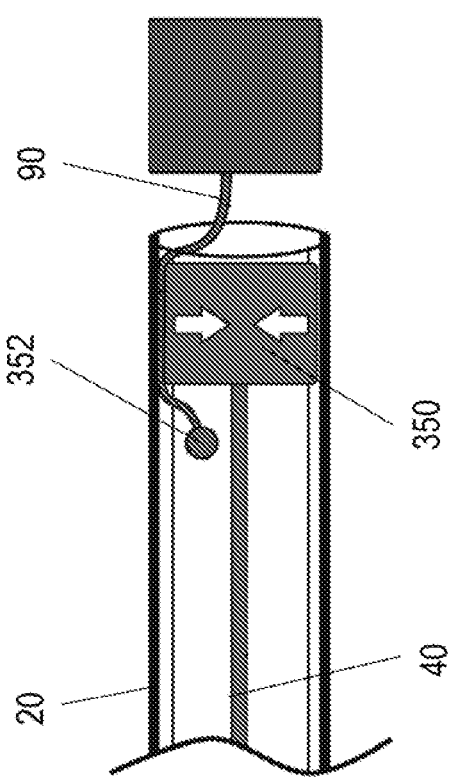
FIG. 28B
FIG. 29B
FIG. 28A
FIG. 29A

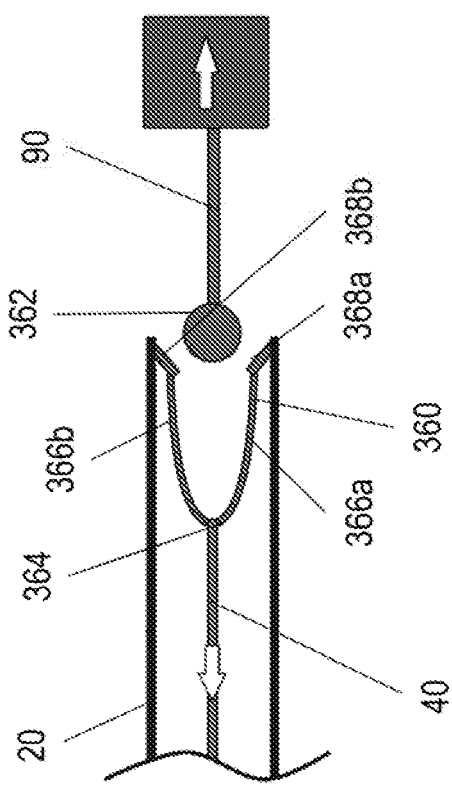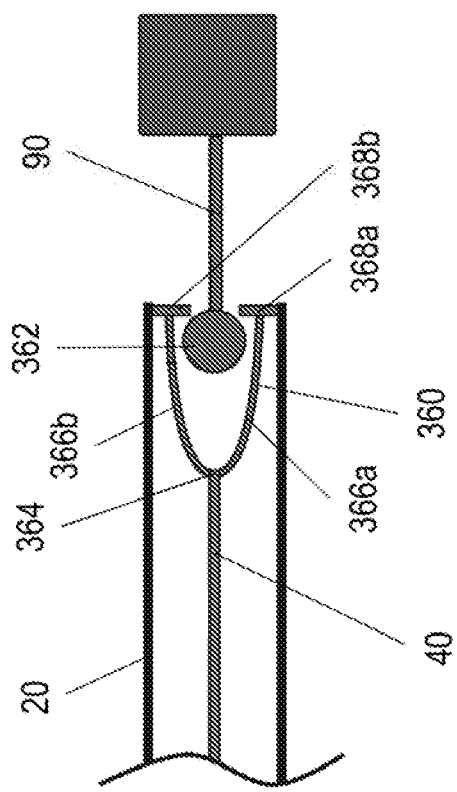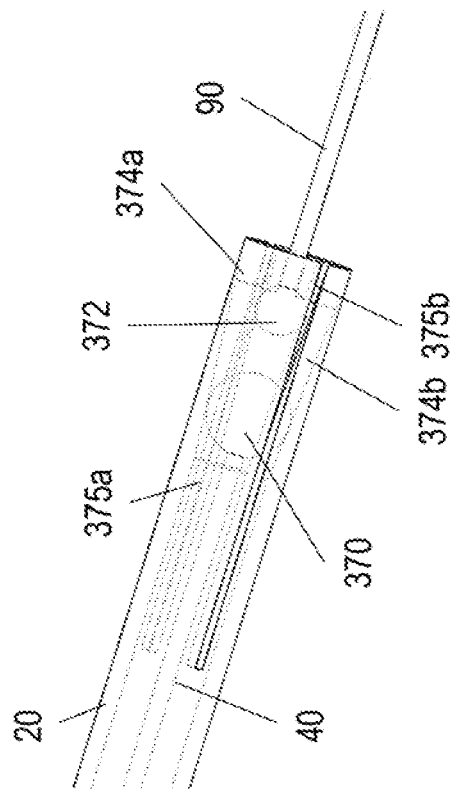

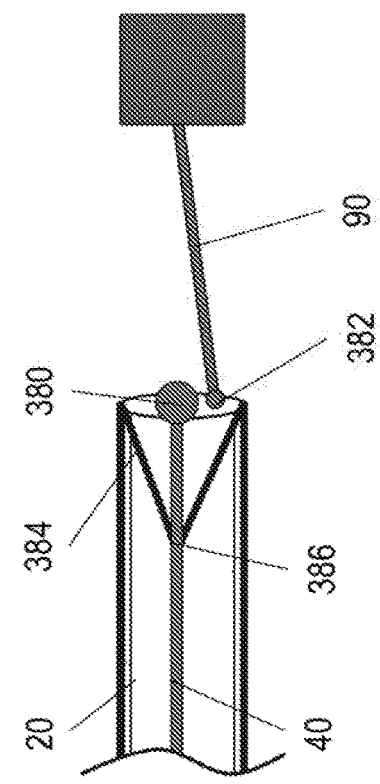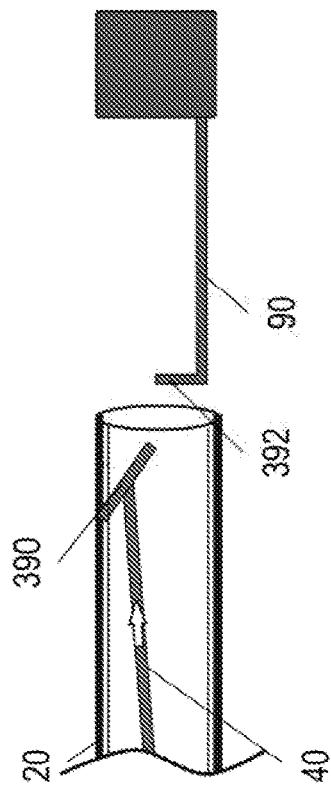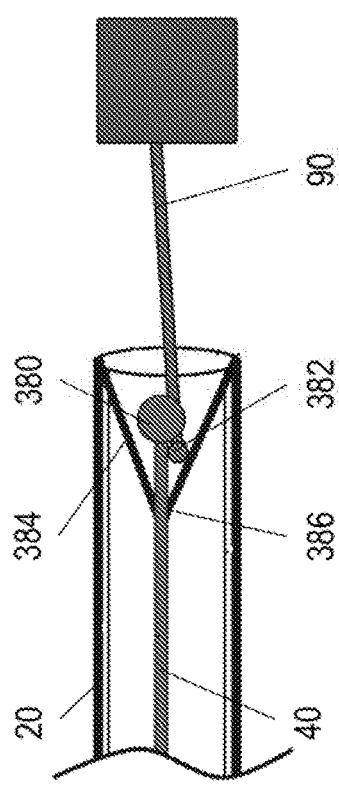
FIG. 32A
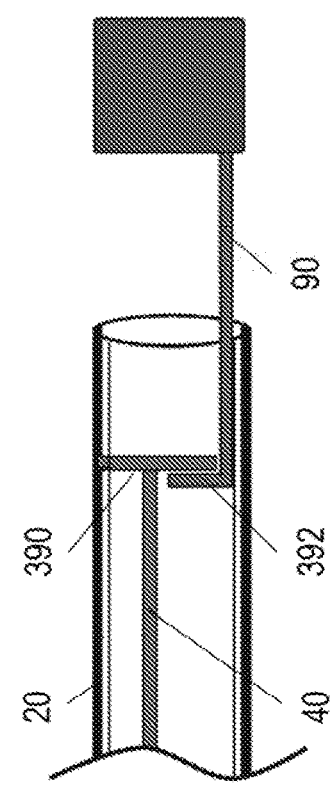
FIG. 33A

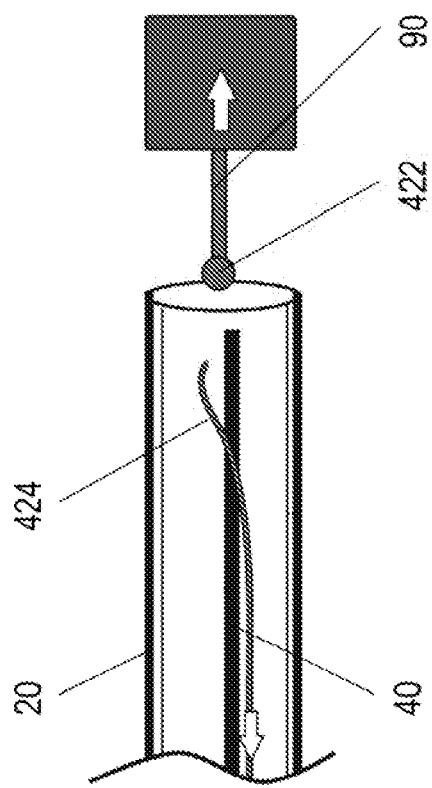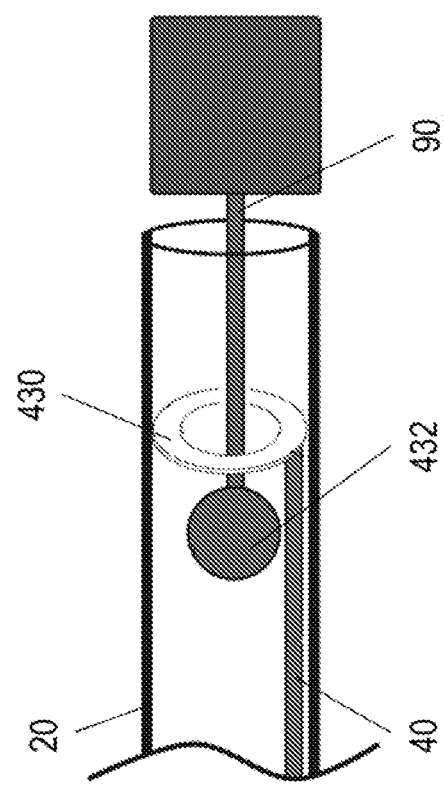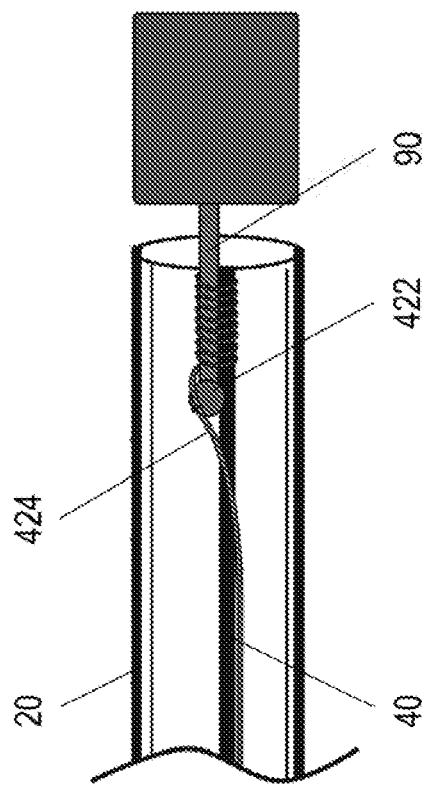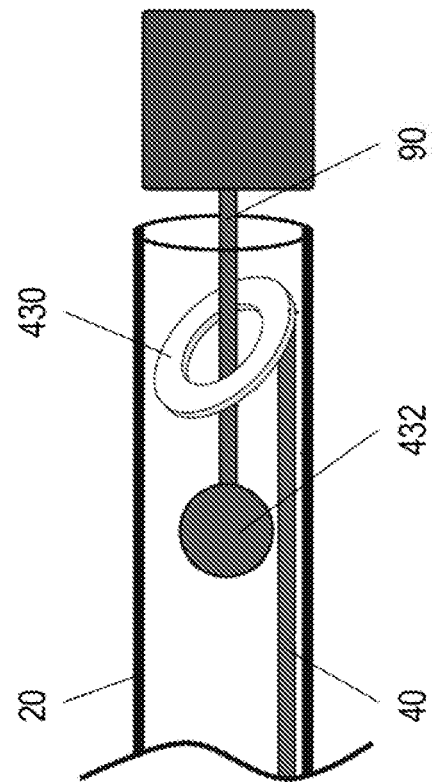

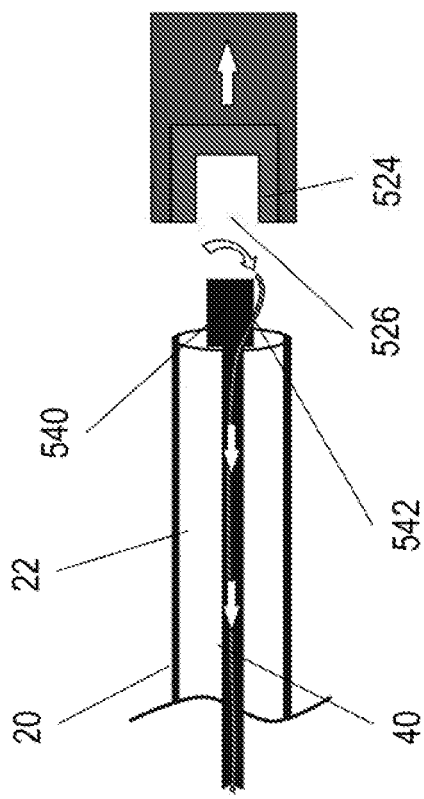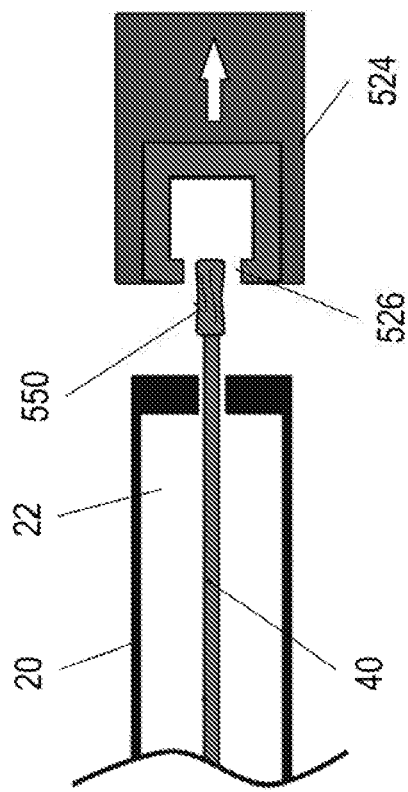
FIG. 48B    FIG. 49B
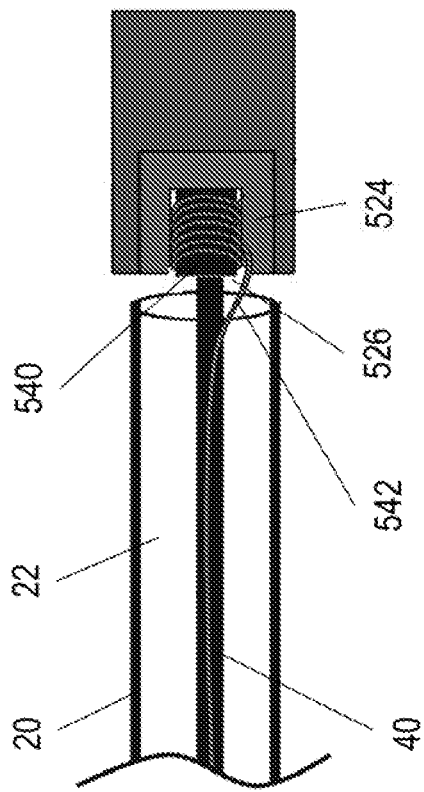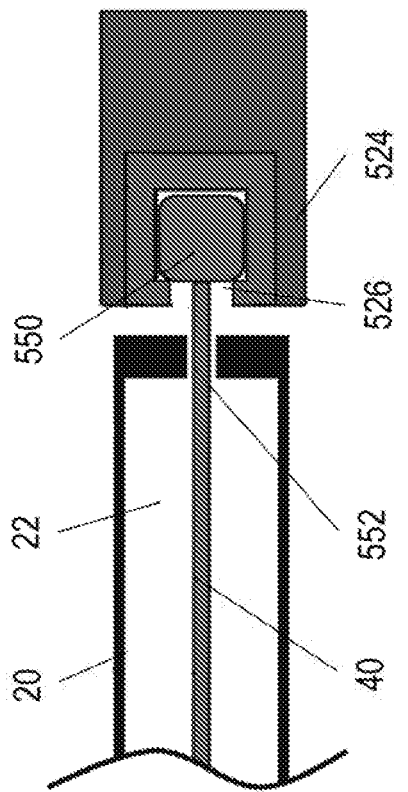
FIG. 48A    FIG. 49A

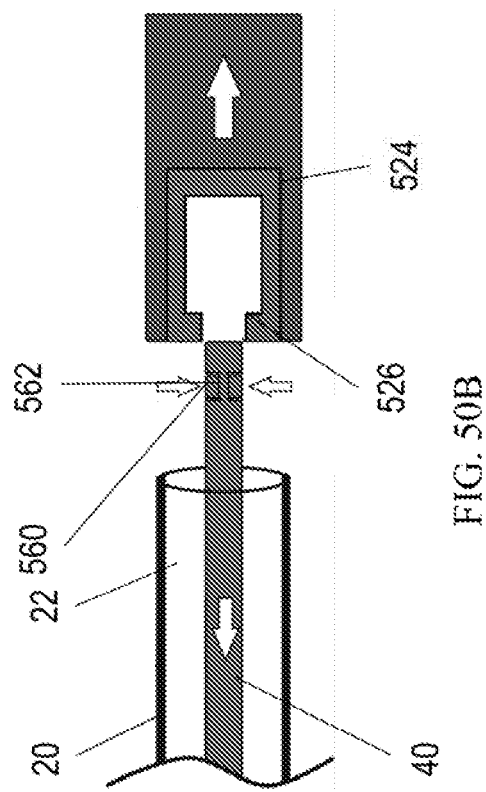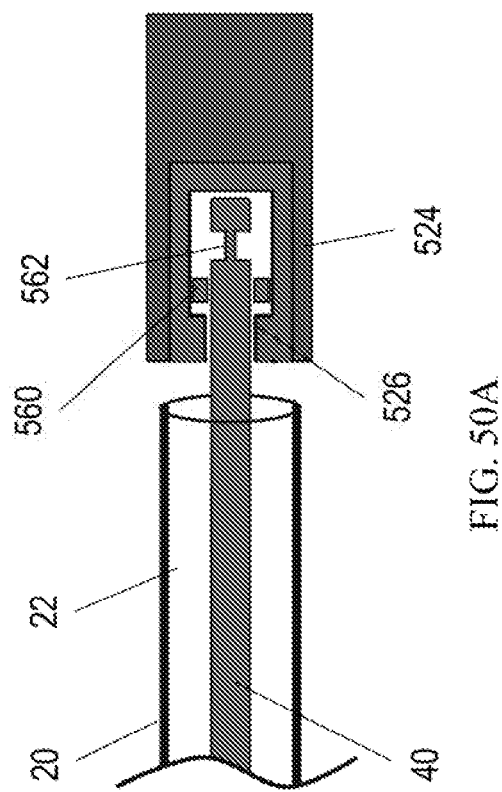
FIG. 50A
FIG. 50B
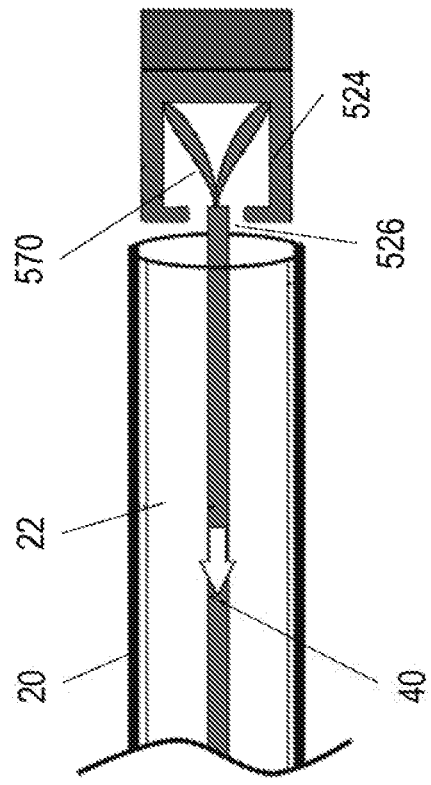
FIG. 51

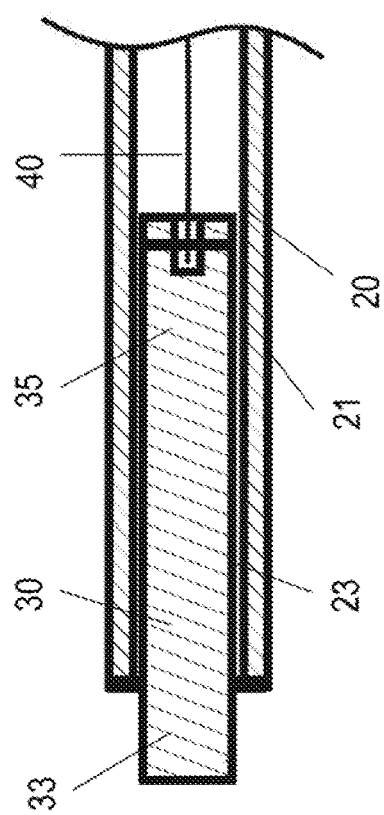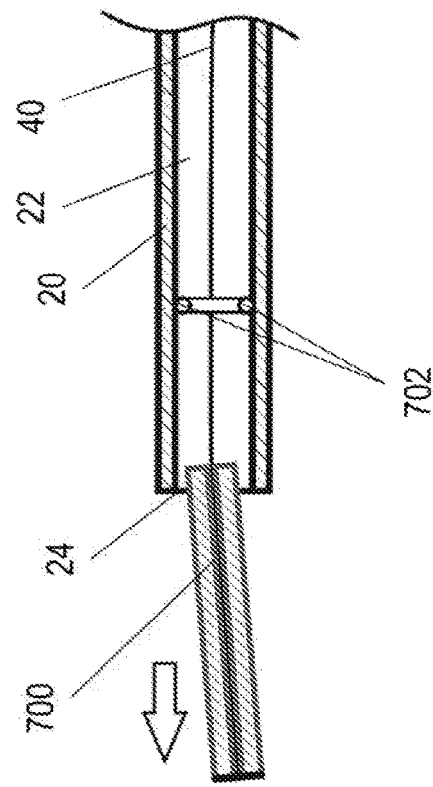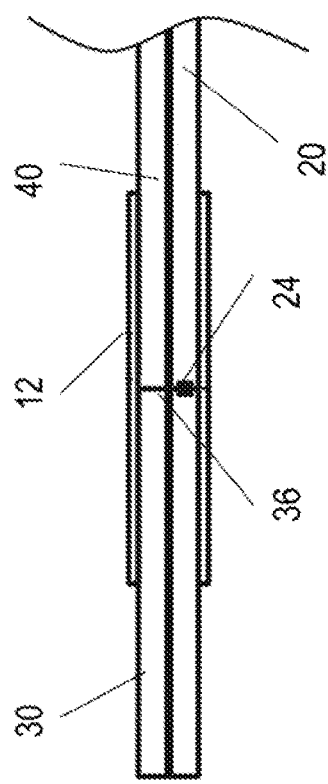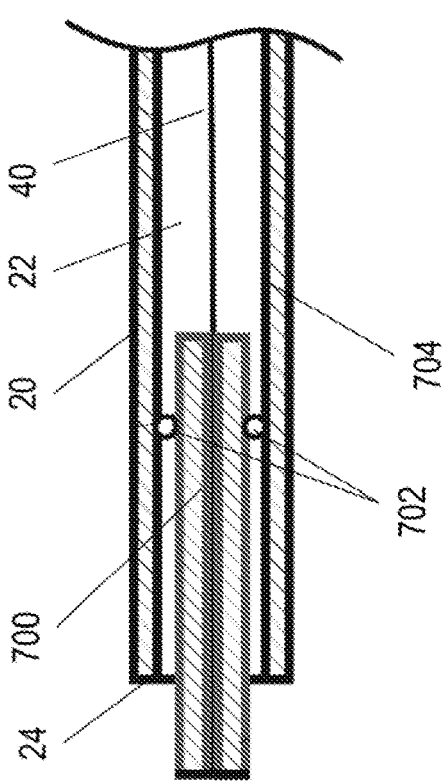

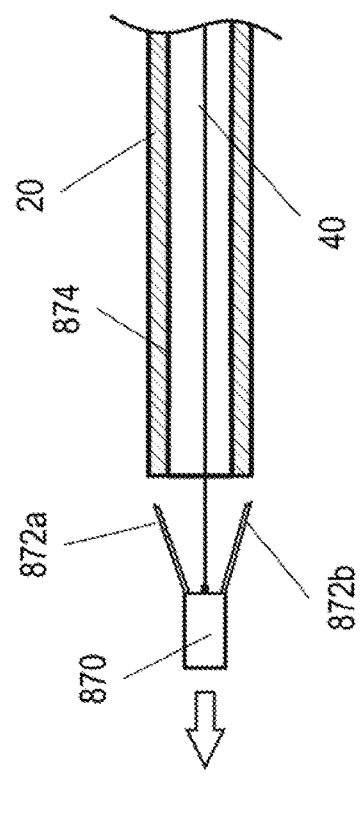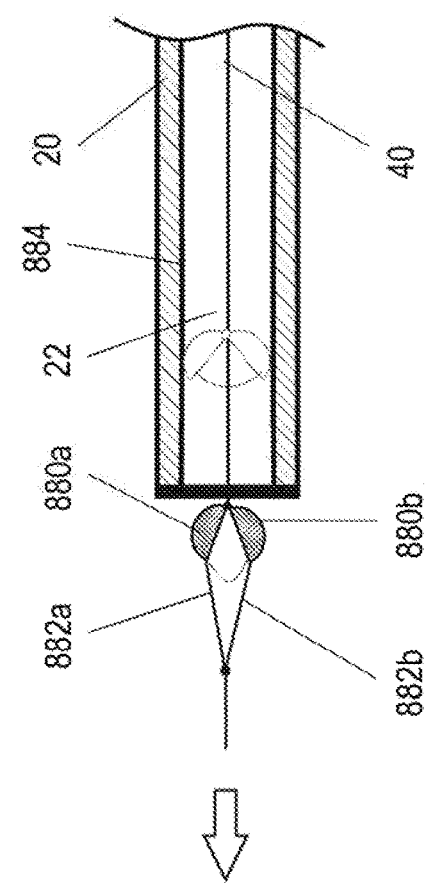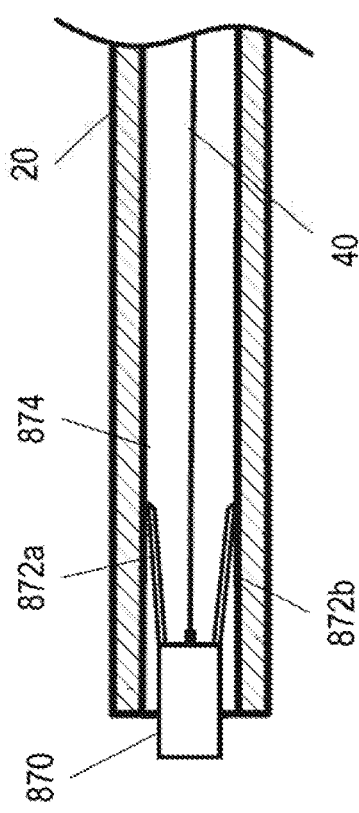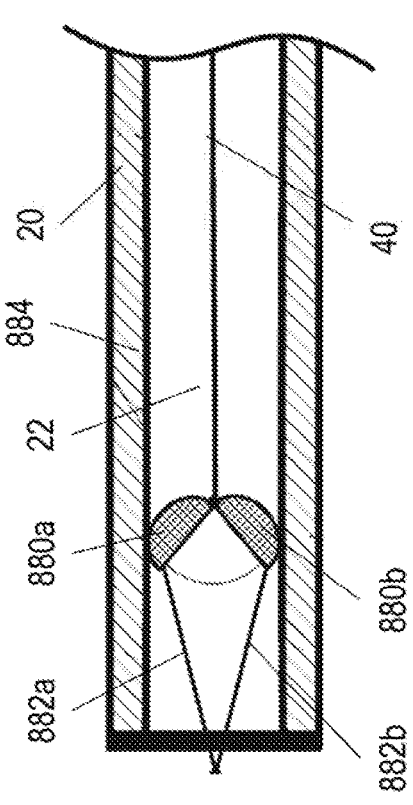

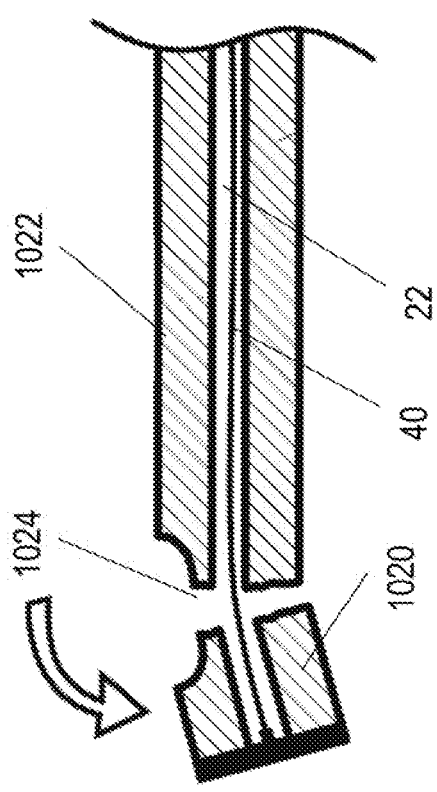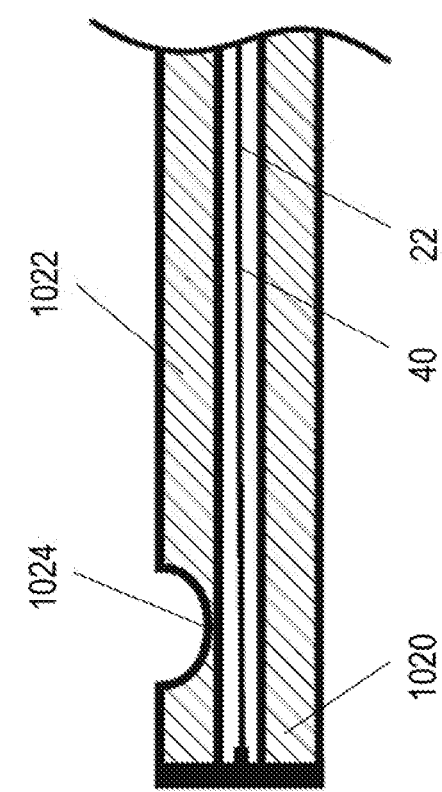
FIG. 93B
FIG. 93A
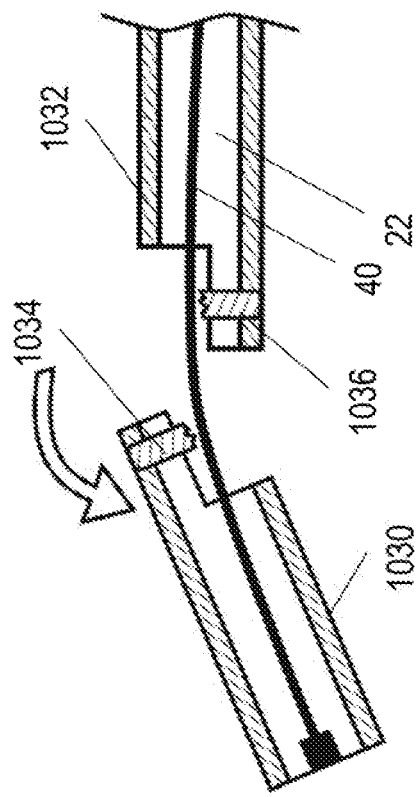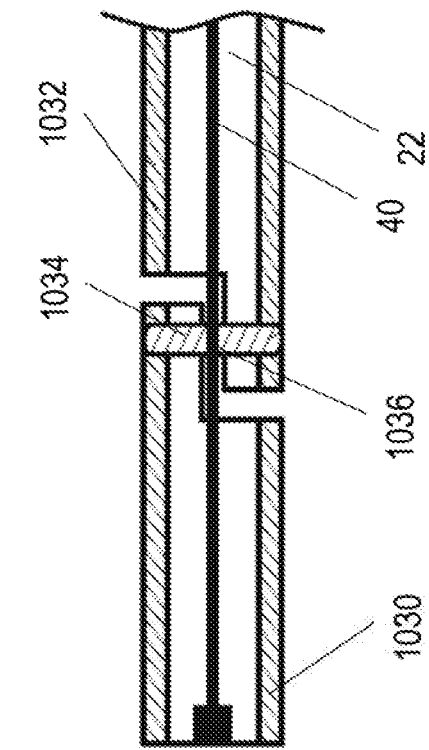
FIG. 94B
FIG. 94A

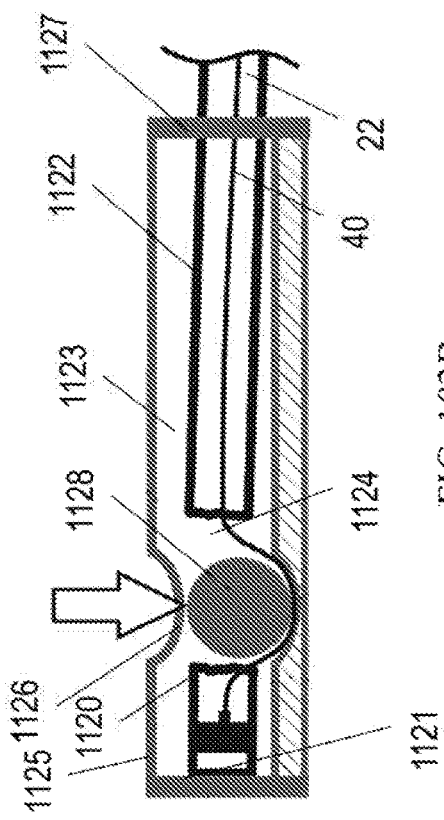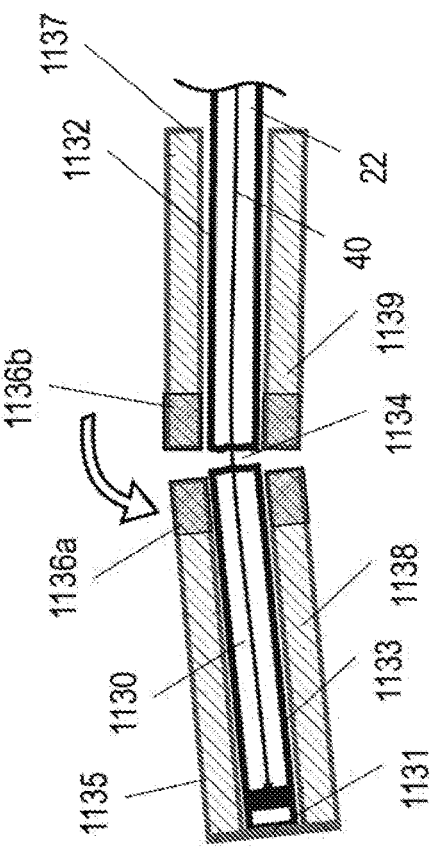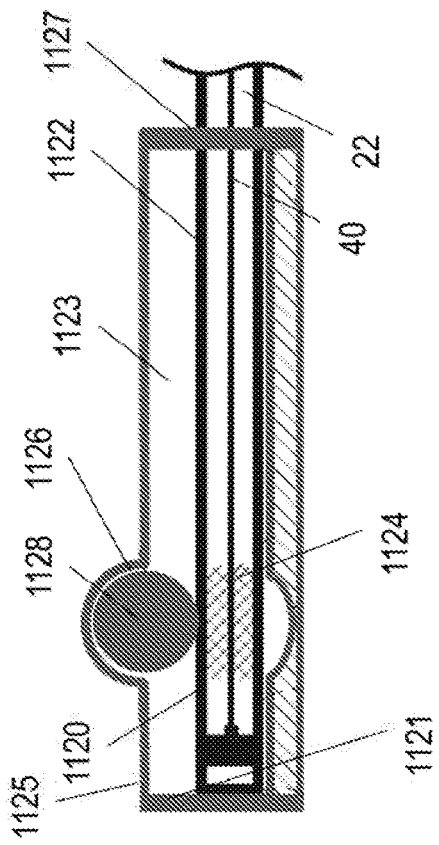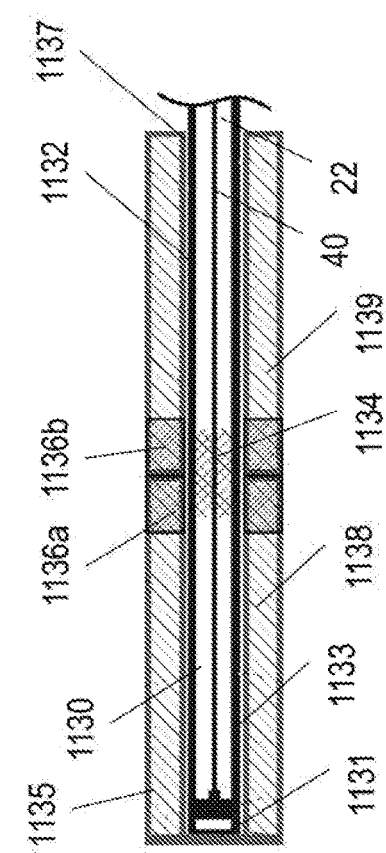

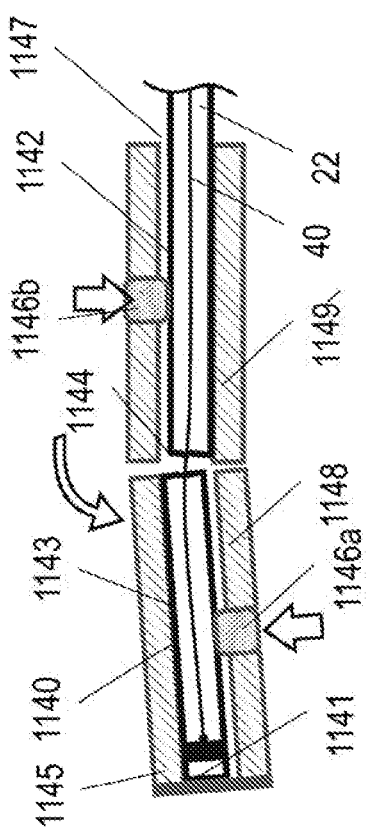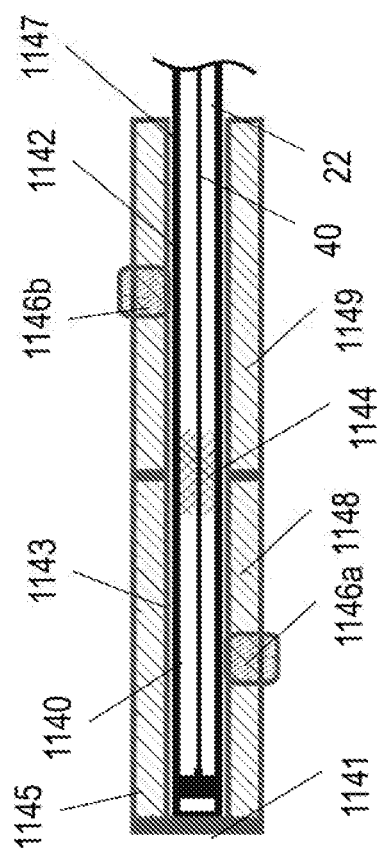
FIG. 105A
FIG. 105B
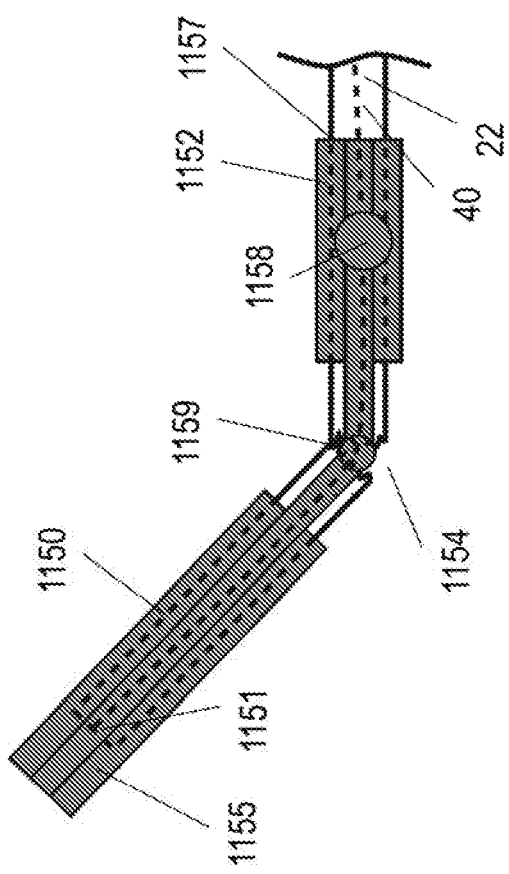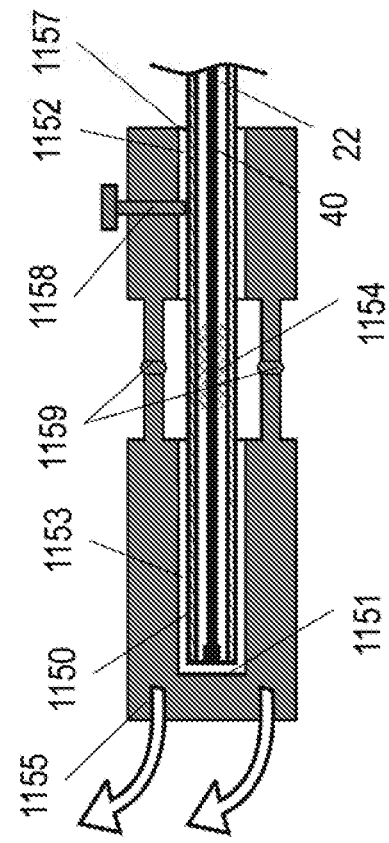
FIG. 106A
FIG. 106B

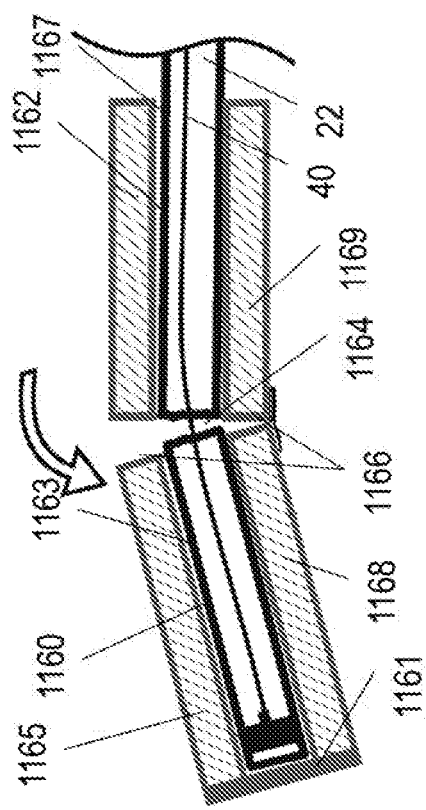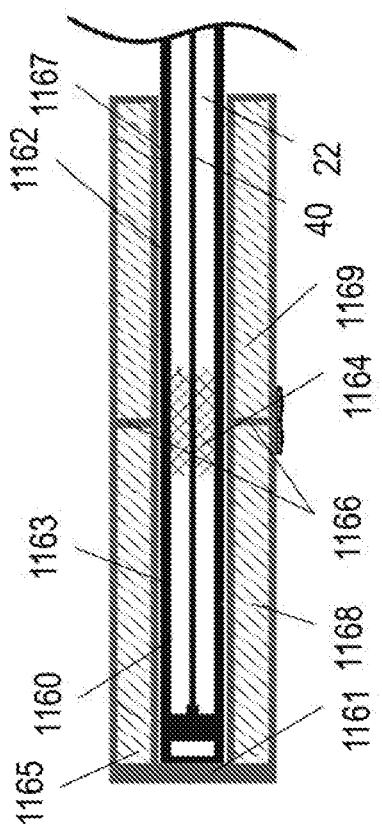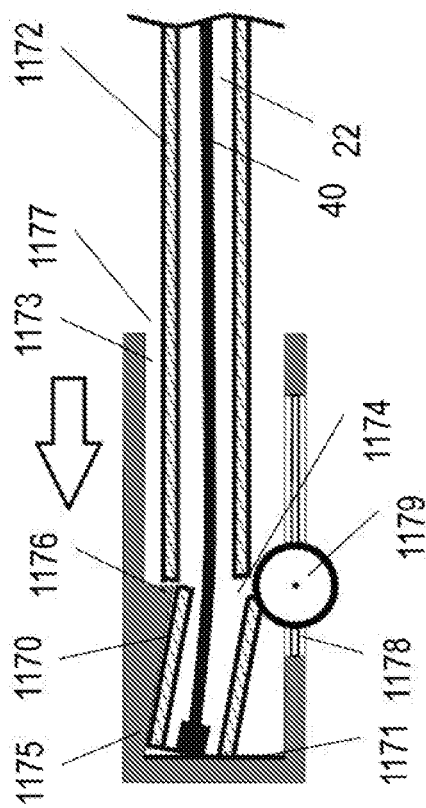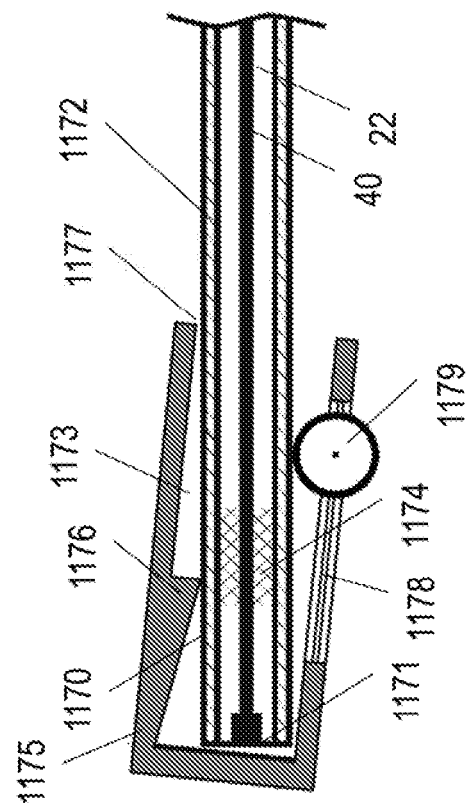

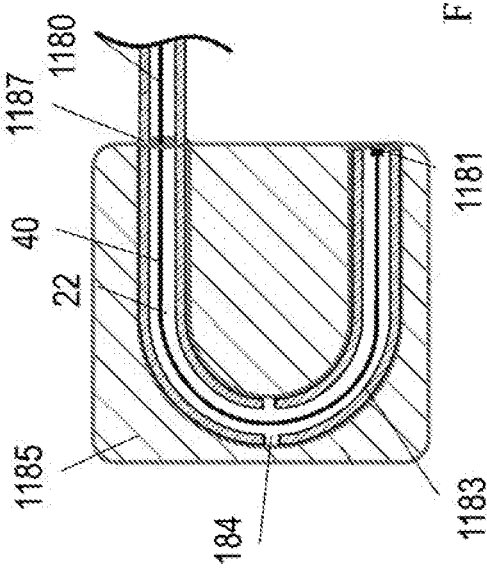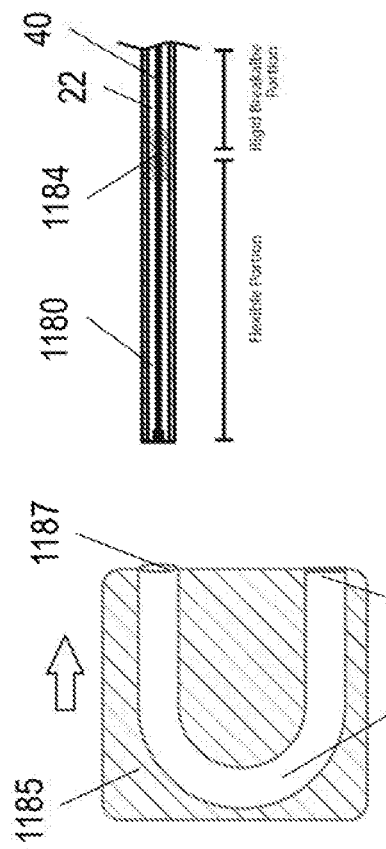
FIG. 109A
FIG. 109B
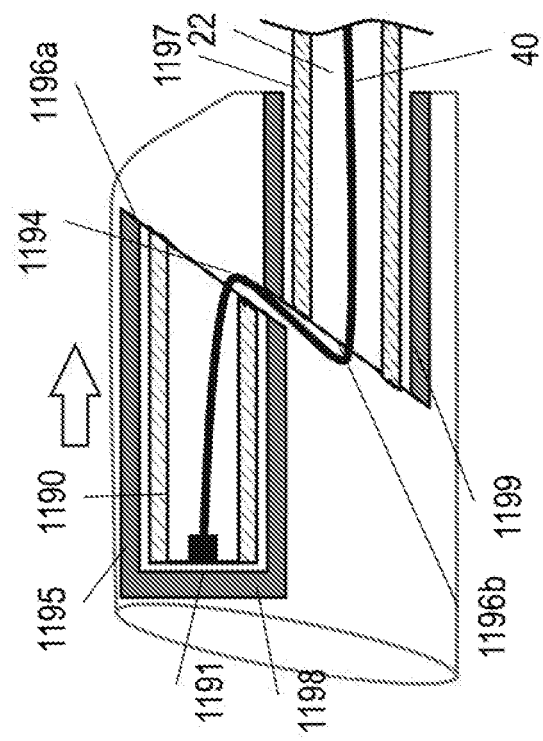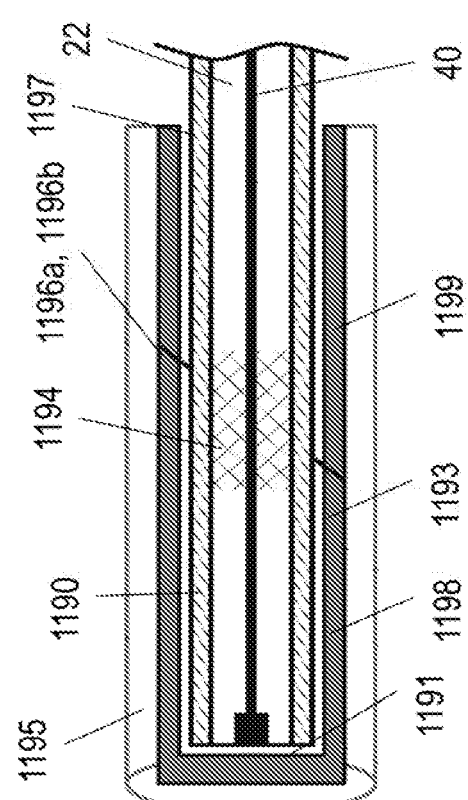
FIG. 110A
FIG. 110B

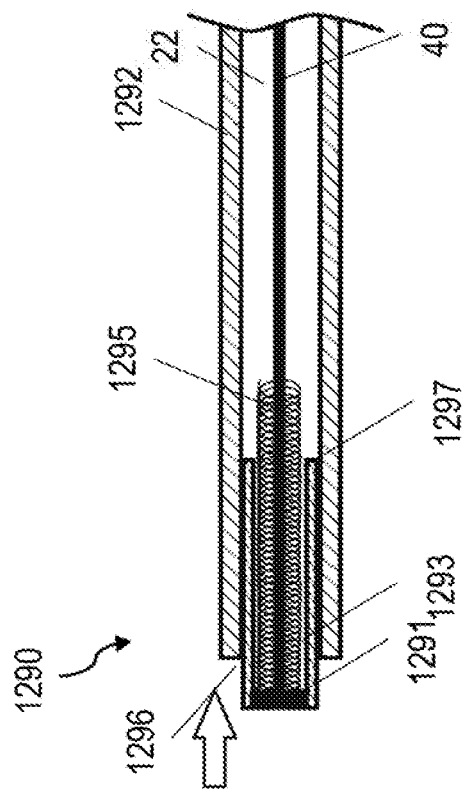
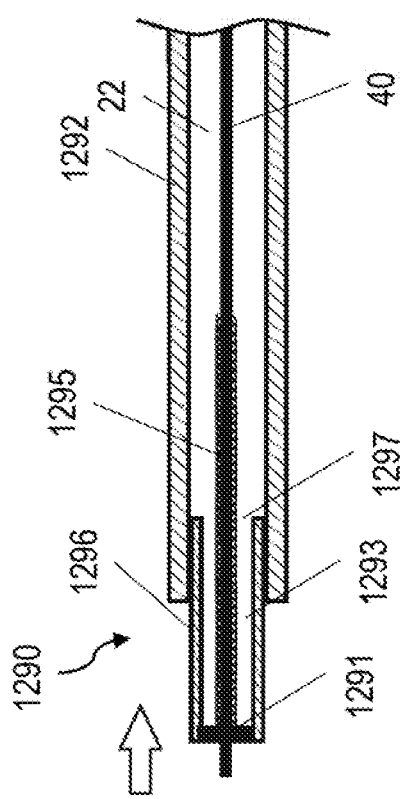

200~# IMPLANT DELIVERY SYSTEMS AND METHODS

CROSS-REFERENCE TO RELATED APPLICATION

This application is a U.S. national phase application under 37 U.S.C. § 371 of International Application No. PCT/US17/034895 filed on May 28, 2017, which claims priority to and the benefit of U.S. Provisional Patent Application Ser. No. 62/368,927, entitled "Implant Delivery Systems and Methods," filed Jul. 29, 2016, and U.S. Provisional Patent Application Ser. No. 62/435,381, entitled "Implant Delivery Systems and Methods," filed Dec. 16, 2016. The entirety of each of PCT/US 17/34895 and U.S. Provisional Applications Ser. Nos. 62/368,927 and 62/435,381 are incorporated herein by reference.

TECHNICAL FIELD

The present invention relates generally to systems and method for delivery of one or more implants into a patient, and in particular implant delivery systems and devices that provide a rapid release of the implant at a desired implantation location.

BACKGROUND OF THE INVENTION

Vaso-occlusive devices, stents and other implants are used for a variety of medical treatments, including the treatment of intra-vascular aneurysms and vascular restrictions. Vaso-occlusive devices often include a soft, helically wound coil that is positioned in a blood vessel or aneurysm, such as a blood vessel or aneurysm of the brain. Stents can comprise resiliently biased structures that self-expand or plastically deformable structures that are expanded through the use of an inflatable balloon. Vaso-occlusive devices, stents and other implants are often accompanied by a catheter-based delivery device which is introduced percutaneously into a patient, and advanced proximate a site for implantation. Precision of placement of one or more implants at a desired location is often difficult to the manner in which the implant is released from the delivery catheter.

SUMMARY

An aspect of the present teachings provides a medical system for delivering and deploying an implant into a patient. In various embodiments each of the medical system comprises a medical implant and an implant delivery system. In some embodiments, the medical implant comprises a proximal engagement loop. The implant delivery system comprises an implant pusher shaft and an engagement wire. In certain embodiments, the implant pusher shaft comprises an elongated lumen with a proximal end, a distal end, and an interface joining the distal end. The engagement wire comprises an elongated body with a proximal end and a distal end, and is configured to slidably dispose within the longitudinal lumen of the implant pusher shaft. The medical system has a first configuration where at least a portion of the engagement loop extends from a distal side of the interface to a proximal side of the interface, and the proximal end of the engagement wire extends from the proximal side of the interface to the distal side of the interface, and wherein the engagement wire engages the engagement loop of the implant. In particular embodiments, the medical system also has a second configuration where the proximal end of the engagement wire extends proximally away from the interface and disengages the engagement loop of the implant.

One embodiment of the present teachings provides a medical system, wherein the interface comprises two fingers joining by a cross pin. In particular embodiments, in the first configuration, a portion of the engagement loop extends proximally beyond the cross pin at its first side, and the proximal end of the engagement wire extends distally first through the engagement loop and then further distally beyond the cross pin at its second side.

One embodiment of the present teachings provides a medical system, wherein the interface comprises a tubular body with a center lumen. In particular embodiments, the interface joins the distal end of the implant pusher shaft inside its longitudinal lumen. In the first configuration, a portion of the engagement loop extends from outside of the tubular body of the interface proximally, and the proximal end of the engagement wire extends distally first through the portion of the engagement loop and then further distally through the tubular body of the interface.

One embodiment of the present teachings provides a medical system, wherein the interface comprises a ramp body joining the distal end of the implant pusher shaft inside its longitudinal lumen. In particular embodiments, in the first configuration, a portion of the engagement loop extends proximally beyond the ramp body of the interface, and the proximal end of the engagement wire extends distally first through the portion of the engagement loop and then further distally and engages the ramp body of the interface.

One embodiment of the present teachings provides a medical system, wherein the implant delivery system further comprises an implant release control mechanism fixedly joining the proximal end of the engagement wire. In particular embodiments, in the first configuration, the implant release control mechanism attaches the proximal end of the implant pusher shaft. Additionally, in the second configuration, the implant release control mechanism disconnects the proximal end of the implant pusher shaft.

An aspect of the present teachings provides a medical system for delivering and deploying an implant into a patient. In various embodiments each of the medical system comprises a medical implant and an implant delivery system. In some embodiments, the medical implant comprises a proximal engagement loop. The implant delivery system comprises an implant pusher shaft and an engagement wire. In certain embodiments, the implant pusher shaft comprises an elongated lumen with a proximal end, a distal end, and an interface joining the distal end. The engagement wire comprises an elongated body with a proximal end and a distal end, and is configured to slidably dispose within the longitudinal lumen of the implant pusher shaft. The medical system has a first configuration where a portion of the engagement loop extends to a location proximal to at least a portion of the interface, and the engagement wire interacts with the interface and thereby prevents unintended distal movement of the portion of the engagement loop.

One embodiment of the present teachings provides a medical system, wherein the engagement wire interacts with the interface by extending through the engagement loop of the implant and further distally so that the distal end of the engagement wire is distal to at least a portion of the interface.

One embodiment of the present teachings provides a medical system, wherein the engagement wire interacts with the interface by extending through the engagement loop of the implant and adjoins a surface of the interface.

One embodiment of the present teachings provides a medical system, wherein the implant delivery system further comprises an implant release control mechanism fixedly joining the proximal end of the engagement wire. In particular embodiments, in the first configuration, the implant release control mechanism attaches the proximal end of the implant pusher shaft. In the second configuration, the implant release control mechanism disconnects the proximal end of the implant pusher shaft.

One embodiment of the present teachings provides a medical system, wherein as the medical system in its first configuration, the distal end of the engagement wire is at its most distal position. In particular embodiments, as the medical system transitioning from the first configuration to the second configuration, the distal end of the engagement wire retracts proximally.

BRIEF DESCRIPTION OF THE DRAWINGS

FIG. 2B is a perspective view of an exemplary implant pusher shaft in accordance with the present teachings;

FIGS. 4-19 are perspective views of various exemplary engagement between a delivery system and a medical implant where an engagement loop of the implant is captured by the engagement wire, the interface at the distal end of the implant pusher shaft, or a combination of both in accordance with the present teachings;

FIGS. 20-37 are perspective views of various exemplary engagement between a delivery system and a medical implant where an enlarged proximal end of the implant is captured by the engagement wire, the implant pusher shaft, or, a combination of both in accordance with the present teachings;

FIGS. 46-52 are perspective views of various exemplary engagement between a delivery system and a medical implant via a bracket engagement feature in accordance with the present teachings;

FIGS. 60-80 are perspective views of various exemplary implant release control mechanism where it is a separate component that joins the proximal end of the engagement wire in accordance with the present teachings;

FIGS. 91-110 are perspective views of various exemplary implant release control mechanism where the implant release control mechanism is a breakable proximal portion of the implant pusher shaft in accordance with the present teachings;

FIGS. 119-120 are perspective views of various exemplary implant release control mechanism in accordance with the present teachings.

DETAILED DESCRIPTION

Figure 1:
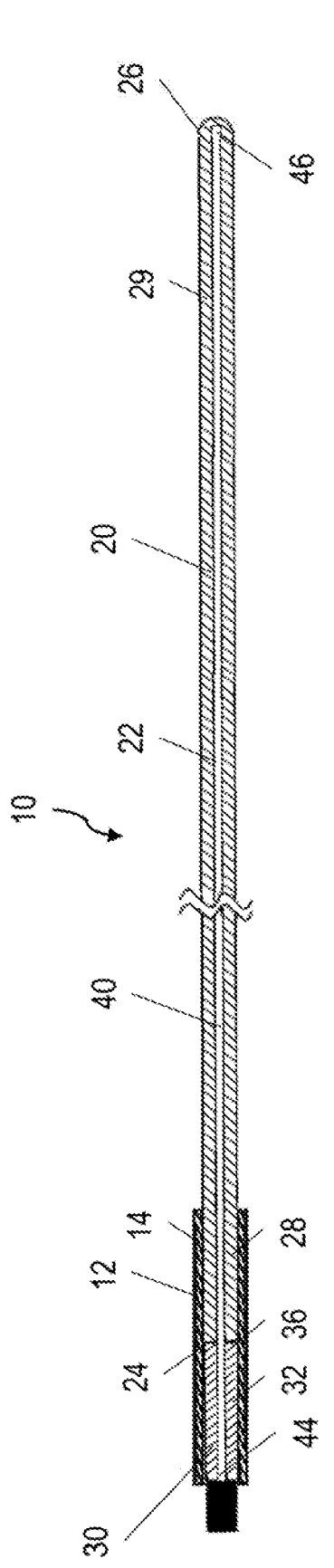
FIG. 1 is a perspective view of an exemplary delivery system in accordance with the present teachings.

Certain specific details are set forth in the following description and figures to provide an understanding of various embodiments of the present teachings. Those of ordinary skill in the relevant art would understand that they can practice other embodiments of the present teachings without one or more of the details described herein. Thus, it is not the intention of the applicant(s) to restrict or in any way limit the scope of the appended claims to such details. While various processes are described with reference to steps and sequences in the following disclosure, the steps and sequences of steps should not be taken as required to practice all embodiments of the present teachings.

As used herein, the term "lumen" means a canal, a duct, or a generally tubular space or cavity in the body of a subject, including a vein, an artery, a blood vessel, a capillary, an intestine, and the like. The term "lumen" can also refer to a tubular space in a catheter, a sheath, a hollow needle, a tube, or the like.

As used herein, the term "proximal" shall mean close to the operator (less into the body) and "distal" shall mean away from the operator (further into the body). In positioning a medical device inside a patient, "distal" refers to the direction relatively away from a catheter insertion location and "proximal" refers to the direction relatively close to the insertion location.

As used herein, the term "wire" can be a strand, a cord, a fiber, a yarn, a filament, a cable, a thread, or the like, and these terms may be used interchangeably.

As used herein, the term "sheath" may also be described as a "catheter" and, thus, these terms can be used interchangeably.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and appended claims are approximations. At the very least and not as an attempt to limit the application of the doctrine of equivalents to the scope of the claims, numerical parameters should be read in light of the number of reported significant digits and the application of ordinary rounding techniques.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

The present teaching relate to an implant-delivery system assembly for engaging, delivering, deploying and releasing one or more implants into a patient. In some embodiment, the delivery system includes an implant pusher shaft (20) for pushing the implant forward during delivery and deployment; an implant engagement mechanism configured to releasably engage a medical implant during delivery and deployment. The delivery system further includes an implant release control mechanism for disengaging the medical implant and release it at the treatment location. The control mechanism is constructed and arranged to release the engagement between the implant and the delivery system.

FIG. 1 illustrates an embodiment of the delivery system (10). According to some embodiments, the delivery system (10) includes an implant release control mechanism (30), an implant pusher shaft (20), and an implant engagement wire (40). The implant pusher shaft (20) has an elongated lumen (22) extending from its proximal end (24) to the distal end (26). As illustrated, the implant engagement wire (40) is slidably disposed within the axial lumen (22) of the implant pusher shaft (20). According to one embodiment of present teachings, the implant engagement wire (40) is configured to extend distally or retract proximally independent of the implant pusher shaft (20). Further referring to FIG. 1, the implant release control mechanism (30) fixedly engages to the proximal end (44) of the implant engagement wire (40) and is positioned proximal to the proximal end (24) of the implant pusher shaft (20).

Continuing to refer to FIG. 1, the implant pusher shaft (20) also has a flexible distal portion (29), which allows the delivery system (10) to maneuver through tortuous paths of the human vasculature. Without attempting to limit the scope of present teachings, such flexible distal portion (29) of the implant pusher shaft (20) is configured to offer mechanical properties such as column strength for pushing the medical implant, stretch resistance when the product is retracted, and flexibility when the distal tip (26) of the implant pusher shaft (20) enters the aneurysm or when the medical implant is deployed.

Figure 2A:
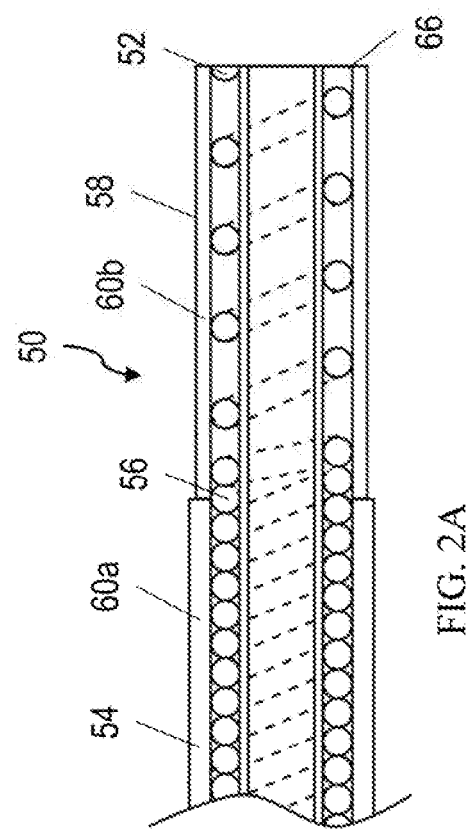
FIG. 2A is a perspective sectional view of an exemplary implant pusher shaft in accordance with the present teachings.

An exemplary embodiment of the implant pusher shaft (50) is illustrated in FIG. 2A, according to one embodiment, the flexible distal portion (58) is constructed of a multi-filar coil (56). As shown in the figure and in some embodiments, a proximal portion (54) of the coil (56) is wounded with a higher pitch than a distal portion (58). This would result a relatively more flexible distal portion. One skilled in the art should understand that the flexible distal portion can be constructed of a unifilar coil, multi-filar coil, or a braid. In some embodiments, the coil construct can be of a helical or spiral pattern. In some embodiments, the flexible distal portion is made of the coil construct alone. In another embodiment, the coil construct covers either the outer and/or inner cylindrical surface of the implant pusher shaft (50), or is embedded within the wall of the implant pusher shaft (50). One skilled the in the art should understand, that in the embodiments where the coil covers or is embedded inside the implant pusher shaft (50) wall, either the distal portion (58) of the implant pusher shaft (50) material, or the thickness of the such portion of the implant pusher shaft (50) can vary from the rest portion of the implant pusher shaft (50), for example, to achieve the flexible design nature.

In another embodiment, a flexible distal portion (78) of the implant pusher shaft (70) could also be achieved by other means. FIG. 2B illustrates another embodiment where the distal portion (78) of the implant pusher shaft (70) has a generally smaller outer diameter (OD) compared to its proximal portion (64). A tapered transition portion (76) in between the proximal and distal portion (78) of the implant pusher shaft (70) ensure the overall smoothness of the implant pusher shaft (70). For example, the proximal portion (74) of the implant pusher shaft (70) could have a 0.014" general diameter, and the distal portion (78) of the implant pusher shaft (70) could have a 0.011" general diameter. In another embodiment, the proximal portion (74) of the implant pusher shaft (70) could have a length of approximately 1175 mm, and the distal portion (78) of the implant pusher shaft (70) could a length of approximately 125 mm while the transitional tapered portion (76) could have a length of approximately 200 mm.

In some embodiments, the implant pusher shaft is made of one or more plastic and/or metal materials, each independently chosen from stainless steels; shaped memory metals; nickel titanium alloys; polymers; shaped memory polymers; or combinations of one or more of these. In other embodiments, the filament used in making the coil/braid construction can be of a metal and/or a plastic. In yet other embodiments, the filament used in coil/braid construction ranges from 0.00125" to 0.0015" for a multi-filar coil construct.

According to some embodiment, such as shown in FIG. 2A, the overtube (60a, 60b) slides over the implant pusher shaft (20), such as the one made of coil as shown in the figure, with its distal end (66) positioning approximate to the distal end (52) of the implant pusher shaft (50). In one embodiment, the overtube (60a, 60b) is configured to provide a lubricious surface and adds to the column strength as well as the stretch resistance to the implant pusher shaft (20). In some embodiments, the proximal end of the overtube (60a, 60b) is located proximally to the proximal end of the flexible distal portion of the implant pusher shaft (50). One skilled in the art should understand that the proximal end of the overtube (60a, 60b) could be located near the proximal end of the implant pusher shaft (50) or somewhere between the proximal end of the implant pusher shaft (50) and the proximal end of the flexible distal portion of the implant pusher shaft (50). In one embodiment, the overtube (60a, 60b) is made of a polymer, for example PTFE or PET which is a heat shrinkable material, or a combination of both. In another embodiment, the overtube (60a, 60b) has a thickness between 0.0010" and 0.0025". In yet another embodiment, the overtube (60a, 60b) could have various thickness covering each portion of the implant pusher shaft (50), such as illustrated in FIG. 2A. Although an overtube (60a, 60b) is disclosed and described here, one skilled in the art should understand that as the design, material, and/or construct of the implant pusher shaft varies, the overtube (60a, 60b) might not be necessary. Thus, what has been disclosed herein should not be viewed as limiting to the overall scope of the present teachings.

Continuing referring to FIG. 1, the proximal end (24) of the implant pusher shaft (20) engages an implant release control mechanism (30) by a connector (12). In one embodiment, the implant release control mechanism (30) fixedly joins the proximal end (44) of the implant engagement wire (40), and releasably engages the implant pusher shaft (20). A distal portion (32) of the implant release control mechanism (30) frictionally engages the connector lumen (14). A proximal portion (28) of the implant pusher shaft (20) also frictionally engages the connector lumen (14). According to some embodiment, the distal end (36) of the implant release control mechanism (30) engages the proximal end (24) of the implant pusher shaft (20). During implant delivery and deployment, a clinician extends the implant pusher shaft (20) and the implant release control mechanism (30) distally and/or retract proximally together, and thereby allows a secure engagement between the delivery system (10) and the medical implant. The implant release control mechanism (30) is also configured to be activated by proximal retraction to the implant engagement wire (40) by a clinician holding the connector (12) and retracting the implant release control mechanism (30) proximally to break the engagement between the implant release control mechanism (30) and the implant pusher shaft (20), and thereby release the medical implant. According to one embodiment, an implant engagement wire is slidably disposed within the axial lumen of the implant pusher shaft such as shown in FIG. 61.

The proximal end (44) of the implant engagement wire (40) fixedly joins the implant release control mechanism (30) through a chemical mean (for example, an adhesive), a thermal mean (for example, welding), or a mechanical means (for example, crimping). According to one embodiment, as a clinician pulls the implant release control mechanism (30) proximally, the implant engagement wire (40) is retracted proximally. As explained herein, the implant engagement wire (40) can only be extended distally along with the implant pusher shaft (20), the distal end (46) of the implant engagement wire (40) does not extend beyond a predesigned distance relative to the distal end (26) of the implant pusher shaft (20). As the implant pusher shaft (20) remains steady, the implant engagement wire (40) can only be retracted proximally independent of the implant pusher shaft (20) by breaking the engagement between the implant pusher shaft (20) and the implant release control mechanism (30). Without limiting the scope of the present teachings with any particular theory, such a design would prevent an accidental advancement of the implant and avoid any damage to nearby anatomy.

In some embodiments, the implant engagement wire (40) can be made of a metal and/or a plastic material, each chosen from stainless steels, superelastic metals, nickel titanium alloys, shaped memory alloys, shaped memory polymers, polymers, or combinations of one or more of the foregoing. In some embodiments, the implant engagement wire (40) has a general diameter between 0.001" and 0.005". In some embodiments, the implant engagement wire (40) has an enlarged distal end sized so that the implant pusher shaft (20) frictionally engages the implant engagement wire (40).

In other embodiments, a proximal portion and/or a distal portion of the implant engagement wire (40) has a different physical property or is made of a different material. In another embodiment, the implant engagement wire (40) has an enlarged distal portion and is configured for engaging an implant.

Detailed embodiment of the implant release control mechanism will be further explained with reference to FIGS. 4-58. For example, the implant release control mechanism could be of a separate element from the implant pusher shaft, so that various mechanism releasably joins the implant release control mechanism to the proximal end of the implant pusher shaft. For another example, the implant release control mechanism could be of one unit with the implant pusher shaft having a weakened location that allows the implant release control mechanism to break free from the implant pusher shaft.

Figure 3:
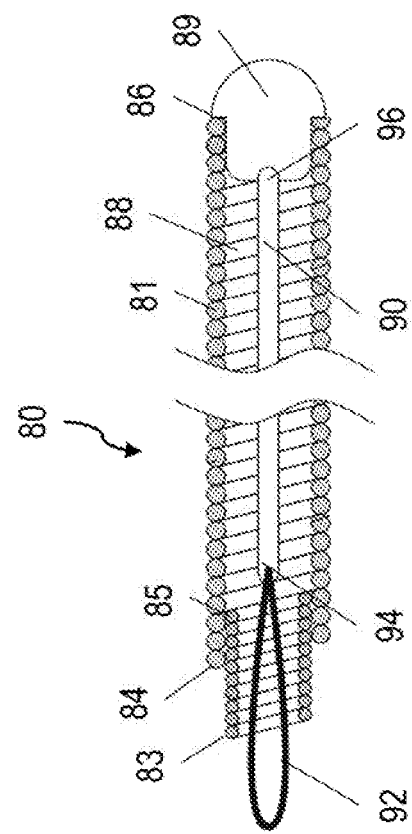
FIG. 3 is a perspective sectional view of an exemplary medical implant in accordance with the present teachings.

FIG. 3 illustrates one coil implant (80) in its elongated delivery profile according to one embodiment. As illustrated, the coil implant (80) has a primary coil body (82) extending from a proximal end (84) to a distal end (86), with an elongated lumen (88) extended from one end to the other end of the coil (82). The distal end (86) of the coil body (82) is fixedly attached to a ball tip (89). An engagement filament (90) is positioned inside the lumen (88) of the primary coil body (82). The distal end (96) of the filament (90) joins with the ball tip (89), and the proximal end (94) of the engagement filament (90) joins an engagement loop (92). In one embodiment, the engagement filament (90) is tensioned, and the engagement loop (92) is not stretchable. FIG. 3 illustrates the engagement filament (90) in a tensioned state where the engagement loop (92) extends beyond the proximal end of the coil implant (80). The engagement loop (92) is configured to engage the coil implant (80) to the delivery system (10) during the implant delivery and deployment. The engagement loop (92) is also configured to be released from the delivery system (10), so that the coil implant (80) is released at a treatment location.

Although now shown here, one skilled in the art should understand that post-implantation, the engagement filament (90) relaxes and both the engagement loop (92) and the engagement filament (90) retracts inside the lumen (88) of the primary coil body (81). The coil implant (80) relaxes from and resumes a pre-configured or randomly-arranged curl profile which fills space at the implantation (such as aneurysm) site. In one embodiment, the engagement filament (90) and its engagement loop (92) is configured to be flexible without imposing any stiffness to the surrounding coil body (82).

In one embodiment, the primary coil body (82) is a continuous coil, or a plurality of coils that connect with one another. In one embodiment, each coil is made of platinum, platinum tungsten alloy, and platinum iridium alloy. In one embodiment, the coil could have a diameter of 0.009" to 0.018". In one embodiment, the ball tip (89) is made of polypropylene and/or another plastic material. In another embodiment, the ball tip (89) is made of a radiopaque material or is incorporated with a radiopaque material. The attachment between the ball tip (89), the distal end (86) of the primary coil body (82), and the distal end (96) of the engagement filament (90) could be achieved by a chemical means (for example, an adhesive), a thermal means (for example, welding), or a mechanical means (for example, friction).

In one embodiment, the engagement filament (90) is a single filar, for example, a polypropylene fiber with a diameter of approximately 0.001". In another embodiment, the coil body (82) is made of multiple filaments, such as two or more filaments in a side-by-side configuration. In one embodiment, the engagement loop (92) is made of a plastic or metal material, for example a nickel titanium alloy. In one embodiment, the engagement loop (92) is made of a filament with a general diameter of approximately 0.001".

In some embodiments, the proximal end of the primary coil body (82) could further attach to a secondary coil (83). As illustrated in FIG. 3, such secondary coil (83) has a smaller diameter than primary coil body (82). For example, such a distal portion (85) of the secondary coil (83) is placed inside a proximal portion of the primary coil body (82). For example, the primary coil body (82) could have a diameter of approximately 0.09" to 0.18", while the secondary coil (83) could have a general diameter of approximately 0.006" to 0.009". Such secondary coil (83) could be a marker band engaged to the distal end of engagement loop (92), and such secondary coil (83) is configured to be positioned inside the primary coil body (81). In one embodiment, the secondary coil (83) could have an interference fit with the primary coil body (81). According to one embodiment, before the implant release control mechanism is actuated to release the implant (80), when a clinician needs to retrieve the implant (80) back inside the delivery system (10), the implant (80) is pulled proximally. In the embodiment where a secondary coil (83) is incorporated, the stress incurring during such proximal pulling would not transfer to be applied to engagement filament (90). One skilled in the art should understand, the incorporation of this secondary coil (83) is merely a design detail for this exemplary embodiment. Implant such as embolic coil for aneurysm could have no secondary coil. Alternatively, the secondary coil could be a marker band. Thus, what has been shown and described here should not be viewed as limit to the scope of this teaching.

Although shown in FIG. 3, the engagement loop (92) joins the engagement filament (90), which in turn engages the distal end (86) of the primary coil body (81) via a ball tip (89), one skilled in the art should understand that the engagement loop (92) could join the proximal end (84) of the primary coil body (81) directly, or the proximal end (85) of the secondary coil (83) directly. Thus the shown exemplary embodiment in FIG. 3 should not limit the scope of the present teaching.

Figure 41:
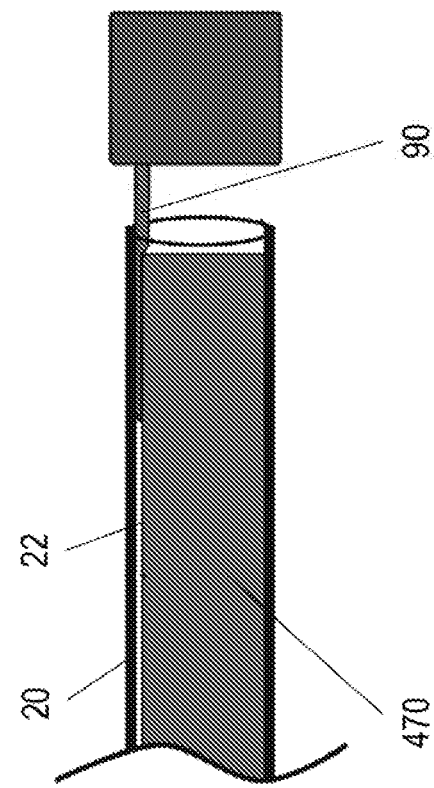
Figure 42:
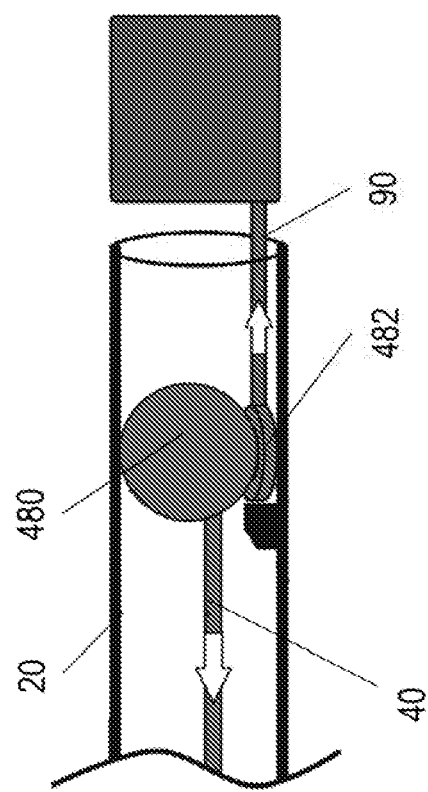
Figure 44:
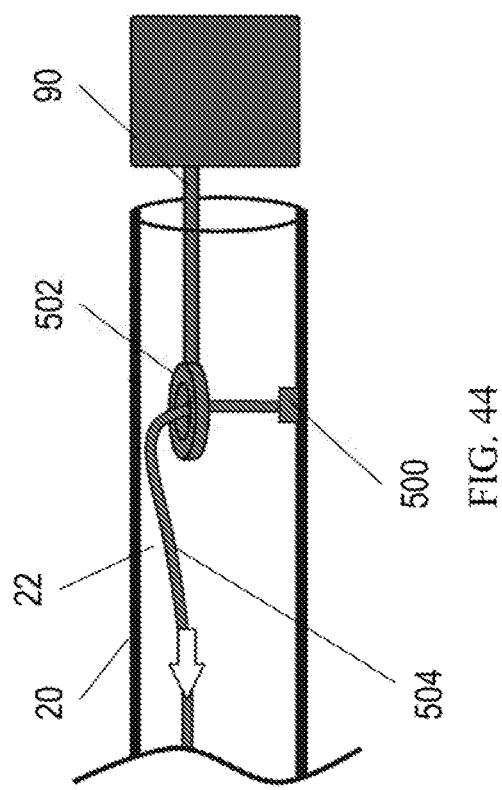
FIGS. 43-45 are perspective views of various exemplary engagement between a delivery system and a medical implant where the engagement wire has a breakable portion in accordance with the present teachings.
Figure 43:
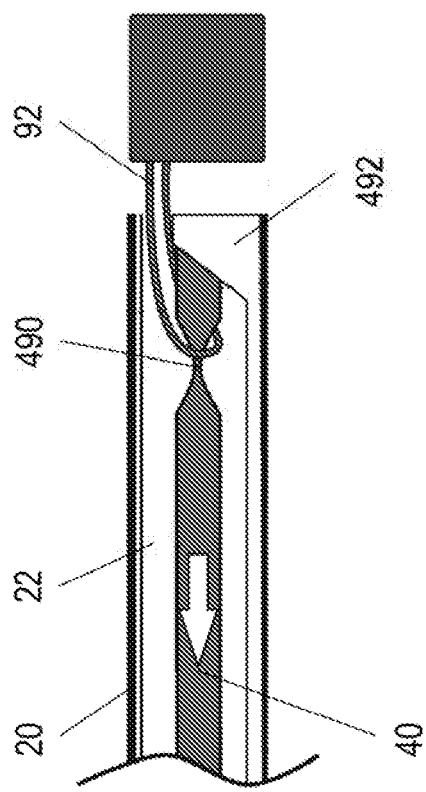
Figure 45:
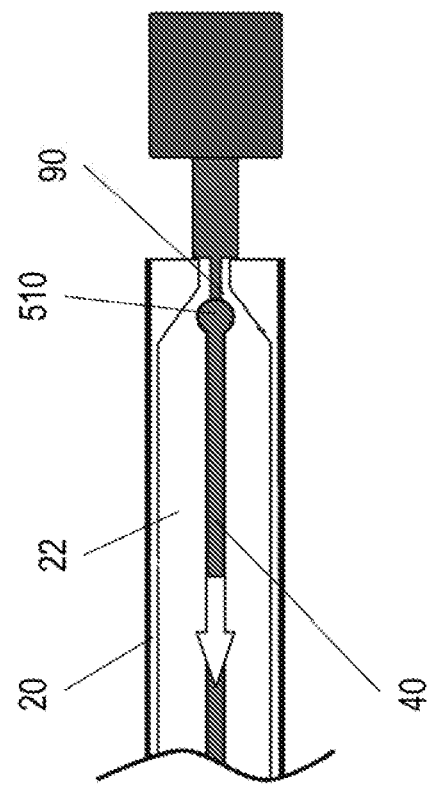

Additionally, FIG. 3 illustrates a coil implant (80) with an engagement loop (92) configured to engage the implant (80) to a delivery system (10), one skilled in the art should understand that other engagement features could also be incorporated to the coil implant (80) in order to achieve the same engagement function. For example, FIGS. 4-19 illustrate a group of wire-loop engagement feature between the implant and delivery system, FIGS. 20-37 illustrate a group that the enlarged proximal end of the engagement filament being captured by the engagement wire, the implant pusher shaft, or, a combination of both; FIGS. 38-39 illustrate a group that the collapsible proximal end of the engagement filament being captured by the engagement wire, the implant pusher shaft, or, a combination of both; FIGS. 40-42 illustrate a group of exemplary embodiments where the proximal portion of the engagement filament frictionally engages to the engagement wire and/or the implant pusher shaft. FIGS. 43-45 illustrate a group exemplary embodiment where the engagement breaks at a breakable portion in order to release the implant. FIGS. 46-52 illustrate a group of bracket engagement feature between the implant and delivery system. FIGS. 53-58 illustrate various other engagement features between the implant and delivery system. One skilled in the art should understand that other engagement features are also within the scope of present teachings.

FIGS. 4-19 illustrate various engagement mechanisms between a coil implant with an engagement loop and a delivery system having an engagement wire for implant delivery and deployment according to some embodiments of present teachings. To simplify description herein, the proximal portion of the implant pusher shaft, the motion of the implant release control mechanism and the shape transformation of the coil implant will not be included when describing such engagement mechanism.

According to some embodiments of the present teachings, FIGS. 4-13 illustrate various exemplary embodiments of the engagement wire-interface-engagement loop mechanism. As illustrated, the engagement loop of the implant extends proximally over an interface at the distal end of the implant pusher shaft, and an engagement wire extends distally securing the engagement loop-interface engagement, and further extends distally either meet or extend over the interface and thereby joins the implant to the delivery system.

Now referring to FIG. 4A, the interface (100) at the distal end (26) of the implant pusher shaft (20) is a cross pin (102) that joins two opposing fingers (104a, 104b) at the distal end (26) of the implant pusher shaft (20). As shown, the distal end (26) of the implant pusher shaft (20) has two fingers (104a, 104b), each extending distally. A cross pin (102) joins the distal ends of the two fingers (104a, 104b). Although FIG. 4A discloses those two fingers (104a, 104b) as directly opposing each other across the axial center of the implant pusher shaft (20), one skilled in the art should understand that modifications could be made according to the treatment purpose and location. Additionally, FIG. 4A illustrates that the cross pin (102) joins two fingers (104a, 104b) at their distal tips, and one skilled in the art should understand that the location where the cross pin (102) joins the fingers can vary according to the need during the manufacturing process. Thus, the specific embodiments disclosed herein should not be viewed as limiting to the scope of the present teachings. In some embodiments, the length of the fingers (104a, 104b) ranges from 0.008" to 0.04". In some embodiments, the diameter of the cross pin (102) ranges from 0.001" to 0.002".

According to one embodiment, (not shown in this figure), as the implant release control mechanism (30) engages the proximal end (24) of the implant pusher shaft (20), the distal end (46) of the implant engagement wire (40) extends beyond the cross pin (102) of the implant pusher shaft (20). As the implant release control mechanism (30) is retracted proximally, the distal end (46) of the implant engagement wire (40) moves proximally over the cross pin (102), and withdrawn inside the elongated lumen (22) of the implant pusher shaft (20).

Now referring to FIG. 4A, according to one embodiment, a coil implant (80) engages to a delivery system (10). FIG. 4A illustrates that the distal portion of the delivery system (10) is engaged with the proximal portion of the coil implant (80). Although not shown in FIG. 4A, the engagement filament (90) is tensioned, and the coil implant (80) is in its elongated delivery profile. As shown in FIG. 4A, the engagement loop (92) extends beyond the proximal end of the coil implant (80), further extends proximally beyond the cross pin (102) at the distal end (26) of the implant pusher shaft (20). The distal end (46) of the implant engagement wire (40) extends through the center of the engagement loop (92), and further extends distally over the cross pin (102) into the lumen (22) of the coil implant (80). As shown in FIG. 4A, engagement loop (92) extend over one side of the cross pin (102), and the engagement wire (40) extends over the opposing side of the cross pin (102), such that the cross pin (102) is sandwiched in between the engagement loop (92) and engagement wire (40). As the implant engagement wire (40) remains steady, the distal movement of the engagement loop (92) is stopped by the cross pin (102). This may allow the coil implant (80) to be securely engaged to the delivery system (10). During the implant delivery and deployment, as the clinician advances the delivery system (10) distally, the coil implant (80) is pushed distally, for example, by cross pin (102) pushing onto the proximal end of the coil implant (80). In addition, the engagement between the delivery system (10) and the coil implant (80) also allows a rotational movement of the delivery system (10) to be transferred to the coil implant (80).

Although FIG. 4A illustrates a gap between the cross pin (102) of the implant pusher shaft (20) and the proximal end of the coil implant (80), those skilled in the art should understand that during the implant's distal advancement, there will be no gap. What's shown in FIG. 4A is a merely an illustration for the sole purpose of explaining various embodiments of the present teachings.

As illustrated in FIG. 4A, the engagement loop (92) extends proximally over one side of the cross pin (102), and the implant engagement wire (40) extends distally through the center of the engagement loop (92) and over another side of the cross pin (102). In order for the engagement loop (92) to hoop over the cross pin (102), as shown in FIG. 4A as well some figures further down, the engagement loop (92) bends away from the longitudinal axis of the implant pusher shaft (20) to a degree "0". Although an approximately 90° angle is shown in FIG. 4A, one skilled in the art should understand that any degree could be possible as long as an attachment is achieved between the delivery system (10) and the coil implant (80). In some embodiment, the distal portion of the engagement wire (40) could be bent to a degree while the engagement loop (92) remain its original profile.

Once a clinician is satisfied with the positioning and deployment of the coil implant (80), he/she can start the implant releasement process. The implant engagement wire (40) is withdrawn proximally out of the engagement loop (92) center while freeing the engagement loop (92) of the coil implant (80) as shown in FIG. 4B. Once freed, the engagement filament (90) of the coil implant (80) relaxes and resume its original non-tensioned profile, and the engagement filament (90) and its engagement loop (92) is withdrawn inside the lumen of the coils. In some embodiments, the coil implant (80) curls and fills the treatment space.

Figure 4C:
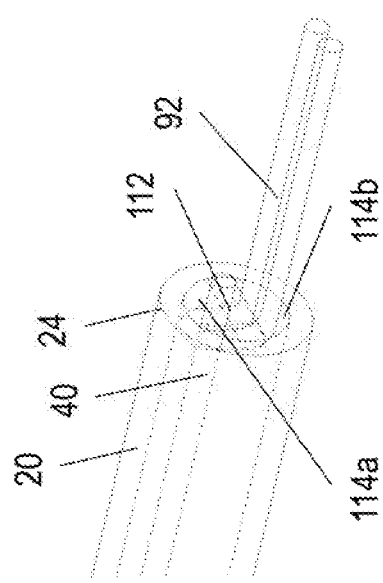

FIG. 4C illustrates a variation to the exemplary embodiment shown in FIGS. 4A-4B. As shown in FIG. 4C, according to one embodiment, instead of the cross pin (112) joining two fingers, the cross pin (112) could directly joins two small opposing portions of the distal end (26) of the implant pusher shaft (20) and thereby dividing the distal opening of the implant pusher shaft (20) into two openings (114a, 114b). As shown in FIG. 4C, similar to what has been disclosed with reference to FIG. 4B, the engagement loop (92) extends proximally from one opening (114b) into the lumen (22) of the implant pusher shaft (20) and is then captured by the engagement wire (40). The engagement wire (40) extends distally over the engagement loop (92) center and further beyond the cross pin (112) through the second opening (114a).

Although a cross pin (102, 112) is being described herein with reference to FIGS. 4A-4C, one skilled in the art should understand that other features could be incorporated in order to achieve the same engagement setup. For example, the distal end portion of the implant pusher shaft (20) could have a dual lumen feature, where one allows the engagement loop (92) to extend proximally in, and the other allows the engagement wire (40) to extend distally out.

Figure 5A:
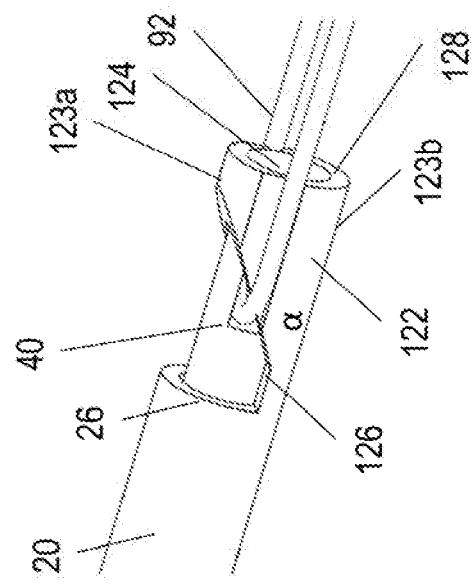
Figure 5B:
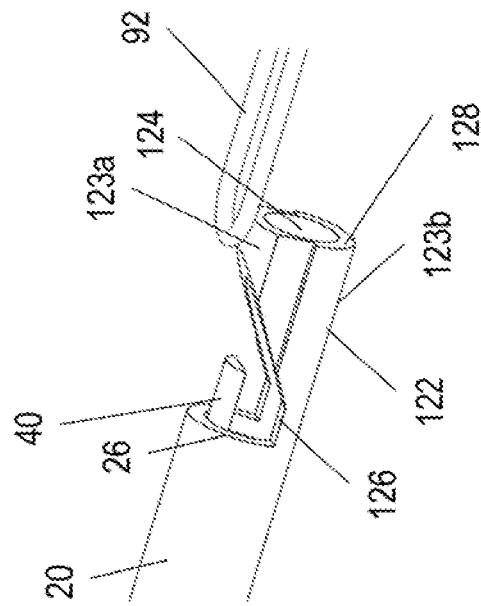

FIGS. 5A-5B illustrate an external ramp shaped interface at the distal end (26) of the implant pusher shaft (20). As shown in FIG. 5A, the distal end (26) of the implant pusher shaft (20) has a ramp (122) feature that extend from a partially cylindrical surface of the implant pusher shaft (20) distally. Such ramp (122) also has an axial lumen (124) that allows the engagement wire (40) to extend through. The ramp (122) has a distal end surface (128) perpendicular to the longitudinal axis of the implant pusher shaft (20). The ramp (122) also has a proximal surface (126) that is angled from the longitudinal axis of the implant pusher shaft (20). The curved tubular surface of the ramp has a relatively shorter side (123a), and a relatively longer side (123b). A portion of the curved tubular surface that is part of the ramp (122) joins the distal end (26) of the implant pusher shaft (20). One skilled in the art should understand that such ramp (122) could be constructed by removing material from the distal portion (29) of the implant pusher shaft (20), for example, by removing the partial tubular surface of the distal portion (29) of the implant pusher shaft (20). The angle "α" of the proximal surface of the ramp is configured to allow engagement loop (92) to smoothly slide off the ramp (122). Thus, such angle "α" could vary according to the specific implant design, treatment location and etc.

Figure 5C:
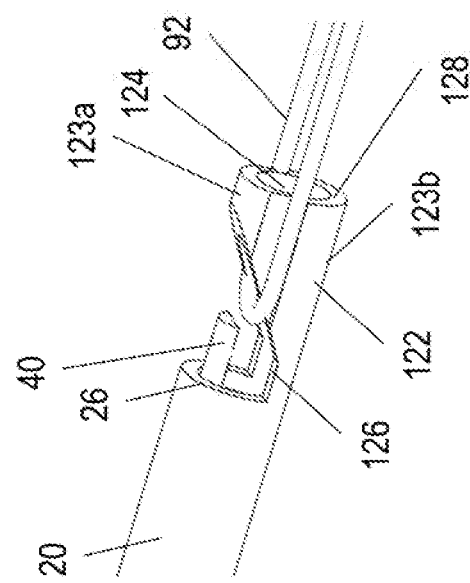

FIG. 5A shows that the engagement loop (92) hoops proximally over the ramp (122), so that the loop circles around the ramp (122). The engagement wire (40) extends distally above the engagement loop (92) and through the axial lumen (124) of the ramp (122) thereby prevent engagement loop (92) from unhook from the ramp (122). As shown in the figure, portion of the engagement loop (92) is sandwiched between the engagement wire (40) and the ramp (122) interface. The implant therefore engages to the delivery system (10) through this engagement wire-interface (i.e. ramp (122))—engagement loop mechanism. FIG. 5B illustrates the disengagement of the implant from the delivery system (10). As shown, the engagement wire (40) has withdrew proximally out of the axial lumen (124) of the ramp (122). Although the engagement loop (92) remains looped over the ramp (122), a clinician could further withdraw the implant pusher shaft (20) proximally, and thereby allowing the engagement loop (92) to slide along the proximal angled face (126) of the ramp (122). As such, the implant (80) is then released from the delivery system (10) such as shown in FIG. 5C. One skilled in the art should also understand that as the tensioned engagement filament (90) of the implant (80) relaxes and retracts, the engagement loop (92) could also be pulled distally by such distal force, and release itself from the ramp (122).

Figure 6:
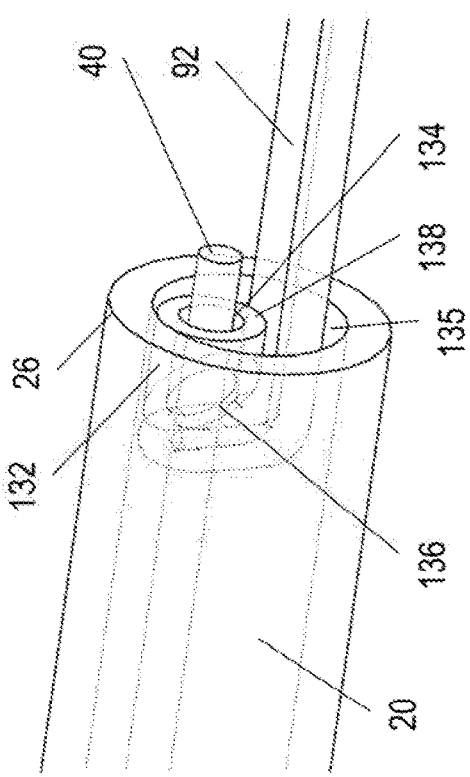

FIG. 6 illustrates an internal ramp (132) shaped interface (130) at the distal end (26) of the implant pusher shaft (20). As shown in FIG. 6, the distal end (26) of the implant pusher shaft (20) has an internal ramp feature with the distal end of the ramp (132) aligns with the distal end (26) of the implant pusher shaft (20). The ramp (132) also has a proximal surface (136) that is angled from the longitudinal axis of the implant pusher shaft (20). The curved tubular surface of the ramp (132) also has a relatively shorter side, and a relatively longer side. A portion of the curved tubular surface of the ramp (132) joins a portion of the internal luminal surface near the distal end (26) of the implant pusher shaft (20). The internal ramp (132) could also be described as a sleeve with a through lumen (134). The overall size of the sleeve/ramp (132) is smaller than overall size of the internal lumen of the distal end portion of the implant pusher shaft (20), while part of the distal opening on the implant pusher shaft lumen remains open. As shown in FIG. 6, the engagement loop (92) extends proximally through remaining opening (135) of the implant pusher shaft (20) into the axial lumen and is captured by the engagement wire (40). The engagement wire (40) extends distally through the center of the engagement loop (92) and further into the lumen (134) of the sleeve, thereby securing the coil implant (80) to the delivery system (10). By retracting the engagement wire (40), engagement loop (92) 92 is then released.

Figure 7:
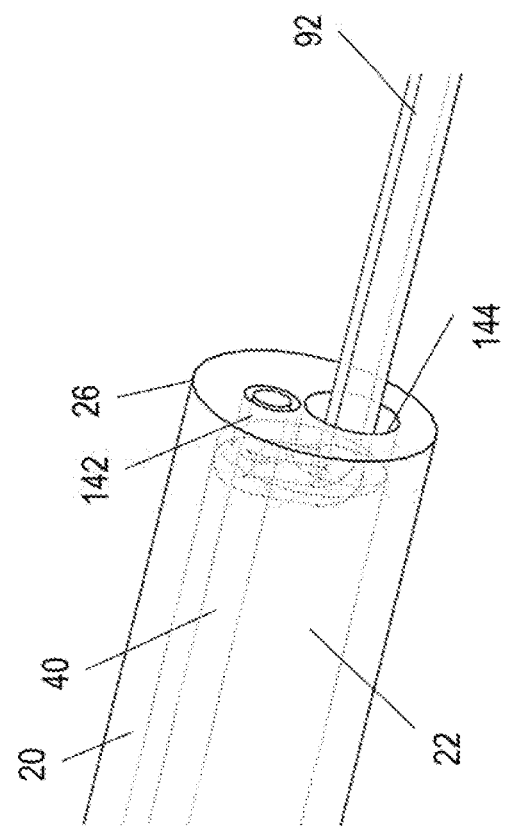

FIG. 7 illustrates another exemplary of engagement wire-interface-engagement loop mechanism. As shown in FIG. 7, the distal end (26) of the implant pusher shaft (20) an opening (144) that communicates with the axial lumen (22) of the implant pusher shaft (20), but generally smaller than the overall diameter of the lumen (22). The distal end (26) of the implant pusher shaft (20) also has an internal recess (142) next to the small opening. The recess (142) also communicates with the axial lumen (22) of the implant pusher shaft (20), and sized and shaped to receive the distal end (46) of the engagement wire (40). During implant delivery, the engagement loop (92) extends proximally, through the opening (144) into the axial lumen (22) of the implant pusher shaft (20). The engagement wire (40) extends distally through the engagement loop (92) and then further into the internal recess (142) the distal end (26) of the implant pusher shaft (20).

Figure 8B:
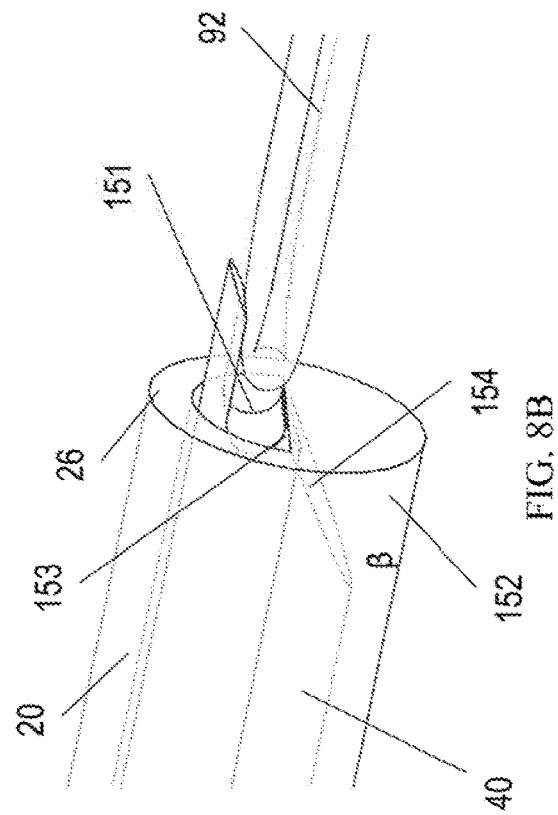
Figure 8A:
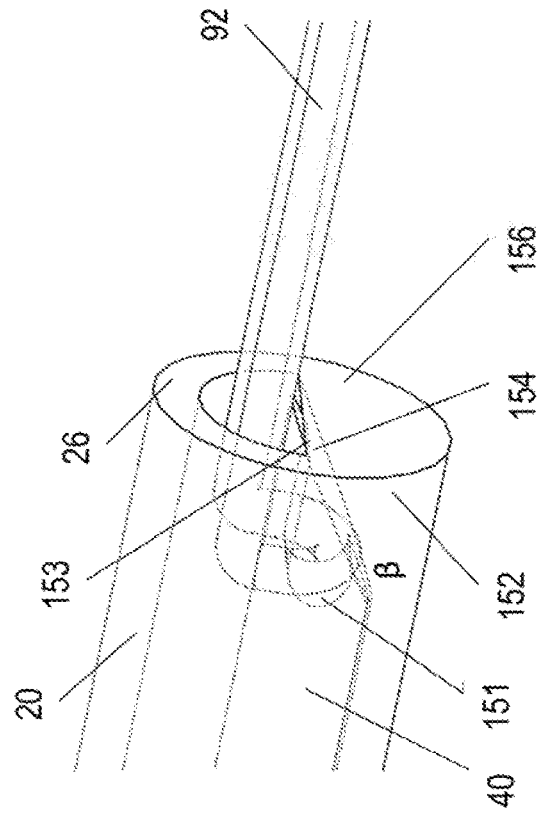

FIGS. 8A-8B illustrate another internal ramp shaped interface at the distal end (26) of the implant pusher shaft (20). As illustrated in FIG. 8A, a ramp (152) is constructed inside a distal portion (29) of the implant pusher shaft (20), and it partially blocks the distal luminal opening of the implant pusher shaft (20). The ramp (152) has a distal end surface (156) aligned with the distal end surface of the implant pusher shaft (20), perpendicular to the longitudinal axial of the implant pusher shaft (20). The ramp (152) has a proximal angled surface (154). The ramp (152) joins the distal portion (29) of the inner luminal surface of the implant pusher shaft (20) such that the proximal angled surface (154) forms an acute angle β" with the longitudinal axis of the implant pusher shaft (20). Similar to what has been described above, such an angle "β" could vary according to the specific requirements of each treatment. In one embodiment, such ramp (152) could be a separate component fixedly attaches to inner luminal surface of the implant pusher shaft (20). One skilled in the art should understand that other embodiments could also be used to build such ramp (152).

FIG. 8A further illustrates the engagement loop (92) that extends proximally above the ramp (152), and into the luminal opening of the implant pusher shaft (20). As shown in the figure, the very proximal portion of the engagement wire (40) bends toward the ramp (152). The engagement wire (40) extends distally into the center of the engagement loop (92). The distal end (46) of the engagement wire (40) joins the proximal angled surface (154) of the ramp (152) and thereby secures the engagement loop (92). As shown in the figures, the very proximal portion of the engagement loop (92) is sandwiched in between the engagement wire (40) and the ramp (152).

According to one embodiment, as illustrated in FIG. 8B, the distal end of engagement wire (40) could include a recess (151) which is configured to receive the proximal portion of the engagement loop (92). In another embodiment, as illustrated in FIGS. 8A-8B, the distal end of the engagement wire (40) could also have an angled surface (153) that is configured to match the proximal angle surface (154) of the ramp (152). So that, when the engagement wire (40) is pushed against the ramp (152), the distal end surface (153) of the engagement wire (40) aligns the angled proximal surface (154) of the ramp (152). One skilled in the art should understand what has been illustrated in FIGS. 8A-8B is merely one exemplary embodiment, and other design feature could also be incorporated to the engagement wire (40) to securely join the engagement loop (92) to the delivery system (10). As illustrated in FIGS. 8A-8B, the implant engages to the delivery system (10) through this engagement wire-interface (i.e. ramp (152))-engagement loop mechanism. Similarly, by retracting the engagement wire (40), the engagement loop (92) is then released.

FIG. 9 illustrates a variation to the exemplary embodiment shown in FIGS. 8A-8B. As shown in FIG. 9, the engagement wire (40) has an enlarged distal end (165) which is shaped and sized to match the shape and size of the proximal angled surface (164) of the internal ramp (162) interface. During implant delivery and deployment, the enlarged distal portion (165) of the engagement wire (40) meets the proximal angled surface (165) of the internal ramp interface, and thereby limiting the distal movement of the engagement loop (92), and securely engages the implant. Similarly, by retracting the engagement wire (40), engagement loop (92) is then released.

FIG. 10 illustrates another variation to the exemplary embodiment shown in FIGS. 8A-8B. As shown in FIG. 10, the internal ramp interface (172) has a through lumen (176) extending from its proximal angled surface (174) to its distal surface (178). Similar to what has been described in FIGS. 8A-8B, the engagement loop (92) extends proximally above the ramp (172), and into the luminal opening of the implant pusher shaft (20) and is captured by the engagement wire (40). The engagement wire (40) extends distally first through the center of the engagement loop (92) and then through the lumen (176) of the internal ramp interface (170). The engagement loop (92) is captured by the between the engagement wire (40) and the internal ramp interface (172). By retracting the engagement wire (40), the engagement loop (92) is then released.

FIG. 11 illustrates another exemplary embodiment of the interface embodiment at the distal end (26) of the implant pusher shaft (20). As shown in the figure, a radially inward bending tab (180) is attached to the inner luminal wall of a distal portion (29) of the implant pusher shaft (20). One end of the tab (180) fixes to the implant pusher shaft (20), while the other end (184) of the tab (180) is free and within the axial lumen (22) of the implant pusher shaft (20). The free end (184) of the tab (180) is spaced from the inner luminal wall, so that the engagement wire (40) could extend through. The tab (180) has an opening (182) allowing the engagement wire (40) to extend through. In one embodiment, the tab (180) could have a curved geometry shown in FIG. 11. Other shape, form, and configuration could also be adopted for the tab (180) design so long as the intended function are satisfied. The engagement loop (92) extends proximally over the free end (184) of the tab (180) and is then captured by the engagement wire (40). The engagement wire (40) extends distally through the center of the engagement loop (92) and then through the tab opening (182). The engagement loop (92) is captured by the interface between the engagement wire (40) and the tab (154). By retracting the engagement wire (40), the engagement loop (92) is then released.

Figure 12B:
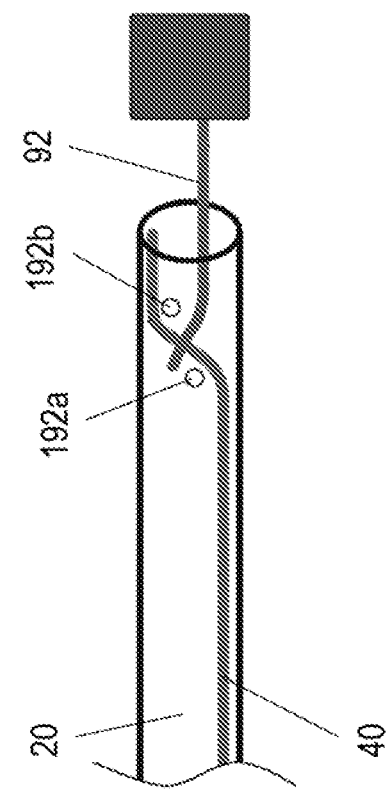
Figure 12C:
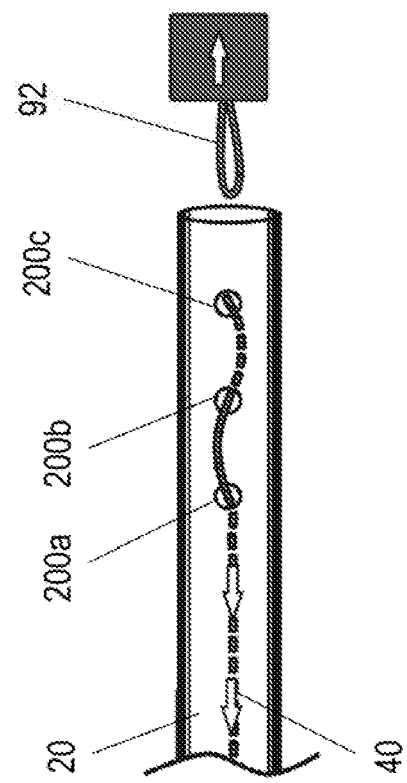

FIGS. 12A-12B illustrate another exemplary embodiment of the interface embodiment at the distal end (26) of the implant pusher shaft (20). FIG. 12A and FIG. 12B are two different view of the same embodiment. As shown in the figures, the two cross pins (190a, 190b) join the opposite luminal wall inside a distal portion (29) of the implant pusher shaft (20). As shown in the figures, the two cross pins (190a, 190b) are configured to be parallel to each other, and are generally perpendicular to the longitudinal axis of the implant pusher shaft (20). In one embodiment, the two cross pin s (190a, 190b) all cross the center axis of the implant pusher shaft (20), as shown in FIGS. 12A-12B. In another embodiment, none of the two cross pins (190a, 190b) cross the center axis of the implant pusher shaft (20), as shown in FIG. 12C. In one embodiment, there is a lateral distance in between the two cross pins (192a, 192b) and there is no vertical distance in between the two cross pins (190a, 190b), as shown in FIGS. 12A-12B. In another embodiment, they are both lateral and vertical distanced between the two cross pins (192a, 192b), as shown in FIG. 12C. As shown in FIGS. 12A-12C, the engagement loop (92) extends proximally inside the axial lumen (22) of the implant pusher shaft (20), over a first side of the distal cross pin (190b, 192b), then is captured by the engagement wire (40). The engagement wire (40) extends distally first over the same side of the proximal cross pin (190a, 192a) (as the side which the engagement loop (92) extends over the distal cross pin (190b, 192b)), then through the center of the engagement loop (92), and finally over the opposite side of the distal cross pin (190b, 192b) (as to the side which the engagement loop (92) extends over the distal cross pin (190b, 192b)). The engagement loop (92) is captured by the interface between the engagement wire (40) and two cross pins. By retracting the engagement wire (40), engagement loop (92) is then released.

Figure 13A:
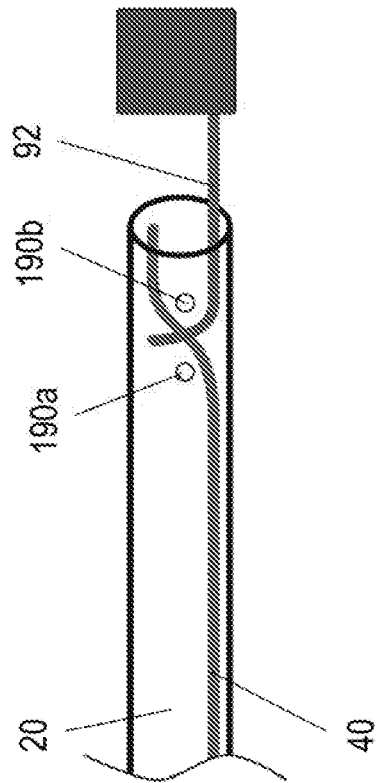
Figure 13B:
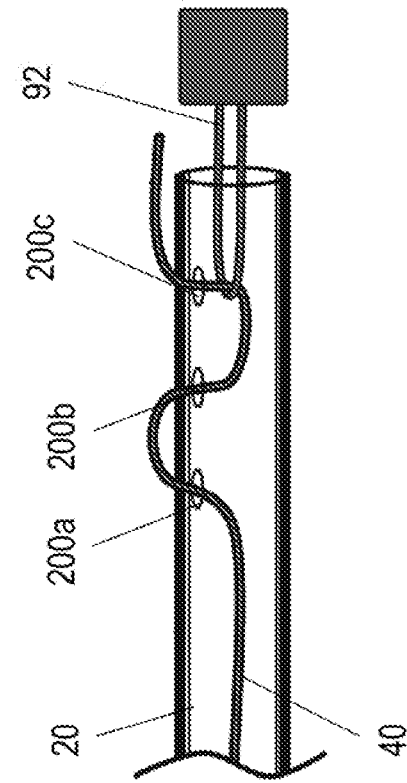

FIGS. 13A-13B illustrate another exemplary embodiment of the engagement wire-interface-engagement loop mechanism. FIG. 13A illustrates a distal portion (29) of the implant pusher shaft (20) with three openings (200a, 200b, 200c) on the luminal wall extending from the inner lumen (22) of the implant pusher shaft (20) to the outside. In one embodiment, the size and shape of the opening is configured to allow the engagement wire (40) to thread through. As shown in FIG. 13A, the distal portion of the engagement wire (40) extends distally from the inner lumen (22) of the implant pusher shaft lumen, threads through the proximal opening (200a) reaching the outside of the implant pusher shaft (20), further extend distally to thread through the middle opening (200b) coming back to the inner lumen (22) of the implant pusher shaft (20), continue extends distally capturing the engagement loop (92), then threads through the distal opening (200c) again to reach the outside of the implant pusher shaft (20), and finally extends further distally. A part of the engagement loop (92) is captured inside the implant pusher shaft lumen. The engagement loop (92) is captured by the interface between the engagement wire (40) and luminal wall of the implant pusher shaft (20) in between the distal (200c) and middle (200b) openings. By retracting the engagement wire (40), engagement loop (92) is then released as shown in FIG. 13B.

In one embodiment, the spacing between each of the two adjacent openings are the same. In another embodiment, spacing between each of the two adjacent opening can vary. In one embodiment, the three openings line up in a straight line which could be parallel or at an angle to the longitudinal axis of the implant pusher shaft (20). In another embodiment, the three openings (200*a*, 200*b*, 200*c*) do not line up in a straight line, but are instead spread out along the tubular surface. The placement pattern of the three openings (200*a*, 200*b*, 200*c*) could change the retracting force required to release the implant. For example, in the embodiments where three opening are lined up in a straight line that is at an angle to the longitudinal axis of the implant pusher shaft (20), the force required to release the implant is increased comparing the configuration shown in FIG. 13A where the three openings (200*a*, 200*b*, 200*c*) are lined up in a straight line that is parallel to the longitudinal axis of the implant pusher shaft (20). In one embodiment, the size and shape of the three openings (200*a*, 200*b*, and 200*c*) are the same. In another embodiment, the size and shape of the three openings (200*a*, 200*b*, and 200*c*) vary from each other. Although three opening are illustrated in FIGS. 13A-13B, one skilled in the art should understand that two, four, six, or more openings could also be incorporated to accomplish the purpose.

Figure 14:
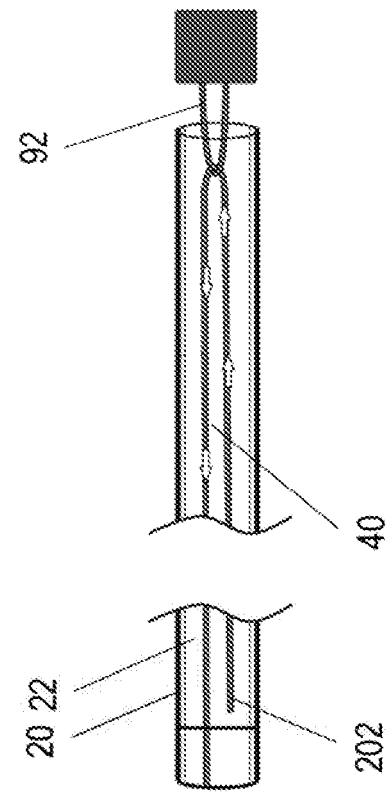
Figure 15:
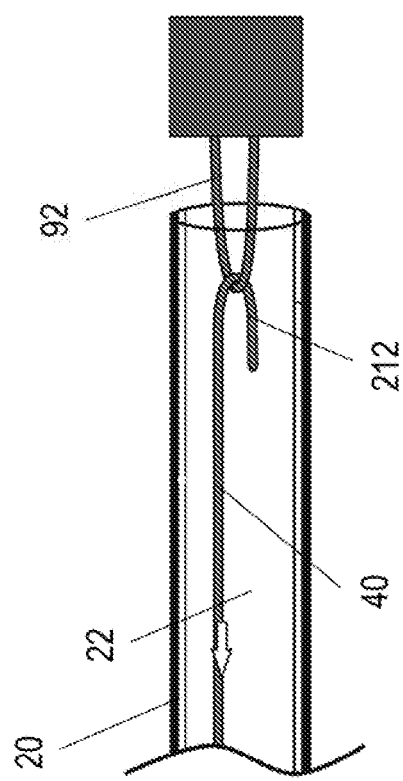
Figure 16:
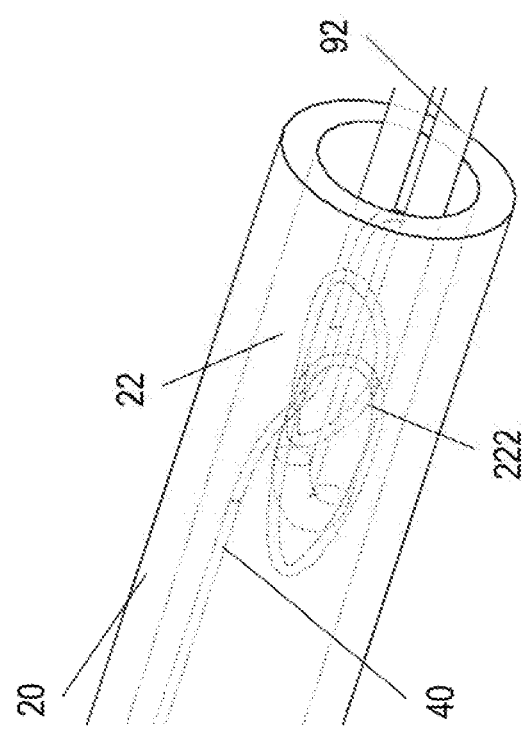

FIGS. 14-16 illustrate another engagement mechanism between the delivery system and the implant, where the implant attaches to the delivery system through a wire-engagement loop mechanism. As illustrated, the engagement loop of the implant extends proximally into the axial lumen of a distal portion of the implant pusher shaft, and then is directly captured by the engagement wire. Similar to what has been described in reference to FIGS. 4-13, by retracting the engagement wire, the engagement loop is then released.

FIG. 14 illustrates one exemplary embodiment of the engagement wire (40)-engagement loop (92) mechanism. As shown in FIG. 14, an engagement wire (40) extends from the implant release control mechanism (30) distally, captures the engagement loop (92), then turns back and continues to extend proximally toward the implant release control mechanism (30). Same as describe above in reference to FIG. 1, one end of the engagement wire (40) fixedly joins the implant release control mechanism (30). As shown in FIG. 14, the free end (202) of the engagement wire (40) terminates either within the implant release control mechanism (30) (not shown), or at a place within the implant pusher shaft lumen that is proximal to the implant release control mechanism (30) as shown in FIG. 14. The engagement loop (92) is captured by the engagement wire (40) directly. In one embodiment, a part of the engagement loop (92) is captured inside the implant pusher shaft lumen. Similarly, by retracting the engagement wire (40) at its fixed end, the free end (202) of the engagement wire (40) travels distally, passes through the loop (92) and then releasing the engagement loop (92).

In one embodiment, the engagement wire (40) is configured so its free end (202) frictionally engages the inner lumen (22) of the implant pusher shaft (20). This frictional engagement can be configured to prevent undesired translation of engagement wire (40). Alternatively, the free end (202) of engagement wire (40) can be releasably attached to a portion of the implant pusher shaft (20) or to the implant release control mechanism (30) to prevent any accidental release of the implant.

FIG. 15 illustrates a variation to the exemplary embodiment shown in FIG. 14. As shown in FIG. 15, instead of a long engagement wire (40) that extends nearly twice the length of the implant pusher shaft (20), in this exemplary embodiment, a distal portion of the engagement wire (40) includes a hook (212). Such hook passes through the engagement loop (92) and thereby engages the implant to the delivery system (10). According to some embodiment, the hook (212) portion has a resiliently biased material and/or configuration such that a retraction of the engagement wire (40) straightens the hook and allows the free end of the hook (212) pass the engagement loop (92).

FIG. 16 illustrates another variation to the exemplary embodiment shown in FIG. 14. As shown in FIG. 16, a distal portion of the engagement wire (40) ties to the engagement loop (92), forming an exploding knot (222). The term "exploding knot" means a knot that can untie itself with one tug of one end of the string, leaving no tangle. During delivery and deployment, such exploding knot (222) secures the implant to the delivery system (10). When released, the engagement wire (40) is pulled proximally, allowing the exploding knot (222) to untie itself, thereby releasing the implant. In some embodiments, for the ease of creating such exploding knot (222), the distal portion of the engagement loop (92) have a different shape, size, physical property such as stiffness, and/or material construct than proximal portion of the engagement loop (92).

Figure 17:
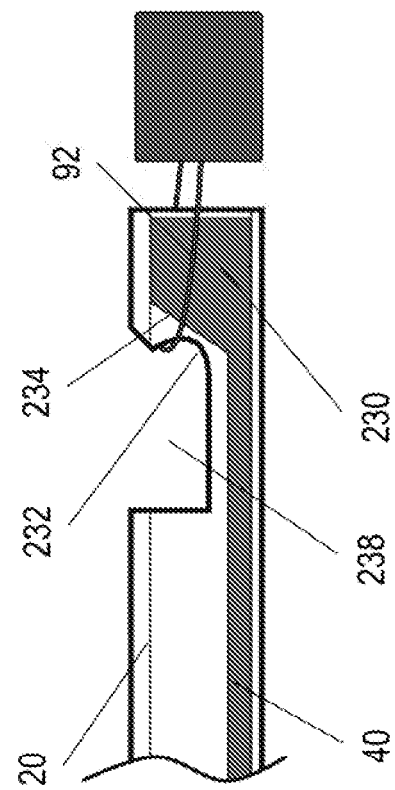
Figure 18A:
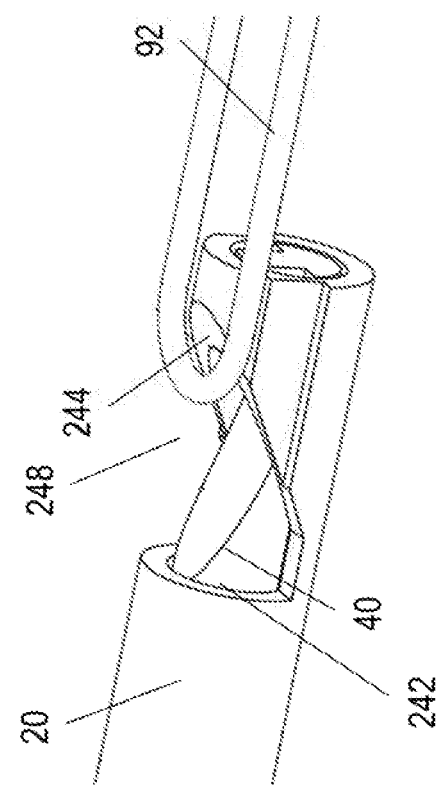

FIGS. 17-18 illustrate another engagement mechanism between the delivery system and the implant, where the implant attaches to the implant pusher shaft through a hook-engagement loop mechanism. As illustrated, the engagement loop of the implant extends proximally and is captured by a hook configuration.

FIG. 17 illustrates one exemplary embodiment of the hook-engagement loop mechanism. As shown in FIG. 17, a distal portion (29) of the implant pusher shaft (20) has a side opening (238), with the portion of the implant pusher shaft (20) distal to the opening, forming a hook (232) like configuration. Such hook (232) is configured to receive the engagement loop (92) of the implant. The distal end of the engagement wire (40) has a ramp (230). Such ramp (230) has an angled proximal surface. During implant delivery and deployment, the ramp (230) at the distal end of the engagement wire (40) is positioned inside the axial lumen (22) of the implant pusher shaft (20) distal to the side opening (238), and the engagement loop (92) wraps over the hook (232) with such tension allowing the implant pusher shaft (20) apply distal movement force to the implant while still secures the engagement between the implant the delivery system (10). According to some embodiments, the hook (232) has a shape, size and configured to prevent accidental release of the engagement loop (92) during delivery and deployment. During release, the engagement wire (40) is pulled proximally, as the ramp (230) at the distal end of the engagement wire (40) travels proximally, pulling on the engagement loop (92). The angled surface (234) of the ramp (230) is configured to allow the engagement loop (92) to slide upward into freedom, and thereby release the implant (80).

FIG. 18 illustrates another exemplary embodiment of the hook-engagement loop mechanism. As shown in FIG. 18, a distal portion (29) of the implant pusher shaft (20) has a side opening (248), with the portion of the implant pusher shaft (20) distal to the opening (248), forming an angled surface (244) toward the side opening (248). The distal end of the engagement wire (40) has a hook (242) shaped profile, as covered by the implant pusher shaft in FIG. 18. Such hook (242) is configured to receive the engagement loop (92) of the implant. According to some embodiments, when the engagement wire (40) is pulled proximally, the free end of the hook (242) meets the luminal wall proximal to the side opening (248) of the implant pusher shaft (20) and traps the captured engagement loop (92). In another embodiment, when the engagement wire (40) is pulled proximally, the hook (242) tightly fits inside the axial lumen (22) of the implant pusher shaft (20), and thereby traps the captured engagement loop (92).

Figure 18B:
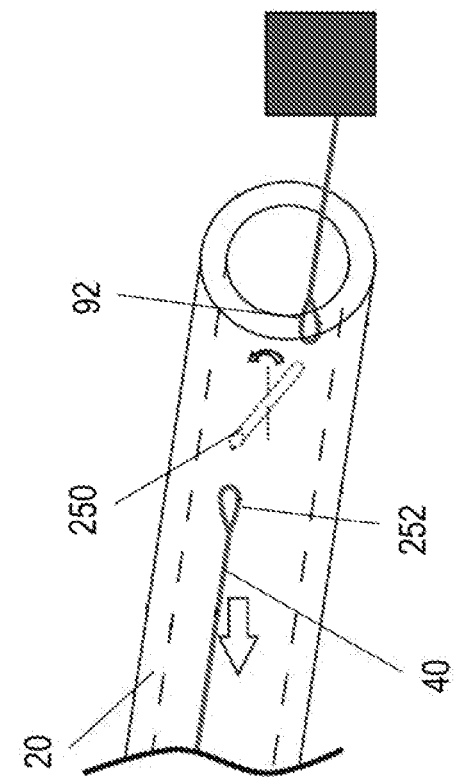

During the implant delivery and deployment, the engagement loop (92), loops over the portion of the implant pusher shaft (20) distal to the side opening (248), the distal hook (242) of the engagement wire (40) captures the engagement loop (92), and the engagement wire (40) is pulled proximally trapping the captured engagement loop (92). At this state, the implant pusher shaft (20) could push the implant distally while still securing the engagement between the implant and the delivery system (10). During release, the engagement wire (40) extends distally into the axial lumen (22) of the implant pusher shaft (20) distal to the side opening (248). As the distal hook (242) of the engagement wire (40) positions inside the implant pusher shaft lumen, the engagement loop (92) remains looped over the portion of the implant pusher shaft (20) distal to the side opening (248). The angled surface (244) is configured to allow the engagement loop (92) to slide upward into freedom, and thereby release the implant, such as shown in FIG. 18B.

Figure 19A:
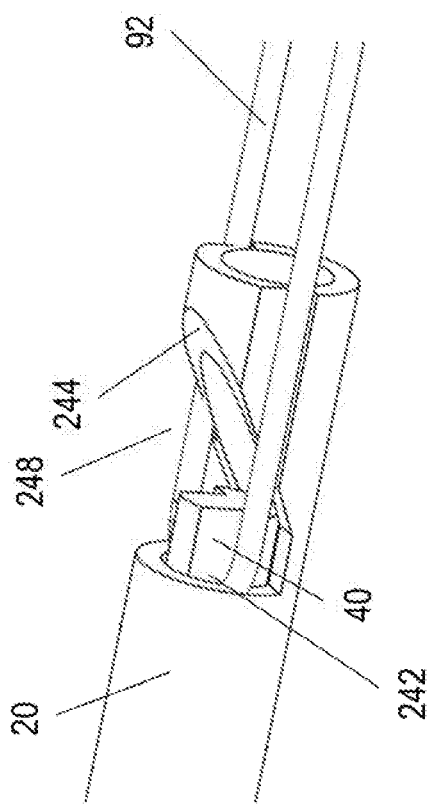
Figure 19B:
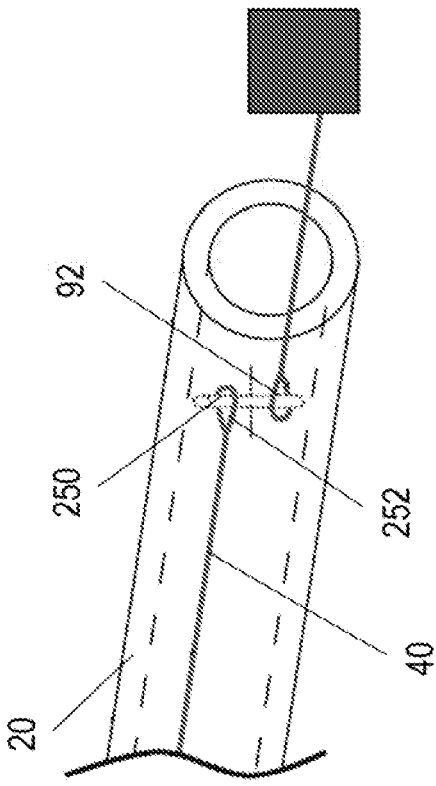

FIGS. 19A-19B illustrate another interface embodiment at the distal end portion of the implant pusher shaft (20). FIG. 19A illustrates a rotatable pin (250) placed inside the implant pusher shaft lumen. In one embodiment, the pin (250) is configured to rotate at its center. The distal end of the engagement wire (40) also has a loop (252). To engagement an implant to the delivery system (10), the engagement loop (92) of the engagement filament (90) loops over one side of the pin (250), the loop (252) of the engagement wire (40) loops over another side of the pin (250) across the rotation center as shown in FIG. 19A. To release the implant from the delivery system (10), the engagement wire (40) retracts proximally, causing the pin (250) to rotate about its center. When the pin (250) approaching the orientation of the longitudinal axis of the implant pusher shaft (20) as shown in FIG. 19B, the engagement loop (92) of the engagement filament (90) is released from the pin (250).

FIGS. 20-36 illustrate various engagement mechanisms between an implant and the delivery system, where the implant has a non-deformable enlarged proximal end of the engagement filament being captured by the delivery system. As later shown in these embodiments, the implant does not have an engagement loop at the proximal end of the engagement filament. Instead, the implant has an engagement filament with an enlarged proximal end. The delivery system has various engagement mechanisms to capture the enlarged proximal end of the engagement filament. With this engagement, the implant pusher shaft could apply distal force to the implant during delivery and deployment. To release, the enlarged proximal end of the engagement filament is let free and thereby release the implant. To simplify the description herein, the proximal portion of the implant pusher shaft, the motion of the implant release control mechanism, and the shape transformation of the coil implant will not be included when describing such engagement mechanism. In some embodiments, as described individually below, the enlarged proximal end of the engagement filament could be of a ball, a hook, a block or any other profile. The specific detail for each embodiment is determined by the needs of achieving a secure engagement as well as the matching design of the capture mechanism. As such, what has been described herein should not be viewed as limiting to the scope of the present teachings. According to some embodiment, the engagement filament could have some degree of flexibility in order to push the implant in tortuous anatomy.

FIGS. 20A-20B illustrate one exemplary embodiment of a captured enlarged proximal end (260) of the engagement filament (90) mechanism. FIG. 20A shows that the inner side wall of the implant pusher shaft (20) has a recess (262) which is configured to trap the enlarged proximal end (260) of the engagement filament (90). The engagement wire (40) also has an enlarged distal end. The enlarged distal end of the engagement wire (40) is configured to be positioned over the recess (262) with little or no space left in between this enlarged distal end and the luminal wall of the implant pusher shaft (20) so that the enlarged distal end of the engagement filament (90) is securely captured within the recess (262). One skilled in the art should understand that the shape, size, construct of the enlarged distal end of the engagement wire (40), and the enlarged proximal end (260) of the engagement wire (40) could vary so long as the designed purpose is achieved.

As illustrated, when the implant engages the delivery system (10), the enlarged proximal end (260) of the engagement filament (90), of the implant is positioned inside the recess (262) of the inner luminal wall of the implant pusher shaft (20). The engagement wire (40) extends to its most distal position, so that its enlarged distal end is positioned on top of the recess (262) holding the enlarged proximal end (260) of the engagement filament (90). To release the implant, a clinician retracts the engagement wire (40) proximally, so that its enlarged distal end moves proximally away from the recess (262) and thereby frees the enlarged proximal end (94) of the engagement filament (90), as shown in FIG. 20B.

FIGS. 21A-21B illustrate another exemplary embodiment of captured and enlarged proximal end (270) of the engagement filament (90) mechanism. FIG. 21A shows that unlike what has been described in reference to FIGS. 20A-20B, the recess (272) configured to capture the enlarged proximal end (270) of the engagement filament (90) is at the distal end portion of the engagement wire (40). As shown in FIG. 21A, when the implant engages the delivery system (10), the enlarged proximal end (270) of the engagement filament (90), of the implant is positioned inside the recess (272) at the distal end portion of the engagement wire (40). The size and shape of this distal end portion of the engagement wire (40) is configured to allow a secure capture of the enlarged proximal end (270) of the engagement filament (90) with little or no space left so that the enlarged proximal end (270) of the engagement filament (90) cannot escape. The portion of the engagement wire (40) proximal to this recess (272) could have various shapes and sizes. Thus, what has been illustrated in FIG. 21A should not be viewed as a limit. To release the implant, a clinician extends the engagement wire (40) distally, allowing the recess (272) at its distal end portion extending outside of the implant pusher shaft (20), so that its enlarged proximal end (270) of the engagement filament (90) can be freed, as shown in FIG. 21B.

Figure 22B:
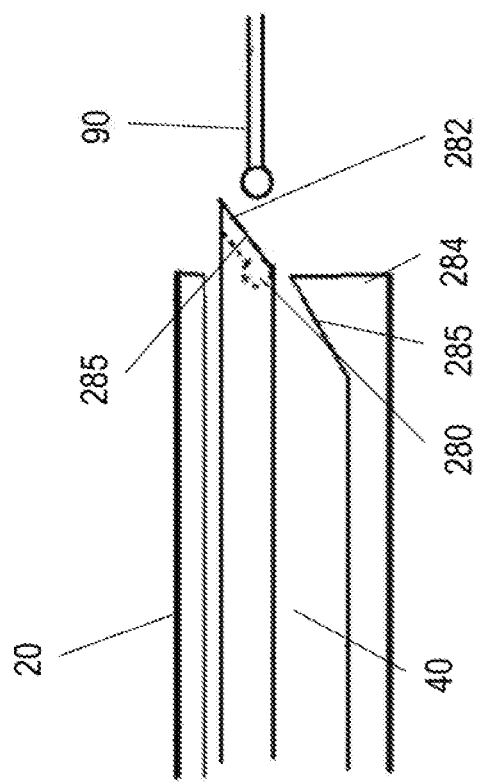
Figure 22A:
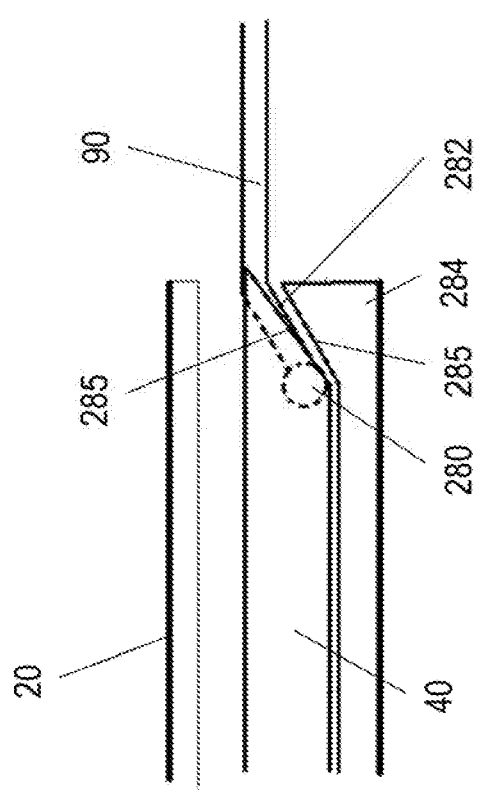

FIGS. 22A-22B illustrate a variation of the exemplary embodiment of illustrated in FIGS. 21A-21B. Similar to what has been described in FIG. 21A, the distal end portion of the engagement wire (40) also has a recess (282) configured to capture the enlarged proximal end (280) of the engagement filament (90). Unlike what has been described in FIG. 21A, the distal end portion of the implant pusher shaft (20) also has an internal ramp (284) similar to what has been described in reference to FIG. 8A. Also similar to what has been described in reference to FIG. 8A, the distal end of the engagement wire (40) also has an angled surface (285) that is configured to match the proximal angle (286) of the ramp (284). So that, when the engagement wire (40) is pushed against the ramp, the distal end surface (285) of the engagement wire (40) aligns with the angled proximal surface (286) of the ramp (284). As shown in FIG. 22A, the recess (282) is positioned on this angled surface of the engagement wire (40).

Similar to what has been described in FIGS. 21A-21B, when the implant engages the delivery system (10), the enlarged proximal end (280) of the engagement filament (90), of the implant is positioned inside the recess (282) at the distal end portion of the engagement wire (40) as shown in FIG. 22A. To release the implant, a clinician extends the engagement wire (40) distally, allowing the recess (282) on the angled surface (285) of the engagement wire (40) to extend outside of the implant pusher shaft (20), so that its enlarged proximal end (280) of the engagement filament (90) can be freed, as shown in FIG. 21B.

Figure 23B:
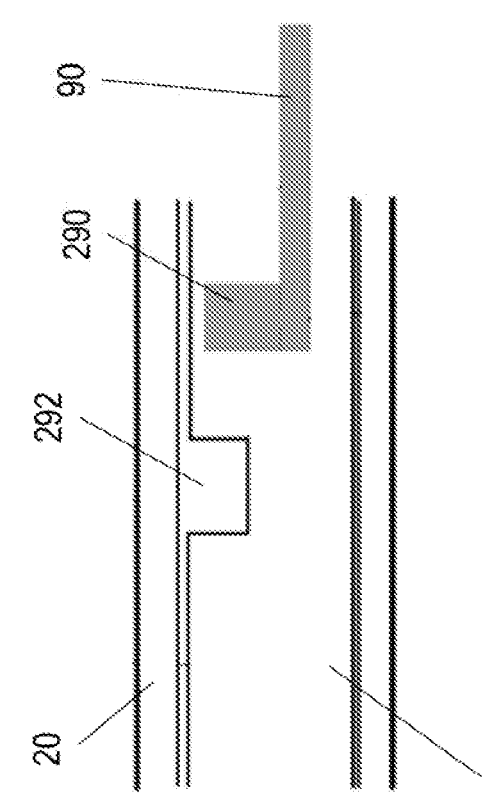
Figure 23A:
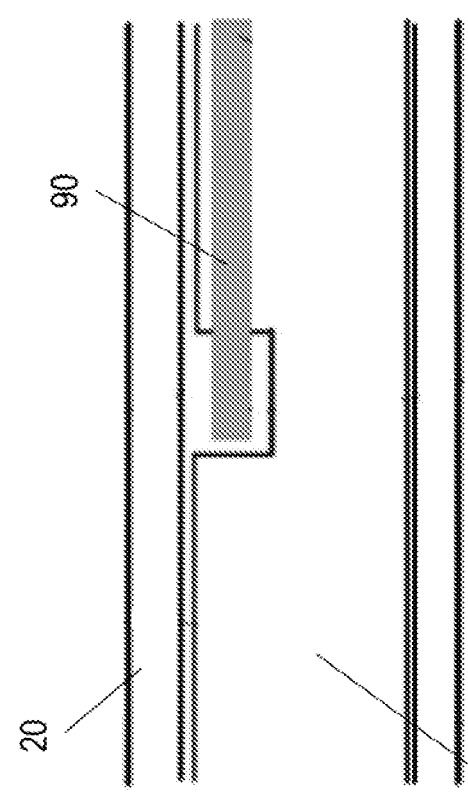

FIGS. 23A-23B illustrate a variation of the exemplary embodiment illustrated in FIGS. 21A-21B. Similar to what has been described in FIG. 21A, the distal end portion of the engagement wire (40) also has a recess (292) configured to capture the enlarged proximal end (290) of the engagement filament (90). Also similar to what has been described in FIGS. 21A-21B, when the implant engages the delivery system (10), the enlarged proximal end (290) of the engagement filament (90) of the implant is positioned inside the recess (292) at the distal end portion of the engagement wire (40) as shown in FIG. 23A. Unlike what has been described above, to release the implant, a clinician rotates the engagement wire (40) causing the recess (292) to disengage the enlarged hook shaped proximal end (290) of the engagement filament (90), and thereby releasing implant.

Figure 24A:
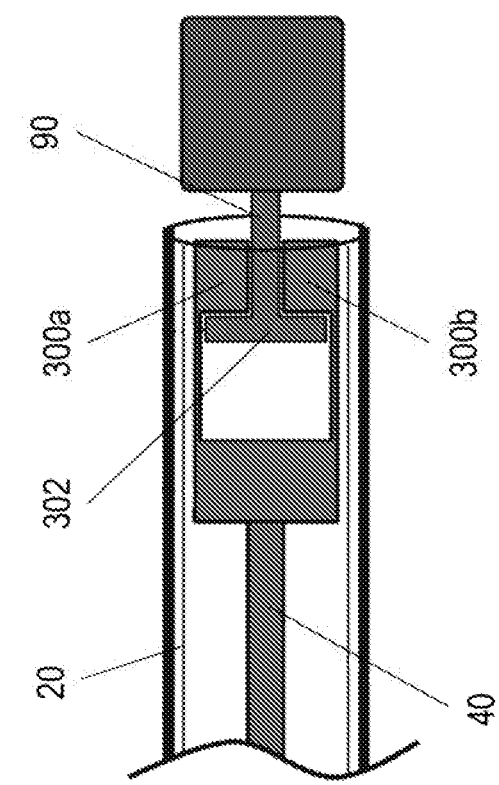
Figure 24B:
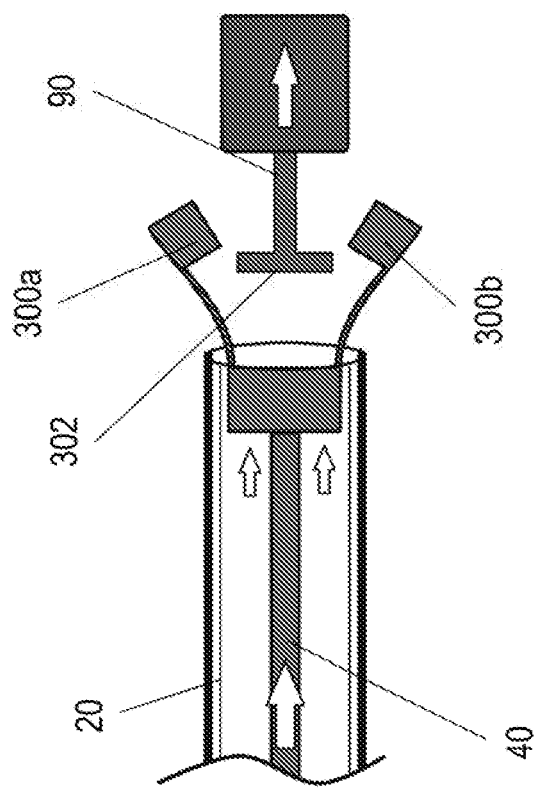

FIGS. 24A-24B illustrate another exemplary embodiment of the captured enlarged proximal end (94) of the engagement filament (90) mechanism. FIG. 24A shows that the distal end of the engagement wire (40) has a collapsible grasping mechanism (300a, 300b). In one embodiment, the engagement wire (40) has the collapsible grasping mechanism (300a, 300b) at its distal end. Once the entire engagement wire (40) is positioned inside the axial lumen (22) of the implant pusher shaft (20), its collapsible grasping mechanism (300a, 300b) collapses, and is configured to capture the enlarged proximal end (94) of the engagement filament (90) as shown in FIG. 24A. Once the collapsible grasping mechanism (300a, 300b) of the engagement wire (40) extends outside the implant pusher shaft (20), the collapsible grasping mechanism (300a, 300b) opens. The implant is then released as shown in FIG. 24B.

Figure 25A:
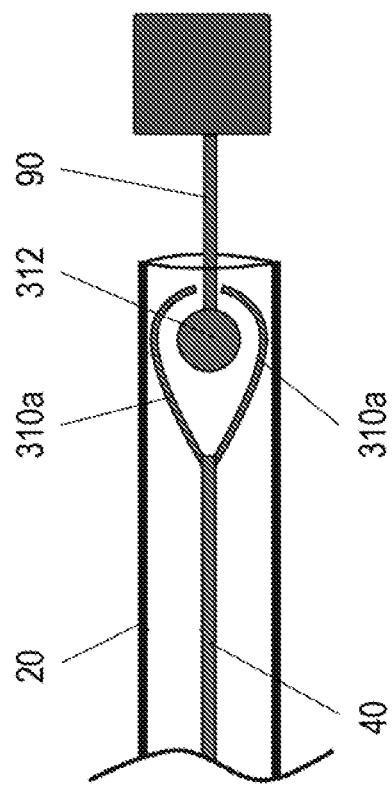
Figure 25B:
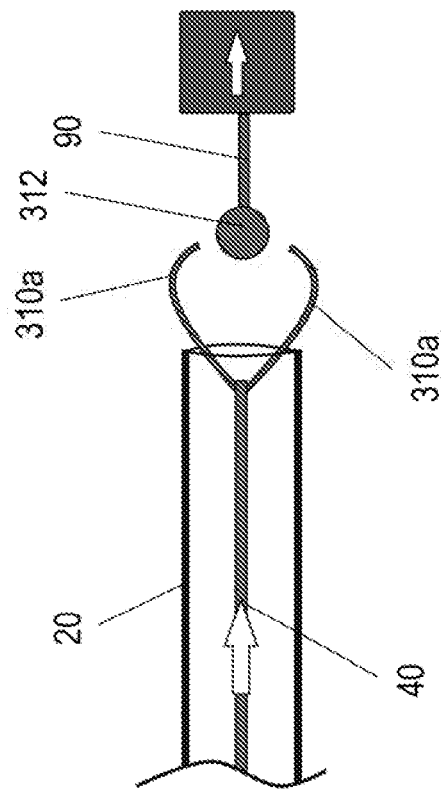

FIGS. 25A-25B illustrate a variation of the exemplary embodiment of illustrated in FIGS. 24A-24B. FIGS. 24A-24B show a grasping bracket like collapsible grasping mechanism (300a, 300b). FIGS. 25A-25B show a claw like collapsible grasping mechanism (310a, 310b). In one embodiment, the collapsible grasping mechanism (310a, 310b) has a predefined opening configuration. When trapped inside the implant pusher shaft lumen, the collapsible grasping mechanism (310a, 310b) collapses. When released from implant pusher shaft lumen, the collapsible grasping mechanism (310a, 310b) resumes its pre-defined open configuration either by thermal shape recovery, or by physical (spring) recovery.

Figure 26A:
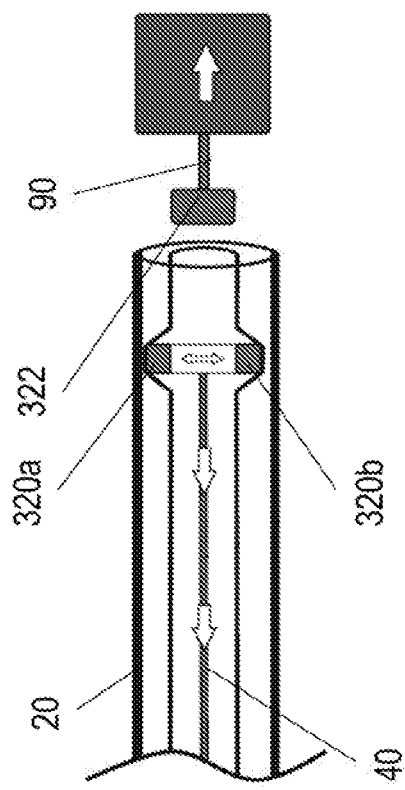
Figure 26B:
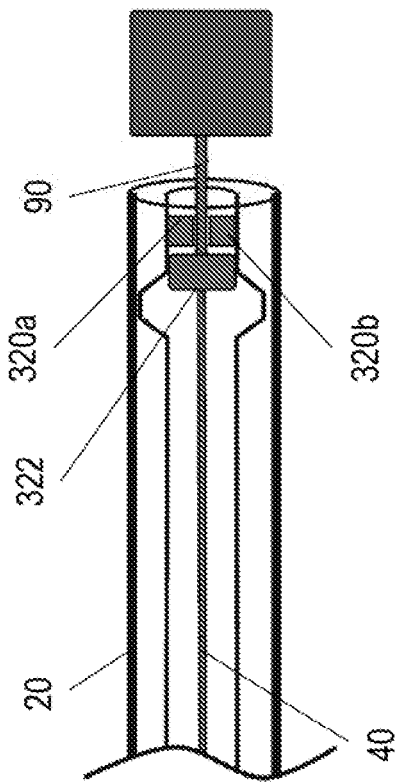

FIGS. 26A-26B illustrate another variation of the exemplary embodiment that is illustrated in FIGS. 24A-24B and FIGS. 25A-25B. FIGS. 26A-26B also illustrate a collapsible grasping mechanism (320a, 320b) at the distal end of the engagement wire (40). Unlike what has been described in in FIGS. 24A-24B and FIGS. 25A-25B, the opening of the collapsible grasping mechanism (320a, 320b) is achieved by a proximal pull of the engagement wire (40). As shown in FIG. 26A, the inner luminal wall of the distal end portion of the implant pusher shaft (20) have a profile that allows the opening and collapsing of the collapsible grasping mechanism (320a, 320b). When the engagement wire (40) extends to its most distal position, the collapsible grasping mechanism (320a, 320b) collapses in a relative narrow distal portion. When the engagement wire (40) retracts proximally, the collapsible grasping mechanism (320a, 320b) travels to a portion of the implant pusher shaft lumen where internal space allows the collapsible grasping mechanism (320a, 320b) to open.

Figure 27A:
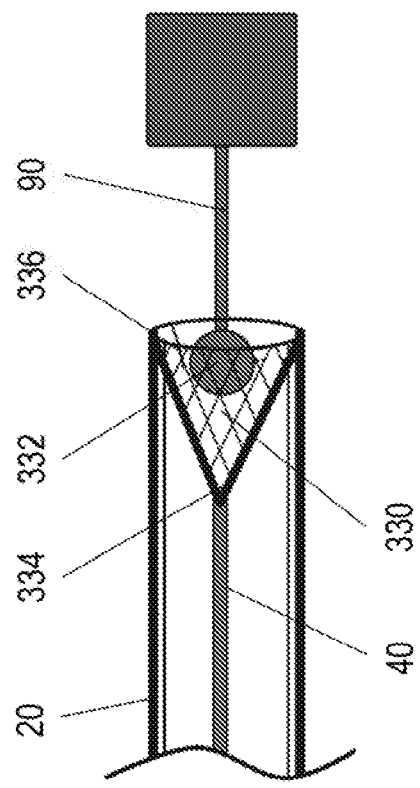
Figure 27B:
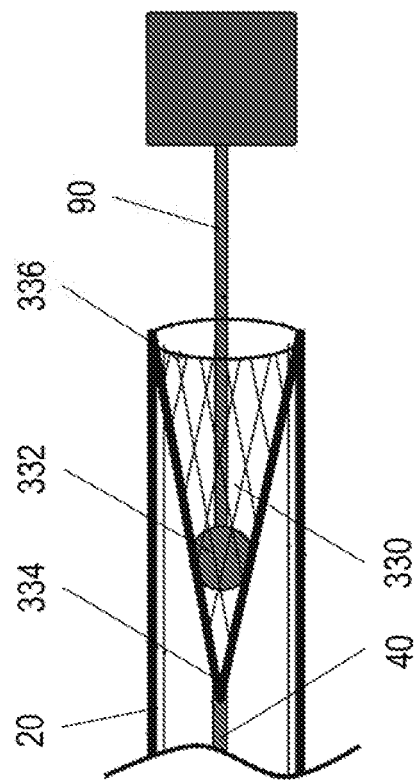

FIGS. 27A-27B illustrate another exemplary embodiment of captured enlarged proximal end (94) of the engagement filament (90) mechanism. FIG. 27A shows that the distal end of the engagement wire (40) has a transformable grasping mechanism (330). In one embodiment, the grasping mechanism (330) has a cone shaped weave or braid with the enlarged distal end (336) attaching to the distal end (26) of the implant pusher shaft (20), and the proximal end (334) joins the distal end (46) of the engagement wire (40). In one embodiment, the grasping mechanism (330) has a "finger trap" construction so that when the engagement wire (40) being pulled proximally, the cone shaped weave stretches to a narrower and elongated profile which is configured to trap the enlarged proximal end (94) of the engagement filament (90) as shown in FIG. 27A. To release the implant, a clinician extends the engagement wire (40) distally, so that the coned shaped weave expands radially and thereby allowing the enlarged proximal end (94) of the engagement filament (90) to be freed.

FIGS. 28A-28B illustrate a variation of the exemplary embodiment of illustrated in FIGS. 27A-27B. FIG. 28A also shows that the distal end of the engagement wire (40) which has a transformable grasping mechanism (340). The transformable grasping mechanism (340) has a membrane with its distal end (346) joins the distal end (26) of the implant pusher shaft (20), its proximal end (344) joins the distal end of the engagement wire (40). When two ends of the membrane pushes toward each other, its middle portion (348) collapses to capture the enlarged proximal end (94) of the engagement filament (90) between the collapsed middle portion (348) and its proximal end (344). In one embodiment, the membrane could be a braid, a weave, and/or a thin film comprising metal and/or plastic. Unlike what has been described in FIG. 27A, when the engagement wire (40) extends to its most distal position, the membrane biases into a collapsed state, capture the enlarged proximal end (94) of the engagement filament (90) as shown in FIG. 28A. When the engagement wire (40) being pulled proximally, the membrane stretches, and its middle portion (348) expands releasing the implant.

FIGS. 29A-29B illustrate another exemplary embodiment of captured enlarged proximal end (352) of the engagement filament (90) mechanism. FIG. 29A shows that the distal end of the engagement wire (40) having a collapsible element (350). In one embodiment, collapsible element (350) could be a fluid-filled balloon, an expanded cage or other expanded element configured to be collapse and expand via the engagement wire (40). When the collapsible element (350) expands to a size, it traps the engagement filament (90) between the collapsible element (350) and inner luminal wall of the implant pusher shaft (20), and thereby trapping the enlarged portion of the engagement filament (90) proximal to the collapsible element (350) as shown in FIG. 29A. When the collapsible element (350) contracts, the enlarged end (352) of the engagement filament (90) is then released as shown in FIG. 29B. In one embodiment, contraction of collapsible element (350) can be achieved by withdrawing fluid via a lumen of the engagement wire (40), manipulating (e.g. rotate, retract or advance) the engagement wire (40), and/or a combination of the two.

FIGS. 30A-30B illustrate another exemplary embodiment of captured enlarged proximal end (362) of the engagement filament (90) mechanism. FIG. 30A shows the distal end (26) of the implant pusher shaft (20) having a polarity of distal flanges (368a, 368b). The distal end (44) of the engagement wire (40) has a plurality of connecting members (366a, 366b) each with a distal end joining a flange (368a, 368b) of the implant pusher shaft (20), so that the proximal ends (364) all join to the distal end (46) of the engagement wire (40). As the engagement wire (40) extends to its most distal position, the connecting members (366a, 366b) are under no tension, and the distal flange of the implant pusher shaft (20) has a first configuration which is generally perpendicular to the longitudinal axis of the implant pusher shaft (20), so that the distal flanges (368a, 368b) partially covers the distal opening of the implant pusher shaft lumen (22), trapping the enlarged proximal end (362) of the engagement filament (90) inside the implant pusher shaft lumen (22) while allowing the remaining portions engagement filament (90) extending outside as shown in FIG. 30A. The implant is then engaged to the delivery system (10), ready to be delivered and deployed. As the engagement wire (40) is pulled proximally, the connecting members (366a, 366b) are also tensioned. The distal flanges (368a, 368b) of the implant pusher shaft (20) is then pulled proximally to assume a second configuration where the distal flange (368a, 368b) of the implant pusher shaft (20) is pulled to be at an acute angle to the longitudinal axis of the implant pusher shaft (20). The original partially blocked distal opening of the implant pusher shaft (20) is now opened so that the enlarged proximal end (362) of the engagement filament (90) can be freed as shown in FIG. 30B.

FIG. 31 illustrates another exemplary embodiment of captured and enlarged proximal end (372) of the engagement filament (90) mechanism. FIG. 31 shows a distal end (26) of the implant pusher shaft (20) having two flanges (374a, 374b) generally perpendicular to the longitudinal axis of the implant pusher shaft (20), with two longitudinal slits (375a, 375b) each extending proximally from a flange (374a, 374b) to a distance dividing these the distal portion (29) of the implant pusher shaft (20) into two halves. The inner lumen of the split distal portion (29) of the implant pusher shaft (20) has a cone like configuration with the enlarged end of the cone distal to the smaller end of the cone. FIG. 31 further illustrates an enlarged distal end (372) of the engagement wire (40). As the engagement wire (40) is at its most distal position, the split distal portion of the implant pusher shaft (20) extends generally paralleled to each other, the flange partially blocks the distal opening of the implant pusher shaft (20), and the enlarged distal end (372) of the engagement wire (40) positioned inside the enlarged end of the cone within the axial lumen of the split distal portion (29) of the implant pusher shaft (20). In this configuration, the enlarged proximal end (94) of the engagement filament (90) is captured by the implant pusher shaft (20), while the remaining portions engagement filament (90) extending outside as shown in FIG. 30. As the engagement wire (40) pulled proximally, its enlarged distal end (372) of the engagement wire (40) is forced to the narrowed end of the cone. The two split halves are then forced to open along its two slits. The implant is now released.

One skilled in the art should understand that the cone shaped inner lumen within the split distal portion (29) of the implant pusher shaft (20) could also have a reversed configuration as shown here, so that the narrow end of the cone is distal to the larger end of the cone. By advancing the engagement wire (40), the enlarged distal end of the engagement wire (40) splits the two halves. In another embodiment, a relatively narrow channel is configured to be distal to the cone shaped inner luminal feature for the enlarged proximal end (372) of the engagement filament (90) to be captured within.

FIGS. 32A-32B illustrate another exemplary embodiment of a captured and enlarged proximal end (94) of the engagement filament (90) mechanism. FIG. 32A shows that the implant pusher shaft (20) has a funnel-shaped distal portion (384), with an aperture at the apex (386) of the funnel allowing the engagement wire (40) to extend through. The engagement wire (40) also has an enlarged distal end (380) which is configurator to capture the enlarged proximal end (382) of the engagement filament (90). When the engagement wire (40) retracts to its most proximal position, the enlarged proximal end (382) of the engagement filament (90) is then captured in between the enlarged distal end (380) of the engagement wire (40) due to being positioned in the narrowest portion of the funnel (384), as shown in FIG. 32A. When the engagement wire (40) extends distally, the enlarged distal end (380) of the engagement wire (40) moves distally, as shown in FIG. 32B. The implant is then released.

FIGS. 33A-33B illustrate another exemplary embodiment of a captured and enlarged proximal end (392) of the engagement filament (90) mechanism. FIG. 33A illustrates a pivotable flap (390) with one side pivotably joined to the inner luminal wall of the implant pusher shaft (20) at a distance from the distal end (26) of the implant pusher shaft (20). The distal end of the engagement wire (40) connects to a middle portion of the flap (390). When tension on the engagement wire (40) is removed, the flap (390) drops, as shown in FIG. 33A, the enlarged proximal end (392) of the engagement filament (90) is captured by the pivotable flap (390) on its proximal side. To release the implant, the engagement wire (40) extends, pushing the pivotable flap (390) to swivel as shown in FIG. 33B, and the implant is then released. Although the enlarged proximal end (94) of the engagement filament (90) shown in FIGS. 33A-33B have a hook shaped profile, one skilled in the art should understand that other shapes, sizes, and profiles could all be used to achieve the purpose of engaging an implant. Additionally, the flap (390) could have many design details known in the field to accommodate the elongated portion of engagement filament (90) such as the feature shown in FIG. 34A. Many pivotable feature known in the field could be adopted in this exemplary embodiment, such as a living hinge, a pin axis, a nitinol pre-shaped to pivot when the flap is advanced and etc.

Figure 34B:
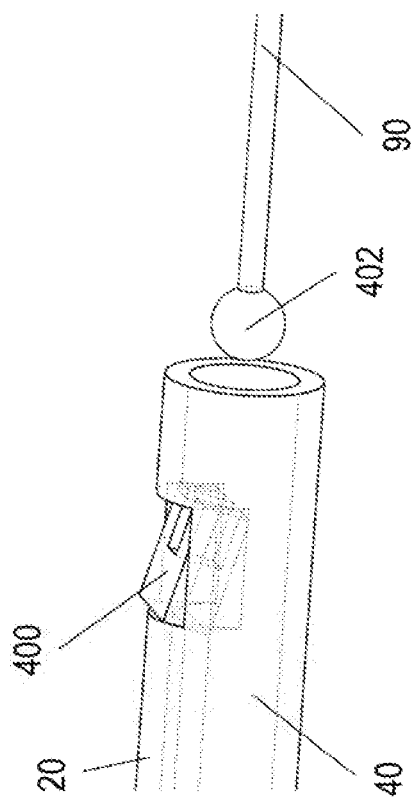
Figure 34A:
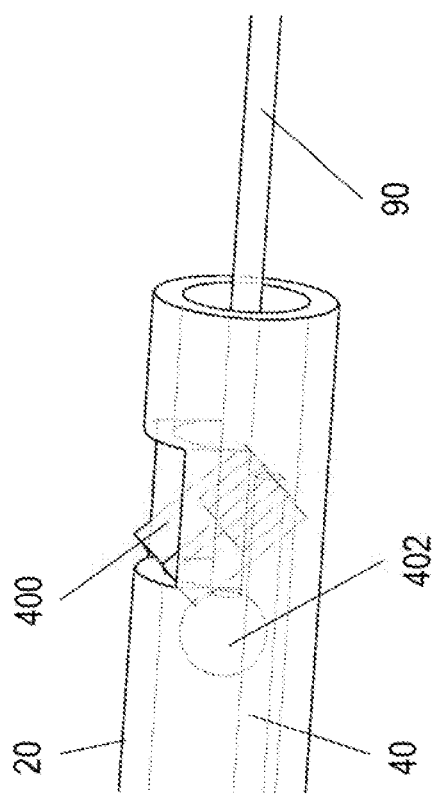

FIGS. 34A-34B illustrate a variation of exemplary embodiments of the pivotable engagement mechanism (400) with reference to FIGS. 33A-33B. Similar to what has been described with reference to FIGS. 34A-34B, the pivotable engagement mechanism (400) has a closed configuration to engage the enlarged proximal end (402) of engagement filament (90), and an open configuration to free the enlarged proximal end (402) of engagement filament (90). Unlike what has been described with reference to FIGS. 34A-34B, the implant pusher shaft (20) has an opening on its tubular wall at its distal portion. The pivotable engagement mechanism (400) pivot to join the proximal end of the opening.

When the implant engages the delivery system (10), the pivotable engagement mechanism (400) drops and traps the enlarged proximal end (402) of the engagement filament (90) proximal to the flap. To release the implant, the engagement wire (40) extends distally, pushing onto the pivotable engagement mechanism (400), causing it revolve radially. As the pivotable engagement mechanism (400) flips open, the implant is then released.

Figure 35B:
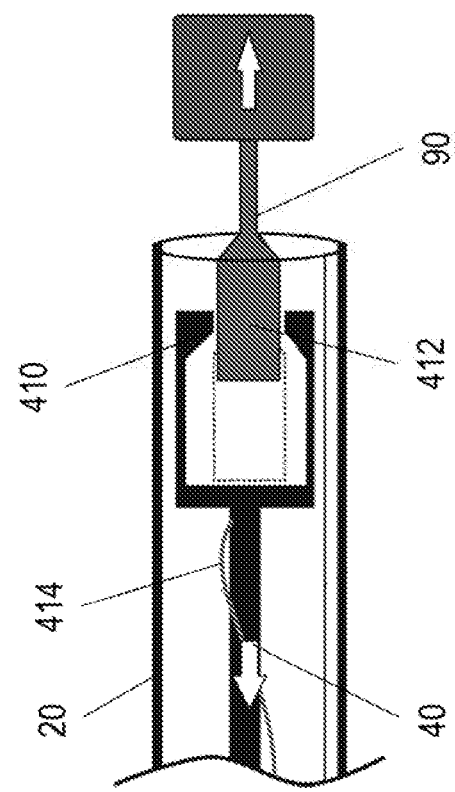
Figure 35A:
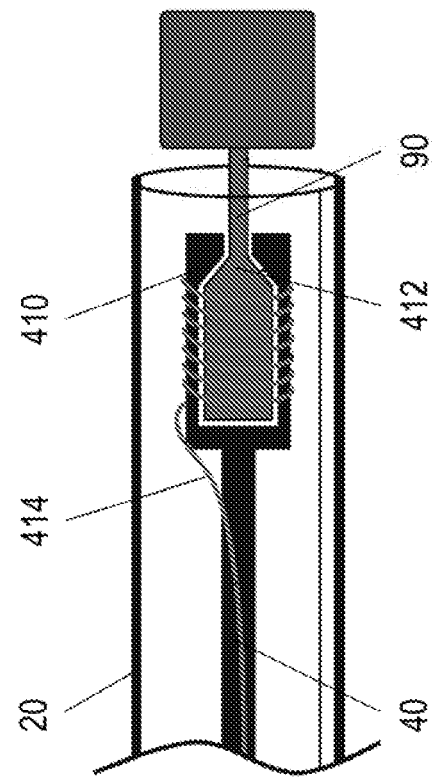

FIGS. 35A-35B illustrate another exemplary embodiment of captured enlarged proximal end (94) of the engagement filament (90) mechanism. FIG. 35A illustrates a collapsible engagement mechanism (410) at the distal end of the engagement wire (40). The collapsible engagement mechanism (410) has a closed configuration and an open configuration. FIG. 35A further illustrates a filament (414) that is configured to wrap around the collapsible engagement mechanism (410), constraining it into a closed configuration whereby capturing the enlarged proximal end (412) of the engagement filament (90). In one embodiment, the proximal end of the filament (414) is operably controlled by a clinician. To release the implant, the clinician pulls the filament (414) proximally, triggering the unwrapping of the filament (414). As the constraint is being removed, the collapsible engagement mechanism (410) of engagement wire (40) opens up to its pre-shape set position, and frees the enlarged proximal end (412) of the engagement filament (90). Those skilled in the art should understand that the collapsible engagement mechanism (410) could have many shapes, sizes, and constructions such as made of shape memory alloy etc. In another embodiment, the unwrapping of the filament (414) from the collapsible engagement mechanism (410) could be achieved by a clinician rotating engagement wire (40), or a combination of both retraction and rotation.

FIGS. 36A-36B illustrate a variation of the exemplary embodiment described with reference to FIGS. 35A-35B. Similar to the exemplary embodiments shown in FIGS. 35A-35B, the filament (424) is used to engage the enlarged proximal end (94) of the engagement filament (90). Unlike what the exemplary embodiments shown in FIGS. 35A-35B, the engagement wire (40) does not have any special engagement distal end features. During delivery and deployment, the filament (424) wrapped a distal portion of engagement wire (40) and a proximal portion of the engagement filament (90) together captures the enlarged end of the engagement filament (90). In one embodiment, the filament (424) wraps around multiple times, such as 2 or 3 turns. Again, similar to the exemplary embodiments shown in FIGS. 35A-35B, the unwrapping of the filament (424), either by retraction and/or rotation of the filament and/or engagement wire (40), the implant is released as shown in FIG. 36B.

FIGS. 37A-37B illustrate another exemplary embodiment of captured enlarged proximal end (432) of the engagement filament (90) mechanism. FIG. 37 illustrates an engagement wire (40) having one O-ring (430) shaped feature at its distal end. The O-ring (430) shaped features pivotably joins the engagement wire (40) at its edge. The through-hole on the O-ring (430) shaped feature is sized and shaped to allow the enlarged proximal end (432) of engagement filament (90) to travel through. As the O-ring (430) shaped feature is in its natural state, it forms an angle with the longitudinal axis of the implant pusher shaft (20), and thereby creates a tortuous path which allows the engagement filament (90) to extend through while capturing the enlarged proximal end (432) of engagement filament (90) proximal to the proximal O-ring (430) shaped feature as shown in FIG. 37A. To release the implant, engagement wire (40) could be advanced and/or retracted so that the O-ring (430) shaped feature resumes a relatively straight profile generally perpendicular to the longitudinal axis of the implant pusher shaft (20), so that the enlarged proximal end (432) of engagement filament (90) could extend proximally and thereby be freed.

All exemplary embodiments described with reference to FIGS. 20-37, relate to a non-deformable enlarged proximal end of the engagement filament. FIGS. 38-39 illustrate two exemplary embodiments where the engagement between the implant and the delivery system is achieved by a deformable enlarged proximal end of the engagement filament.

Figure 38B:
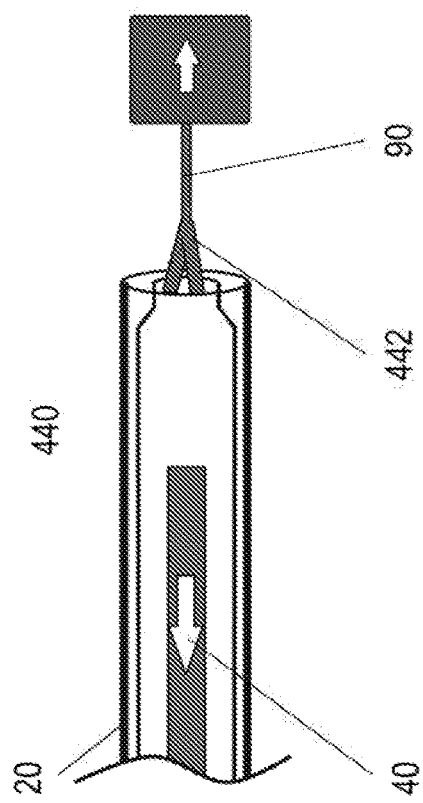
FIGS. 38-39 are perspective views of various exemplary engagement between a delivery system and a medical implant where a collapsible proximal end of the engagement filament is captured by the engagement wire, the implant pusher shaft, or, a combination of both in accordance with the present teachings.
Figure 38A:
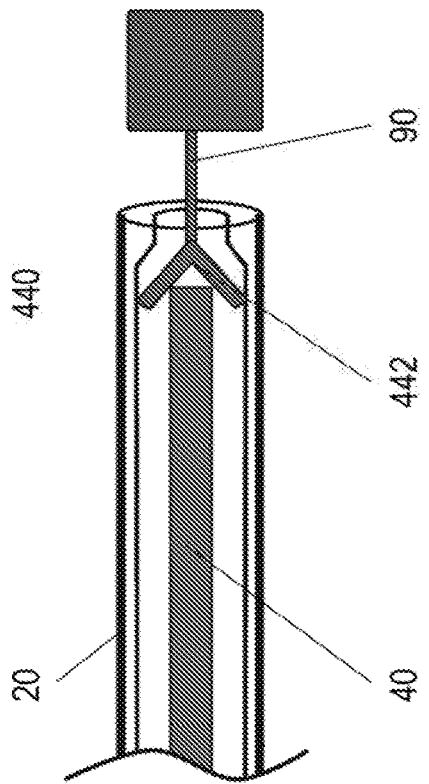

FIGS. 38A-38B illustrate another exemplary embodiment of a captured and collapsed proximal anchor (442) of the engagement filament (90) mechanism. In one embodiment, a distal opening of the implant pusher shaft (20) has a smaller general diameter than its axial lumen. The collapsed proximal anchor (442) of the engagement filament (90) has a collapsible anchor that has a, first, radially expanded configuration and a, second, collapsed configuration. As shown in FIG. 38A, the distal end of the engagement wire (40) is sized to push open the collapsed proximal anchor (442) of the engagement filament (90). Once the engagement wire (40) is retracted, the expanded proximal anchor (442) collapses to its second profile. FIG. 38A illustrates the engagement wire (40) pushing open the proximal anchor (442) of the engagement filament (90), and the collapsible proximal anchor (442) of the engagement filament (90) in its radially expanded configuration being captured inside the axial lumen (22) of the implant pusher shaft (20). The radially expanded anchor is then blocked by the narrow distal opening of the implant pusher shaft (20) thereby securing the implant to the delivery system (10). FIG. 38B illustrates the engagement wire (40) retracting, and the expanded proximal anchor (442) collapsing to a second smaller radial profile which allow it travels through the narrow distal opening of the implant pusher shaft (20). In one embodiment, the proximal anchor (442) of the engagement filament (90) could incorporate many other features known in the field. For example, the proximal anchor (442) could have a plurality of anchor elements in the shape of an arm, flange, and/or others.

Figure 39B:
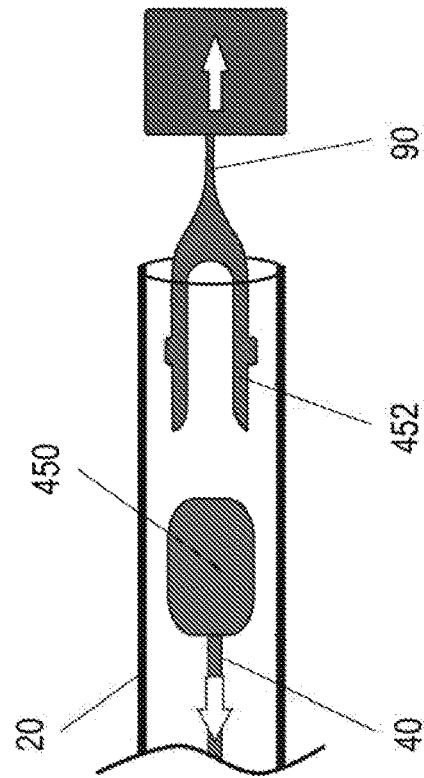
Figure 39A:
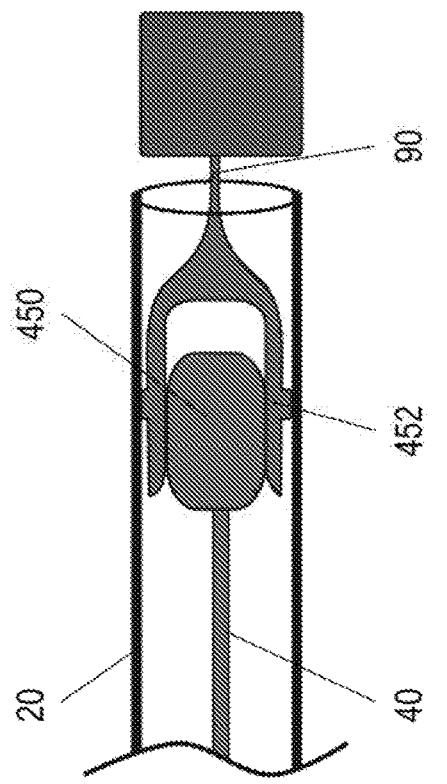

FIGS. 39A-39B illustrates a variation of the exemplary embodiment described with reference to FIGS. 38A-38B. Similar to the exemplary embodiments shown in FIGS. 38A-38B, the collapsed proximal anchor (452) of the engagement filament (90) also has a collapsible anchor (452). Unlike the exemplary embodiments shown in FIGS. 38A-38B, the distal opening of the implant pusher shaft (20) has the same general diameter as its axial lumen. Similar to the exemplary embodiments shown in FIGS. 38A-38B, the distal end (450) of the engagement wire (40) is sized to push open the collapsed proximal anchor (452) of the engagement filament (90). FIG. 39A illustrates the engagement wire (40) pushing open the proximal anchor (452) of the engagement filament (90), and the collapsible proximal anchor (452) of the engagement filament (90) in its radially expanded configured is frictionally captured inside the axial lumen (22) of the implant pusher shaft (20). FIG. 39B illustrates the engagement wire (40) retracting, and the expanded proximal anchor (452) collapsing to a second smaller radial profile which allows it to extend outside of the implant pusher shaft (20).

Now referring to another group of exemplary embodiments where the implant attaches to the delivery system with a friction engagement mechanism. FIGS. 40-43 illustrate that the distal end of the engagement wire comes in contact with a proximal portion of the engagement filament of the implant, together they frictionally fit inside the axial lumen of the implant pusher shaft. By retracting the engagement wire, the proximal portion of the engagement filament is then released.

Figure 40A:
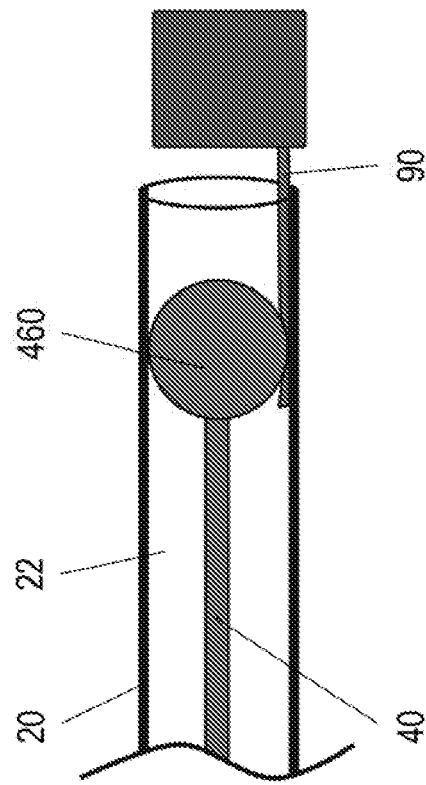
FIGS. 40-42 are perspective views of various exemplary engagement between a delivery system and a medical implant where a proximal portion of the engagement filament frictionally engages to the engagement wire and/or the implant pusher shaft in accordance with the present teachings.
Figure 40B:
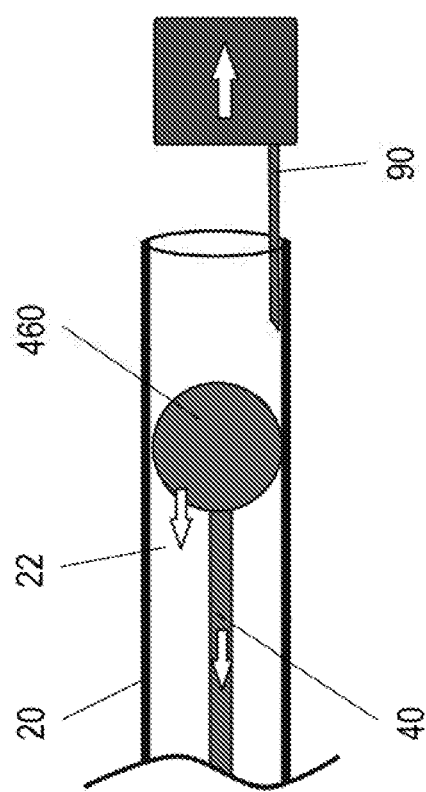

FIGS. 40A-40B illustrate an exemplary embodiment of the frictional engagement mechanism. FIG. 40A shows that the engagement wire (40) has an enlarged distal portion (460), such as a ball-shaped feature. During implant delivery and deployment, the enlarged distal portion (460) of the engagement wire (40) overlaps a proximal portion of the engagement filament (90). Together they are configured to frictionally engage the inner luminal space of the implant pusher shaft (20) as such, the implant is secured to prevent any accidental release. To release the implant, the engagement wire (40) retracts proximally, moving away from the proximal portion of engagement filament (90), thereby allowing the engagement filament (90) to be free, as shown in FIG. 40B.

FIG. 41 illustrates a variation to the exemplary embodiment shown in FIGS. 40A-40B. Unlike FIGS. 40A-40B, the engagement wire (470) does not have an enlarged distal portion. Instead, the overall size of the engagement wire (470) is configured to frictionally engage the proximal portion of the engagement filament (90) inside the implant pusher shaft lumen. Similar to what has been described with reference to FIGS. 40A-40B, a clinician simply retracts the engagement wire (470) proximally to release.

Both exemplary embodiments of the frictional engagement mechanism do not have disclosed any special design feature at the proximal portion of the engagement filament (90). One skilled in the art should understand that the proximal end portion of the engagement filament (90), as well as distal end portion of the engagement wire (40), could adopt many detailed features so long as the overlapping assembly of the distal end portion of the engagement wire (40) and the proximal end portion of the engagement filament (90) is securely engaged to the inner axial lumen (22) of the implant pusher shaft (20).

FIG. 42 illustrates a variation to the exemplary embodiment shown in FIGS. 40A-40B. Similar to what has been described with reference to FIG. 40A, the engagement wire (40) has a ball-shaped enlarged distal portion (480). Unlike FIG. 40A, the proximal end (482) of the engagement filament (90) has an O-ring like feature. When the implant engages the delivery system (10), the ball-shaped enlarged distal portion (480) is positioned within the O-ring like feature. Together, the ball-ring assembly tightly fits inside the implant pusher shaft lumen as shown in FIG. 42. Similarly, by retracting the engagement wire (40) proximally, the implant is released.

FIGS. 43-45 illustrate another group of exemplary embodiments, where the implant attaches to the delivery system in such a way that the engagement wire needs to breakaway in order to release the implant. FIG. 43 illustrates another exemplary embodiment of the engagement wire-loop mechanism. As shown in FIG. 43, the distal end (26) of the implant pusher shaft (20) has an internal ramp (492), similar to what has been described above, such as with reference to FIG. 8, that partially blocks the distal opening of the implant pusher shaft lumen. The distal portion of the engagement wire (40) has a breakable portion (490). According to one embodiment, the breakable portion (490) can be constructed and arranged to break at a force and/or torsion higher than forces and/or torsion encountered during the implant delivery and deployment. The breakable portion (490) is constructed to break at a predetermined threshold. The distal end of the engagement wire (40) is fixed to the internal ramp (492). The engagement loop (92) of the implant is preloaded so that it is captured by the engagement wire (40) prior to implant delivery. When releasing, the engagement wire (40) is pulled proximally, causing tension in engagement wire (40) until the breakable portion (490) is pulled apart, and thereby releasing the implant.

FIG. 44 illustrates a variation to the exemplary embodiment shown in FIG. 43.

Similar to what has been described in FIG. 43, the engagement wire (504) has a breakable portion (490). Unlike FIG. 43, the distal end (500) of the engagement wire (504) fixedly engages to a point on the inner axial lumen (22) of the implant pusher shaft (20). FIG. 44 shows that the proximal end (94) of the engagement filament (90) has an eyelet like (502) feature, sized and shaped to allow the distal end (500) of the engagement wire (504) to pass through. Similar to what has been described above, the implant is preloaded so that its proximal eyelet end (502) of the engagement filament (90) is captured by the engagement wire (504). When releasing, the engagement wire (504) is pulled proximally, causing tension in engagement wire (504) until the distal end (500) of the engagement wire (504) breaks away from the inner axial lumen (22) of the implant pusher shaft (20), and thereby releasing implant.

FIG. 45 illustrates another variation to the exemplary embodiment shown in FIG. 43. Unlike what has been described in FIG. 45, the breakable portion (510) is at a proximal portion of the engagement filament (90). The engagement filament (90) fixed attaches to the engagement wire (40). The distal end (26) of the implant pusher shaft (20) has a narrow opening smaller than its luminal diameter so that the distal end (26) of the implant pusher shaft (20) could transfer distal pushing force to the proximal end of the implant. To release the implant, the engagement wire (40) retracts proximally, causing tension in the engagement filament (90) until the breakable portion (510) is pulled apart.

FIGS. 46-53 illustrate a group of exemplary embodiments where the proximal end of the implant has a bracket engagement mechanism. According to one embodiment of the present teachings, unlike what has been described with reference to FIG. 3, the exemplary implant described in FIGS. 46-53 has no engagement filament. Instead, a bracket engagement mechanism fixed to the proximal end of the coil implant. In one embodiment, the bracket engagement mechanism has an inner space with a relatively narrow proximal opening. This inner narrow space is sized and shaped to capture the distal engagement mechanism of the delivery system. The narrow proximal opening of the bracket allows the engagement wire to extend through.

Figure 46B:
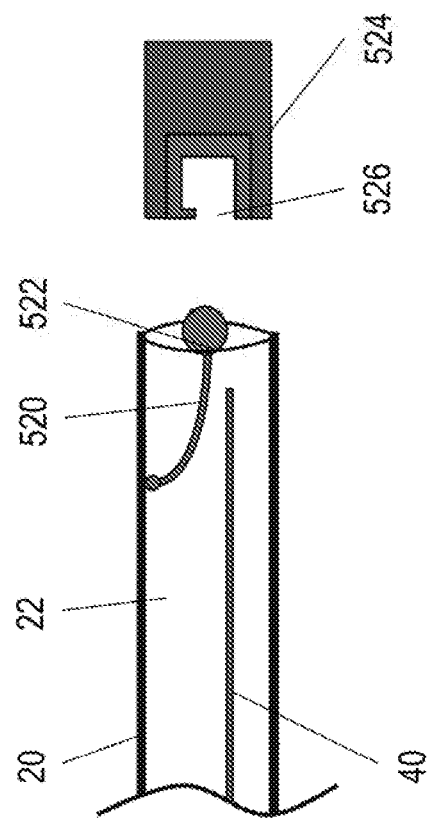
Figure 46A:
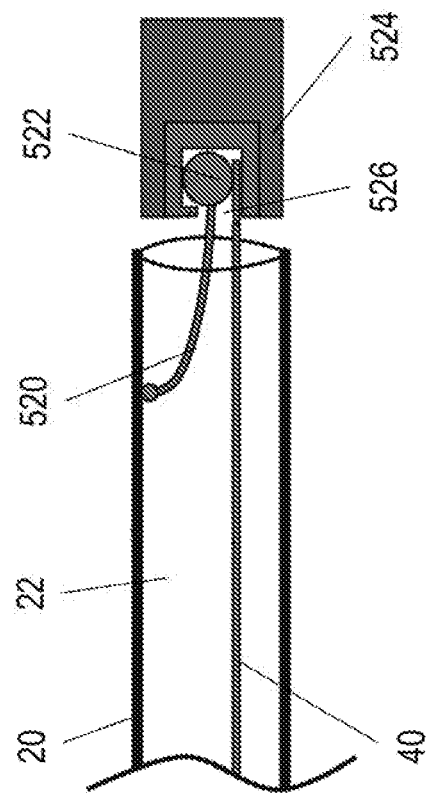

Now referring the FIGS. 46A-46B, an exemplary bracket engagement mechanism (524) of the implant captures the distal end of the delivery system (10). FIG. 46A shows that the implant pusher shaft (20) has an axial lumen (22) allowing the engagement wire (40) to be slidably disposed within. A flexible tether (520) is attached to the inner luminal wall of the implant pusher shaft (20) at a distal portion. The free end of the flexible tether has a ball-shaped or otherwise enlarged portion (522). Such enlarged portion (522) at the free end of the tether (520) is configured to extend distally outside of the implant pusher shaft (20) and into the proximal bracket engagement mechanism (524) at the proximal end of the implant. Such enlarged portion (522) at the free end of the tether (520) is also configured to pass through the narrow proximal opening (526) of the bracket engagement mechanism (524) within minimum extra space in between the enlarged portion (522) and the opening (526).

During implant delivery and deployment, as shown in FIG. 46A, the enlarged portion (522) at the free end of the tether (522) is first positioned inside the inner space of the bracket engagement (524). The engagement wire (40) then extends distally with its distal end extending inside of the inner space of the bracket engagement mechanism (524). Between the tight fit between the size of the narrow opening (526) of the bracket engagement mechanism (524) and the enlarged free end (522) of the tether (520), the engagement wire (40) prevents the enlarged free end (522) of the tether (520) from withdrawing from the bracket engagement mechanism (524). To release the implant, the engagement wire (40) retracts proximally, and the enlarged free end (522) of the tether (520) is then free to leave the inner space of the bracket engagement mechanism (524) as shown in FIG. 46B. In one embodiment, the narrow proximal opening (526) of the bracket engagement mechanism (524) is centered to the bracket engagement mechanism (524). In another embodiment, the narrowing proximal opening (526) of the bracket engagement mechanism (524) is off center to the bracket engagement mechanism (524), as shown in FIGS. 46A-46B, in order to facilitate smooth travel of the enlarged free end (522) of the tether during implant release.

Figure 47B:
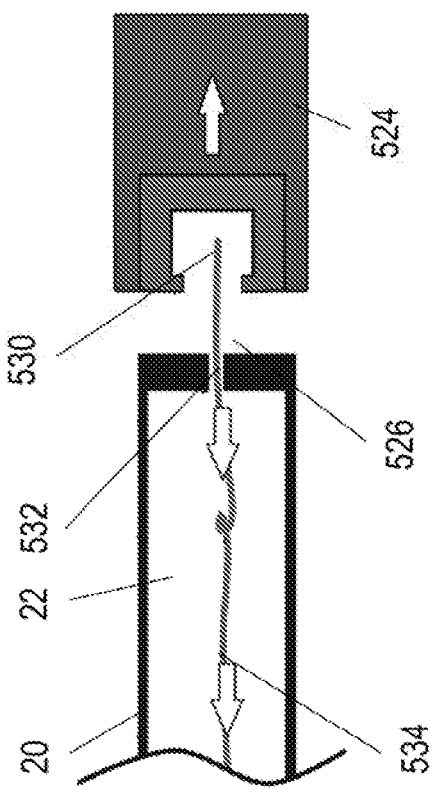
Figure 47A:
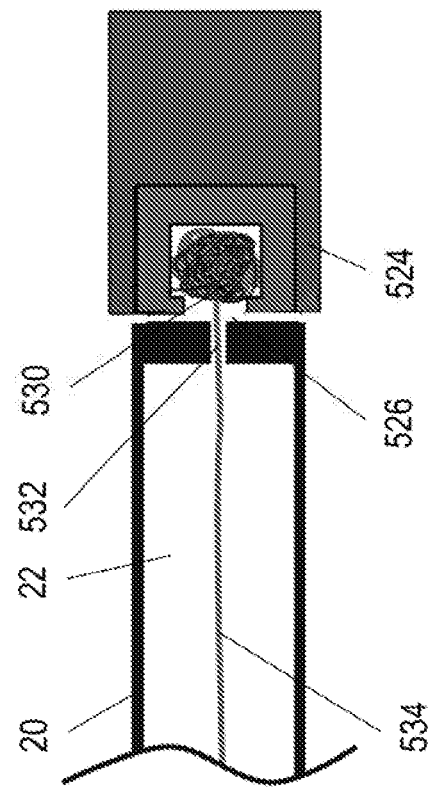

FIGS. 47A-47B illustrate another exemplary embodiment of the bracket engagement mechanism (524). FIG. 47A shows that the distal end of the engagement wire (40) has a knot (530). The implant pusher shaft (20) has an axial lumen with a narrower distal opening (532) configured to allow a distal portion of the engagement wire (40) to pass through. The knotted end (530) of the engagement wire (40) has a larger diameter than remaining portion of the engagement wire (40) and the overall diameter of the narrow opening (532) of the implant pusher shaft (20). Additionally, the knotted end (530) of engagement wire (534) also has a larger diameter than proximal narrow opening (526) of the bracket engagement mechanism (524) of the implant, while sized to fit inside the inner space of the bracket engagement mechanism (524). In one embodiment, the knotted end (530) of the engagement wire (534) can be set free into an elongated filament profile by a proximal pulling force. FIG. 47A illustrates the engagement of the implant to the delivery system (10), where the knot end of the engagement wire (534) is positioned inside the inner space of the bracket engagement mechanism (524), with the remaining portion of the engagement wire (534) extending from the knotted end (530) proximally through the narrow opening (526) of the bracket engagement mechanism (524) and the distal narrow opening of the implant pusher shaft (20), and into the implant pusher shaft lumen. To release the implant, the engagement wire (534) retracts proximally, the knotted end (530) disentangles into an elongated profile. Upon continue retracting the engagement wire (534) proximally, the untangled elongated knot end is then removed from the inner space of the bracket engagement mechanism (524). One skilled in the art should understand although a knot is described herein, it can be a winded coil or a wire mass.

FIGS. 48A-48B illustrate another exemplary embodiment of the bracket engagement mechanism (524). FIG. 48A shows that the engagement wire (40) has an enlarged end (540). A filament (542) further extends distally with its distal portion configured to be wrapped around the enlarged distal end (540) of the engagement. In one embodiment, the enlarged distal end (540) of the engagement wire (40) is configured to extend in and out of the bracket engagement mechanism (524) freely. Once the distal portion of the filament (542) wraps around the enlarged distal end (540) of the engagement wire (40), it is then tightly fit inside the bracket engagement mechanism (524) as shown in FIG. 48A. The implant (80) and delivery system (10) are then frictionally engaged. To release the implant, the wrapped filament (542) is removed from the enlarged distal end (540) of the engagement so that the bracket engagement mechanism (524) releases the engagement wire (40). In one embodiment, unwrapping of the filament (542) from the enlarged distal end (540) of the engagement wire (40) could be achieved either by retraction and/or rotation of the filament (542) and/or engagement wire (40).

FIGS. 49A-49B illustrate another exemplary embodiment of the bracket engagement mechanism (524). FIG. 49A shows that the engagement wire (40) has an expandable/collapsible end (550). In one embodiment, such collapsible distal end (550) of the engagement wire (40) has an expanded profile configured be positioned inside the inner space of the bracket engagement mechanism (524), and a collapsed profile configured to pass through the proximal narrow opening (526) of the bracket engagement mechanism (524). In one embodiment, the radial expansion of the collapsible end (550) could be achieved by many known mechanism in the field, such as balloon inflation etc. FIG. 49A shows that the distal end (550) of the engagement wire (40) expands, and is captured inside the bracket engagement mechanism (524). To release the implant, the expanded distal end (550) collapses, and then the engagement wire (40) retracts proximal and thereby free itself from the implant.

FIGS. 50A-50B illustrate another exemplary embodiment of the bracket engagement mechanism (524). FIG. 50A shows that the engagement wire (40) has a waist portion (562) near its distal end. In one embodiment, the waist portion (562) has a smaller diameter than portions distal and proximal to the waist portion (562). The engagement wire (40) further includes an expandable ring (560), for example made of a shape memory alloy. In one embodiment, the expandable ring (560) has an expanded profile allowing it sliding over the distal portion of the engagement wire (40). In another embodiment, the expandable ring (560) has a collapsed profile allowing it fit inside the waist portion (562) of the engagement wire (40). In one embodiment, the expandable ring (560) is configured to fit inside the waist portion (562) of the engagement wire (40). In another embodiment, once the expandable ring (560) positions inside the waist portion (562) of the engagement wire (40), the ring resumes its collapsed profile, as such the overall size of the ring is generally similar to that overall size of the rest of the engagement wire (40). This would allow the engagement wire (40) to be removed from the bracket engagement mechanism (524). During implant delivery and deployment, the expandable ring (560) positions proximal to the waist portion (562) of the engagement wire (40) and the bracket engagement mechanism (524) captures the distal end of the engagement wire (40). To release the implant, the engagement wire (40) retracts proximally, the ring is then pushed inside the waist portion (562) of the engage wire, allowing the engagement wire (40) to be free.

FIG. 51 illustrates another exemplary embodiment of the bracket engagement mechanism (524) capturing a collapsible distal engagement element (570) at the engagement wire (40). FIG. 51 shows that the distal end of the engagement wire (40) has a collapsible engagement element (570). Such engagement element (570) have a free end and a fixed end. Its fixed end joins the distal end of the engagement wire (40). In its pre-defined relaxed configuration, the element (570) extends radially outward from the longitudinal axis of the engagement wire (40). In this configuration, the engagement element (570) of the engagement wire (40) is captured inside the bracket engagement mechanism (524), thereby engaging the implant to the delivery system (10). To release the implant, the engagement wire (40) retracts proximally, the collapsible engagement element (570) forced to collapse and pass through the proximal narrow opening (526) of the bracket engagement mechanism (524). The implant is then freed.

Figure 52:
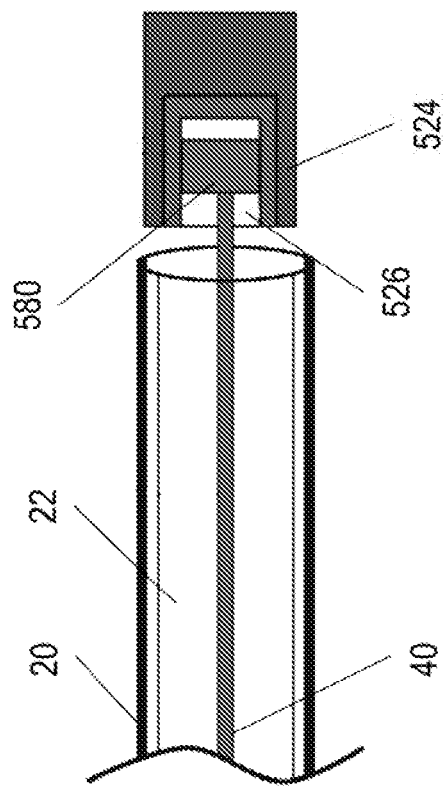

FIG. 52 illustrates a variation to the exemplary embodiment shown in FIGS. 48A-48B. Similar to what has been described in FIGS. 48A-48B, the engagement wire (40) also has an enlarged distal portion. Unlike what has been described in FIGS. 48A-48B, the enlarged distal end (580) of the engagement wire (40) is configured to frictionally engage the bracket engagement mechanism (524). To release the implant, the engagement wire (40) retracts proximally with sufficient force, thereby withdraw the enlarged distal end (580) of the engagement wire (40) from the bracket engagement mechanism (524).

Figure 53:
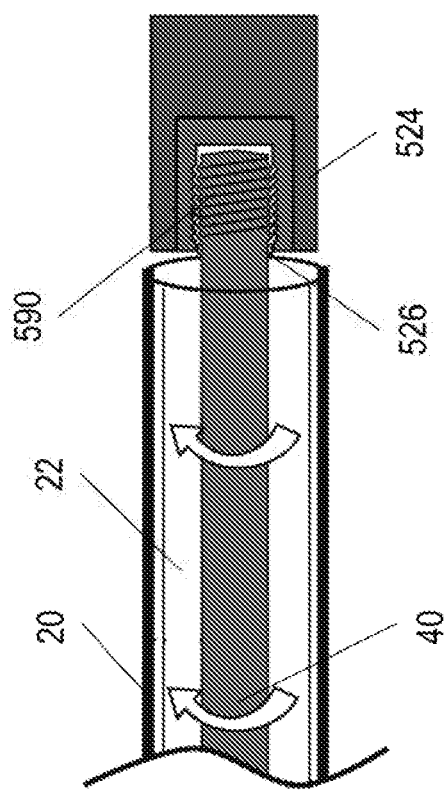
FIGS. 53-59 are perspective views of various exemplary engagement between a delivery system and a medical implant in accordance with the present teachings.

FIG. 53 illustrates another variation to the exemplary embodiment shown in FIG. 52. Similar to what has been described in FIG. 52, the engagement wire (40) also has an enlarged distal end (590). Unlike what has been described in FIG. 52, the enlarged distal end (590) of the engagement wire (40) is configured to threadably engage the bracket engagement mechanism (524). To release the implant, a clinician rotates the engagement wire (40), unthread the enlarged distal end (590) from the bracket engagement mechanism (524), triggering the engagement wire (40) retracts proximally.

Figure 54:
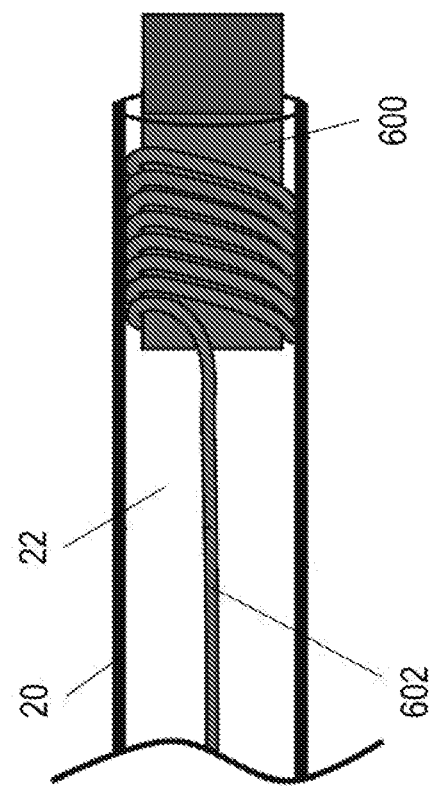

FIG. 54 illustrates another exemplary embodiment of the engagement of implant (80) and delivery system (10). As shown in FIG. 53, the proximal end portion (600) of the implant is wrapped with a distal portion of the engagement wire (602). Together they frictionally engages to a distal portion of the inner lumen of implant pusher shaft (20). In some embodiment, the engagement wire (602) is configured in such way that a retraction to the proximal end of engagement wire (602) would unwind the distal portion of the engagement wire (602) from the proximal end portion (600) of the implant. The proximal end portion (600) of the implant, free from the engagement wire (602) wrap, will then move freely out of the implant pusher shaft lumen.

Figure 55:
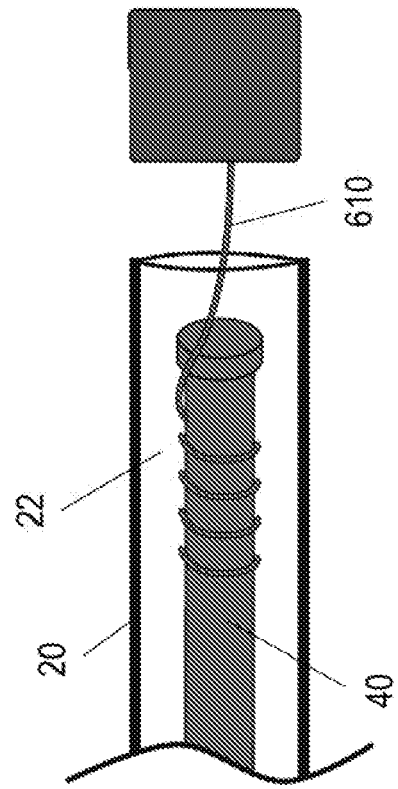

FIG. 55 illustrates another exemplary embodiment of the engagement of implant (80) and delivery system (10). As shown in FIG. 54, the implant has an engagement filament (610), for example similar to what has been described with reference to FIG. 3. Such engagement filament (610) wraps along a distal portion of the engagement wire (40), thereby engaging the implant to the delivery system (10). In one embodiment, the distal end of the engagement wire (40) has an enlarged portion which is configured to prevent the accidental unwinding of the engagement filament (610). To release the implant, the engagement wire (40) rotates in an unwinding direction causes engagement filament (610) to disengage from the engagement wire (40).

Figure 57:
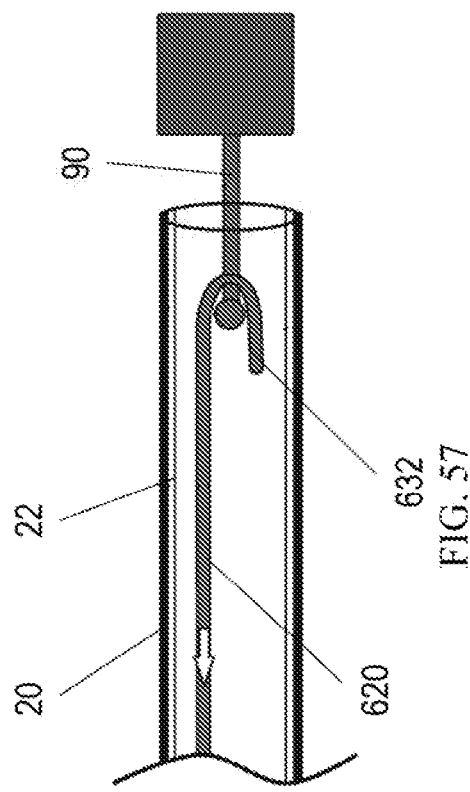
Figure 56:
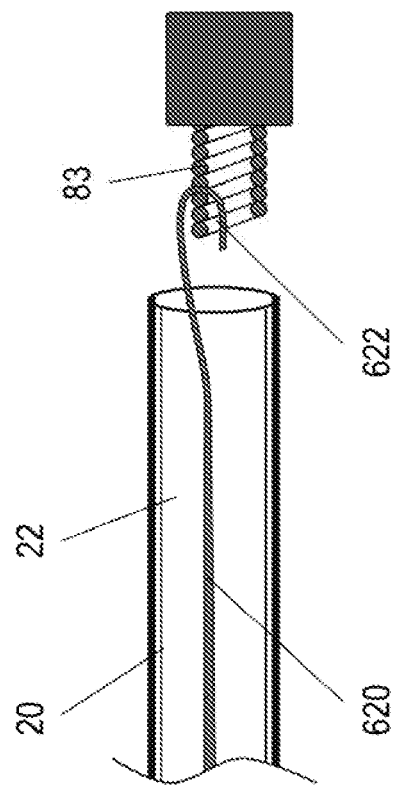

FIGS. 56-57 illustrate a couple exemplary embodiment of the hook-implant engagement mechanism. FIGS. 56-57 all show that the distal end of the engagement wire has a hook shaped engagement feature. In one embodiment, the hook shaped engagement feature has a curved profile configured to join a proximal portion of the implant, and a straighten profile configured to release the implant. The transition from the curved profile to the straightened profile is triggered by a proximal retraction of the engagement wire. In another embodiment, the hook shaped engagement feature only has a permanent curved profile which operably rotates to engage or disengage from the implant. FIG. 56 shows that the implant has a coiled proximal end, which is attached to the hook shaped engagement feature. In another embodiment, the hook shaped engagement feature (622) rotatably disengages from the implant. According to one embodiment, the hook shaped engagement feature (622) straightens its curved profile in order to release the implant. FIG. 57 shows that the hook shaped engagement feature (622) joins a proximal portion of the engagement filament (90) of the implant. According to one embodiment, the hook shaped engagement feature (632) straightens its curved profile in order to release the implant.

Figure 58:
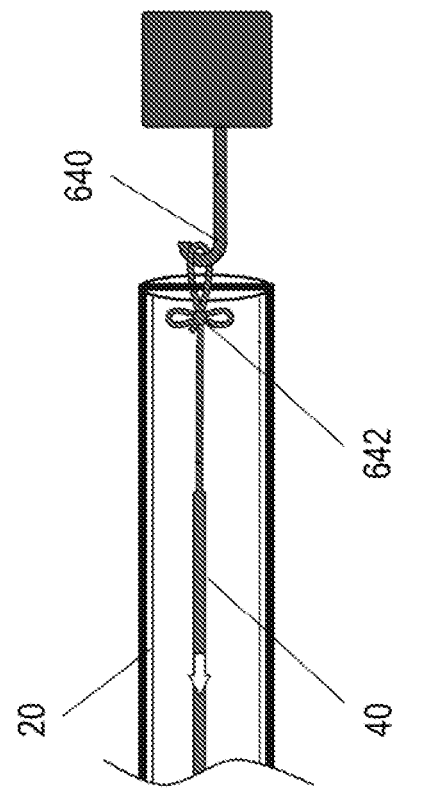

FIG. 58 illustrates another exemplary embodiment of the implant-delivery system engagement mechanism. FIG. 58 shows that the proximal end of implant has a hook shaped engagement feature (640). The distal end of the engagement wire (40) has an exploding knot (642). During delivery and deployment, the distal portion of the engagement wire (40) extends distally, the hook shaped engagement feature (640) of the implant engages the exploding knot (642). When the engagement wire (620) is pulled proximally, the exploding knot (642) unties itself. The implant is then released.

Figure 59:
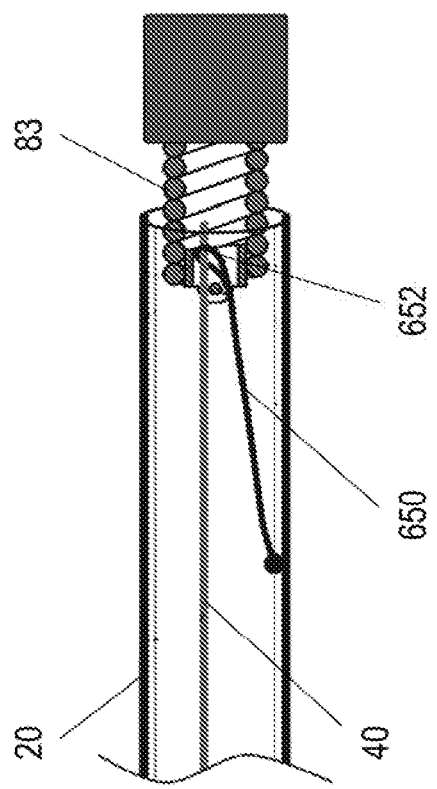

FIG. 59 illustrates another exemplary embodiment of the implant-delivery system engagement mechanism. FIG. 59 shows a second engagement filament (650) attaching to the inner luminal wall of the implant pusher shaft (20) at a distal location. The distal end of the second engagement filament (650) has a loop (652), sized and shaped to allow the distal end of the second engagement wire (40) to extend through. The proximal end of the coil implant (83) has a port and a cross pin (similar to the fingers and cross pin described above with reference to FIG. 4. During implant delivery and deployment, as shown in FIG. 59, the second engagement filament (650) extends distally into the proximal port of the implant from one side of the cross pin, the engagement wire (40) also extends distally into the proximal portion of the implant from the opposite side of the cross pin and further into the distal loop of the engagement filament (650), thereby secures the implant to the delivery system (10). To release the implant, the engagement wire (40) retracts proximally. The distal loop (652) of the engagement filament (650) is then released, and the implant is then set free.

Most embodiments of the implant-delivery system (10) engagement described above, with exceptions of embodiments referenced in FIGS. 8, 18, 21, 22, 24, 25, 27, 32, and 34, require a proximal retraction of the engagement wire (40) in order to fully release the implant. As described above, the proximal end of the engagement wire (40) fixedly attaches to an implant release control mechanism. The proximal retraction of the engagement wire (40) could be trigger by an actuation of the implant release control mechanism, for example, a proximal retraction. FIGS. 60-120 illustrate various embodiments of the implant release control mechanism and its control to the proximal retraction of the engagement wire. According to one embodiment, the implant release control mechanism is constructed and arranged to rapidly release implant, in order to avoid, or greatly reduce, delays between activation of control mechanism and release of implant.

FIGS. 60-90 illustrate various embodiment where the engagement/disengagement between the implant release control mechanism and implant pusher shaft is accomplished by a motion of the implant release control mechanism alone or in combination of a motion of the proximal end portion of the implant pusher shaft. FIGS. 60-80 illustrate various embodiments of the implant release control mechanism where it is a separate component from the implant pusher shaft, and it joins the proximal end of the engagement wire. FIGS. 81-84 illustrate another various embodiments of the implant release control mechanism which is an integral segment of the proximal end portion of the engagement wire. FIGS. 85-90 illustrate another various embodiments where the disengagement between the implant release control mechanism and the implant pusher shaft that involves a shape transformation of the proximal end portion of the implant pusher shaft. FIGS. 91-110 illustrate another various embodiments where the implant release control mechanism is a breakable proximal portion of the implant pusher shaft.

Referring to FIG. 60, the implant release control mechanism removably attaches to the implant pusher shaft (20) via a connector. As shown in FIG. 60, the connector in a general tubular profile joins the proximal end (24) of the implant pusher shaft (20), and the distal end (36) of the implant release control mechanism (30). In one embodiment, the implant release control mechanism (30) also has a general cylindrical profile. The connector (12) fixedly joins the proximal end (24) of the implant pusher shaft (20), and frictionally joins the distal end (36) of the implant release control mechanism (30). To disengage the implant release control mechanism (30) from the implant pusher shaft (20), the implant release control mechanism (30) is removed from the connector (12) triggering a proximal retraction of the engagement wire (40). In one embodiment, the connector (12) is a tube made of PTFE and/or PET. In another embodiment, the connector (12) engages to the proximal end (24) of the implant pusher shaft (20) via various thermal, chemical or mechanical mechanism known in the field such as adhesive, welding, crimp, and/or swage.

FIG. 61 illustrates another embodiment of the implant release control mechanism (30) removably attaching to the implant pusher shaft (20) via a connector. As shown in FIG. 61, the implant release control mechanism (30) has a general cylindrical profile. The proximal end portion (21) of the implant pusher shaft (20) has an inner lumen (23) which is sized and shaped to frictionally engage a distal portion (35) of the implant release control mechanism (30). During implant delivery and deployment, the implant release control mechanism (30) extends into the inner lumen (23) of the implant pusher shaft (20) from its proximal end and engages the inner lumen (23) of the proximal end portion (21) of the implant pusher shaft (20). A proximal portion (33) of the implant release control mechanism (30) remains outside of the proximal end (24) of the implant pusher shaft (20) for a clinician to grasp. To actuate implant release, a clinician simply holds the implant pusher shaft (20) steady while pulls the implant release control mechanism (30) proximally with sufficient force.

FIGS. 62A-62B illustrate another embodiment of the implant release control mechanism (700). As shown in FIG. 62A, the implant release control mechanism (30) has a general cylindrical profile. A friction increasing ring (702) is positioned within the lumen (22) of the implant pusher shaft (20) near its proximal end portion. In one embodiment, the friction increasing ring (702) fixedly attaches to the inner luminal surface (704) of the implant pusher shaft (20). The ring (702) could be an O-ring or other structure, and/or material that is capable to frictionally engage the implant release control mechanism (700). In another embodiment, the friction increasing ring (702) attaches to the inner luminal surface (704) of the implant pusher shaft (20) through thermal, chemical, and mechanical means known in the field. During implant delivery and deployment, the implant release control mechanism (700) extends into the inner lumen (22) of the implant pusher shaft (20) from its proximal end, and engages the friction increasing ring (702). A proximal portion of the implant release control mechanism (700) remains outside of the proximal end (24) of the implant pusher shaft (20) for a clinician to grasp. With sufficient pulling force that overcomes the frictional engagement with the ring (702), the implant release control mechanism (700) disengages the implant pusher shaft (20) as shown in FIG. 62B.

Figure 63A:
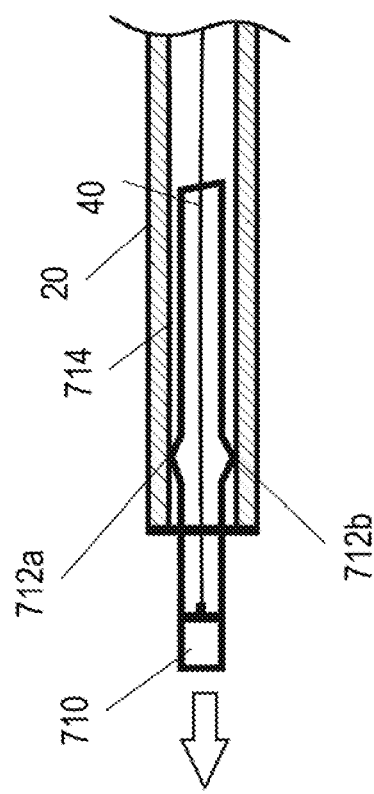
Figure 63B:
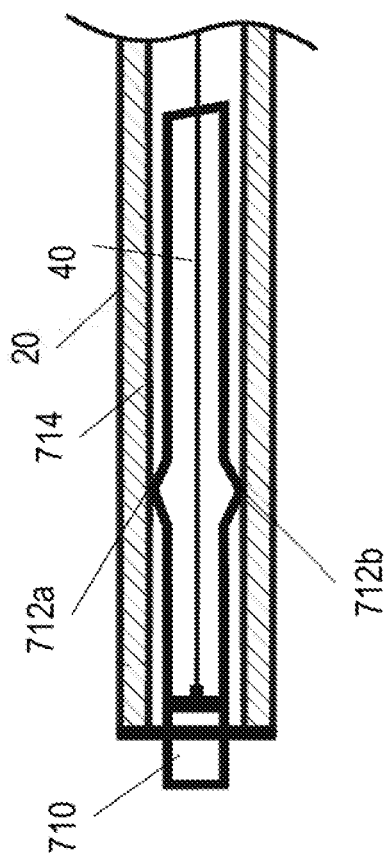

FIGS. 63A-63B illustrate another embodiment of the implant release control mechanism (710). As shown in FIG. 63A, the implant release control mechanism (710) has a general cylindrical profile with one or more radial projections (712a, 712b). The projections (712a, 712b) are configured to frictionally engage to the inner luminal surface (714) of the implant pusher shaft (20). With sufficient pulling force that overcomes the frictional engagement between the projections (712a, 712b) and the inner luminal surface (714) of the implant pusher shaft (20), the implant release control mechanism (710) disengages the implant pusher shaft (20) as shown in FIG. 63B.

Figure 64A:
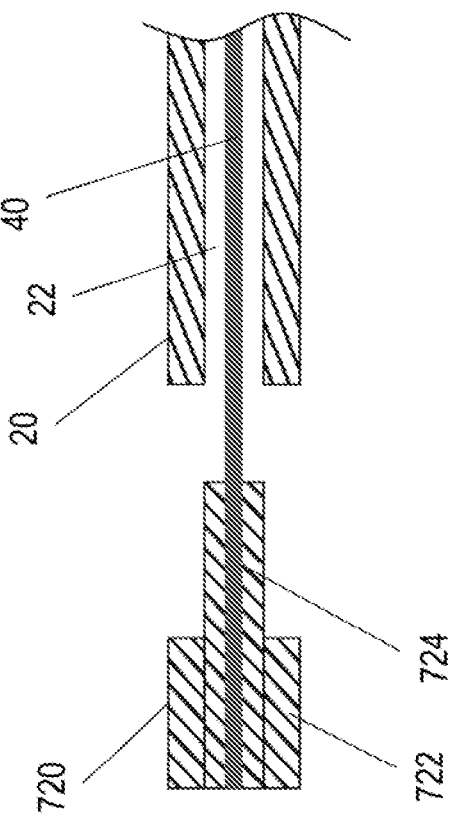
Figure 64B:
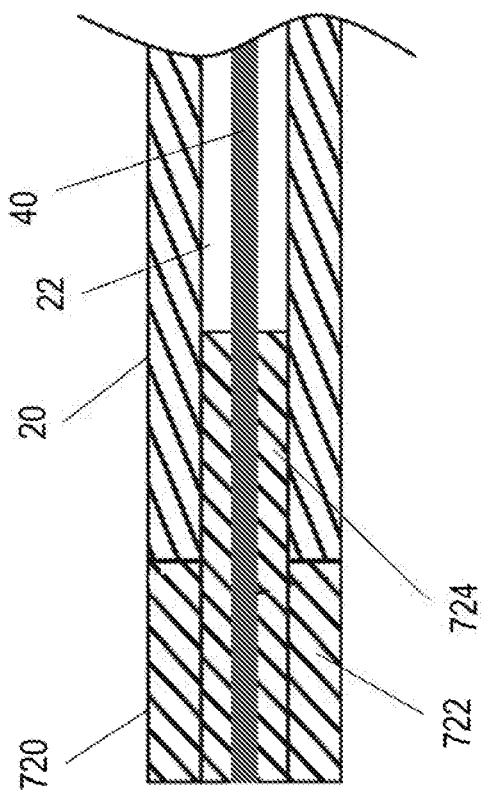

FIGS. 64A-64B illustrate another embodiment of the implant release control mechanism (720). As shown in FIG. 64A, the implant release control mechanism (720) has a stepped cylindrical profile with its proximal portion (722) having a larger diameter and its distal portion (724) having a smaller diameter. The distal portion (722) of the implant release control mechanism (720) is configured to frictionally engage the inner lumen (22) of the implant pusher shaft (20) at its proximal end portion. The larger diameter proximal portion of the implant release control mechanism (720) prevents any further advancement of the implant release control mechanism (720) into the implant pusher shaft lumen. In one embodiment, at least one of the distal portion (724) of the implant release control mechanism (720) and the inner luminal wall of the proximal portion of the implant pusher shaft (20) is made of a material with a high coefficient of friction, such as a polymer, in order to prevent accidental disengagement between the implant release control mechanism (720) and the implant pusher shaft (20). To actuate implant release, a clinician simply holds the implant pusher shaft (20) steady while pulls the implant release control mechanism (720) proximally with sufficient force as shown in FIG. 64B.

Figure 65A:
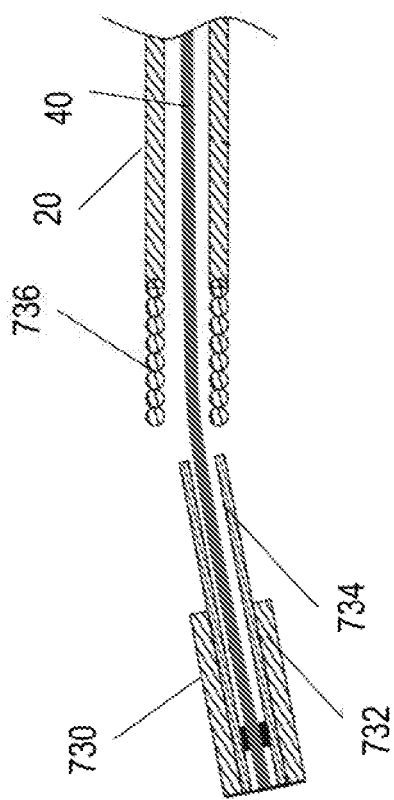
Figure 65B:
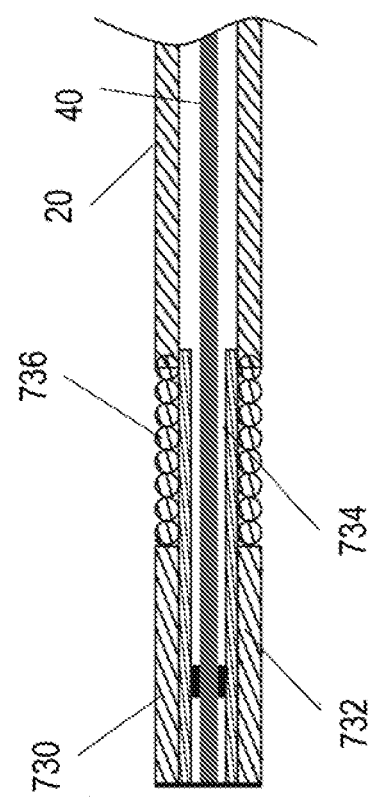

FIGS. 65A-65B illustrate a variation to the exemplary embodiment shown in FIGS. 64A-64B. Similar to what has shown in FIG. 64A, the implant release control mechanism (730) has a stepped cylindrical profile with a larger proximal portion (732) and a smaller distal portion (734). Unlike what has shown in FIG. 64A, the implant pusher shaft (20) has a coiled proximal end portion (736). During implant delivery and deployment, the smaller distal portion (734) of the implant release control mechanism (730) frictionally engages the inner lumen of the coiled proximal end portion (736) of the implant pusher shaft (20). With sufficient pulling force, the implant release control mechanism (730) disengages the implant pusher shaft (20) as shown in FIG. 65B.

Figure 66A:
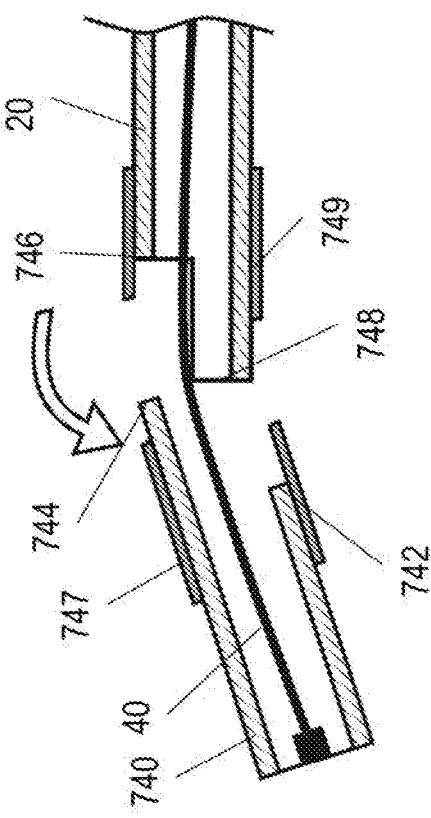
Figure 66B:
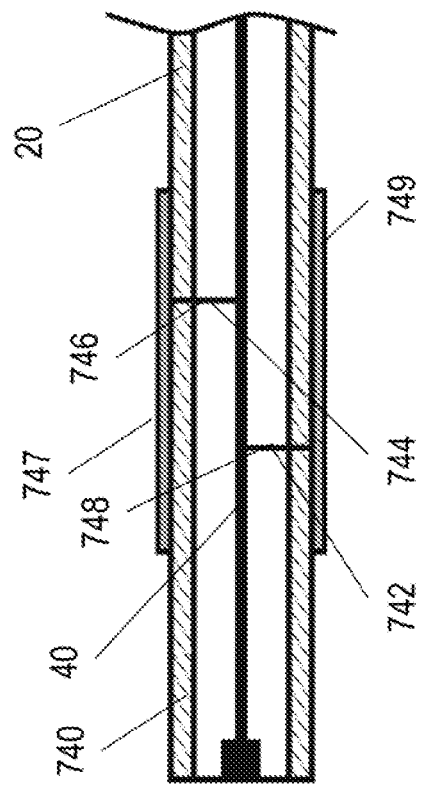

FIGS. 66A-66B illustrate a variation to the exemplary embodiment shown in FIG. 60. Similar to what has shown in FIG. 60, the implant release control mechanism (740) removably attaches to the implant pusher shaft (20). Unlike what has shown in FIG. 60, the implant release control mechanism (740) has a distal end in an "L" shape with a shorter distal end (742) and a longer distal end (744), and the implant pusher shaft (20) has a proximal end in a matching "L" shape also with a shorter proximal end (746) and a longer proximal end (748). A proximal connector (747) fixedly joins the distal portion of the implant release control mechanism (740) with a part of the proximal connector (747) extends beyond the shorter distal end (742) of the implant release control mechanism (740); a distal connector (749) fixedly joins the proximal portion of the implant pusher shaft (20) with a part of the distal connector (749) extends beyond the shorter proximal end (746) of the implant release control mechanism (740). During implant delivery and deployment, as shown in FIG. 66A, the "L" shaped distal end of the implant release control mechanism (740) joins the "L" shaped proximal end (24) of the implant pusher shaft (20). The longer distal end (744) of the implant release control mechanism (740) frictionally joins the distal connector (749) that extends beyond the shorter proximal end (746) of the implant pusher shaft (20). And the longer proximal end (748) of the implant pusher shaft (20) frictionally joins the proximal connector (747) that extends beyond the shorter distal end (742) of the implant release control mechanism (740). To actuate the implant release control mechanism (740), with sufficient pulling force, the implant release control mechanism (740) disengages the implant pusher shaft (20) as shown in FIG. 66B.

Figure 67:
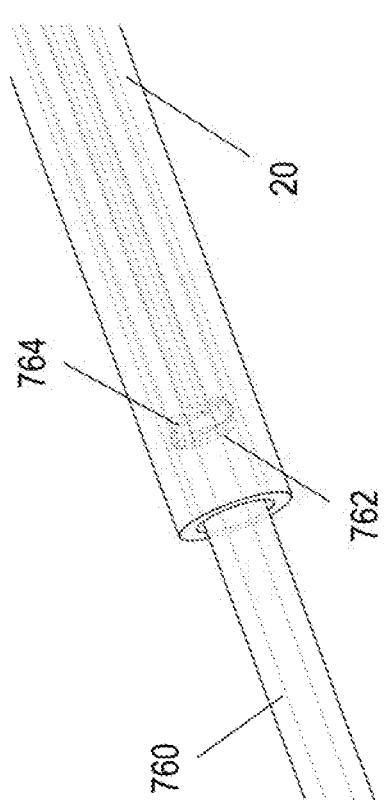

FIG. 67 illustrates another embodiment of the implant release control mechanism (750). As shown in FIG. 67, the implant release control mechanism (750) also has a general cylindrical profile. The distal end of the implant release control mechanism (750) has a projection (752), such as a pin. The projection is configured to be slidingly received by a recess (754) at the proximal end (24) of the implant pusher shaft (20). Such ping recess connection has a first configuration where the projection (752) engages the recess (752), and the implant release control mechanism (750) is prevented from retracting proximally. Such pin-recess connection also has a second configuration where the projection is freed from the recess, and the implant release control mechanism (750) is now ready to move away from the implant pusher shaft (20). In one embodiment, for example, the disengagement between the implant release control mechanism (750) and the implant pusher shaft (20) is accomplished by a simple rotation.

Figure 68:
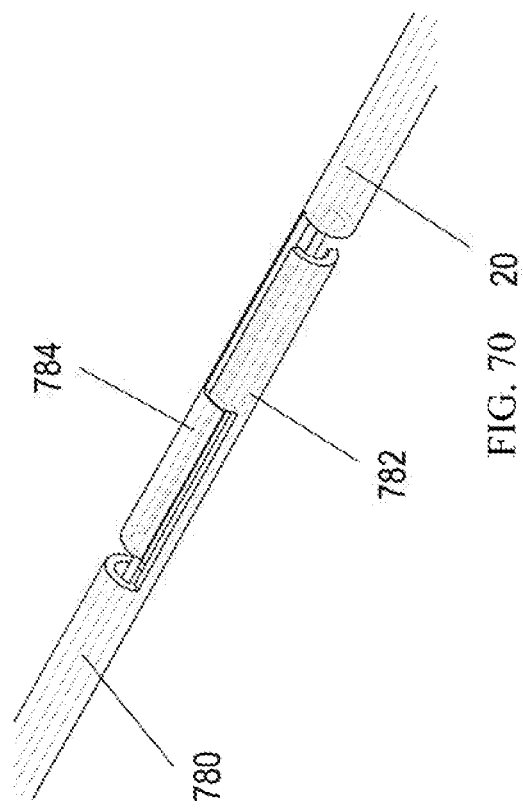

FIG. 68 illustrates a variation to the exemplary embodiment shown in FIG. 67. Similar to what has shown in FIG. 67, the implant release control mechanism (760) removably engages to the proximal end of the implant pusher shaft (20) in a pin-recess configuration having a first engaged profile and a second disengaged profile. Unlike the exemplary embodiment shown in FIG. 67, the projection (764) is at the proximal end of the implant pusher shaft (20), and the recess (762) is at the distal end of the implant release control mechanism (760).

Figure 69:
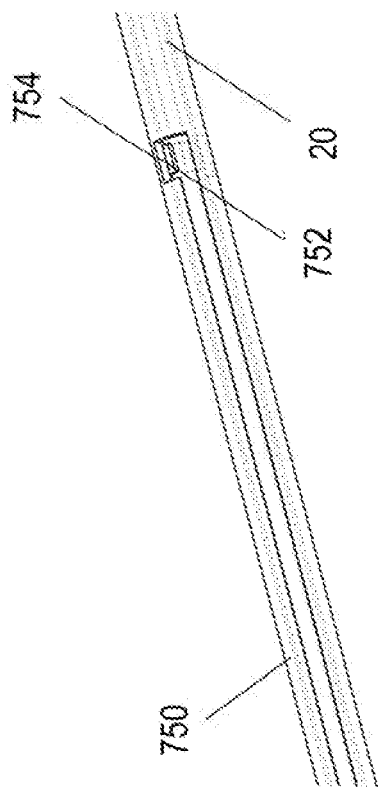

FIG. 69 illustrates a variation to the exemplary embodiment shown in FIG. 67. Similar to what has shown in FIG. 67, the implant release control mechanism (770) removably engages to the proximal end of the implant pusher shaft (20) in a pin-recess configuration having a first engaged profile and a second disengaged profile. The projection/pin (772) is at the distal end of the implant release control mechanism (770) and the recess (774) is at the proximal end (24) of the implant pusher shaft (20). Unlike the exemplary embodiment shown in FIG. 67, the disengagement between the implant release control mechanism (770) and the implant pusher shaft (20) is accomplished by first advancing, and then rotating of the implant release control mechanism (770). Upon doing so, the implant release control mechanism (770) can now be retracted proximally.

Figure 70:
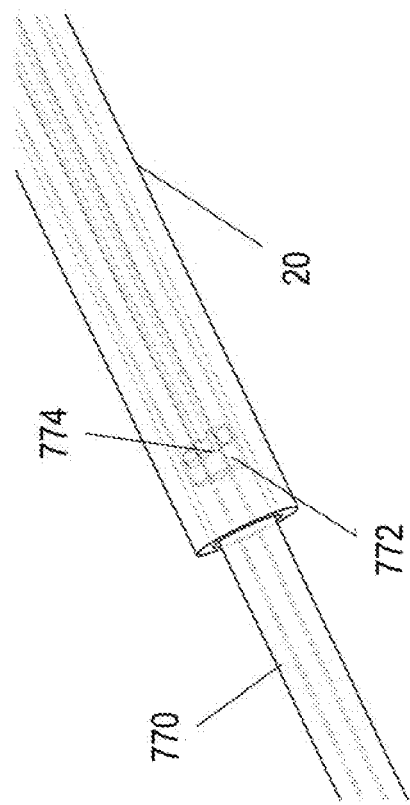

FIG. 70 illustrates a variation to the exemplary embodiment shown in FIG. 68. Similar to what has shown in FIG. 68, the implant release control mechanism (780) removably engages to the proximal end (24) of the implant pusher shaft (20) in a pin-recess configuration having a first engaged profile and a second disengaged profile. The projection/pin is at the proximal end (24) of the implant pusher shaft (20) and the recess is at the distal end of the implant release control mechanism (780). Unlike the exemplary embodiment shown in FIG. 68, to disengage the implant release control mechanism (780) from the distal end (26) of the implant pusher shaft (20), a clinician rotates the implant release control mechanism (780) first followed by another rotation of the implant pusher shaft (20).

Figure 71A:
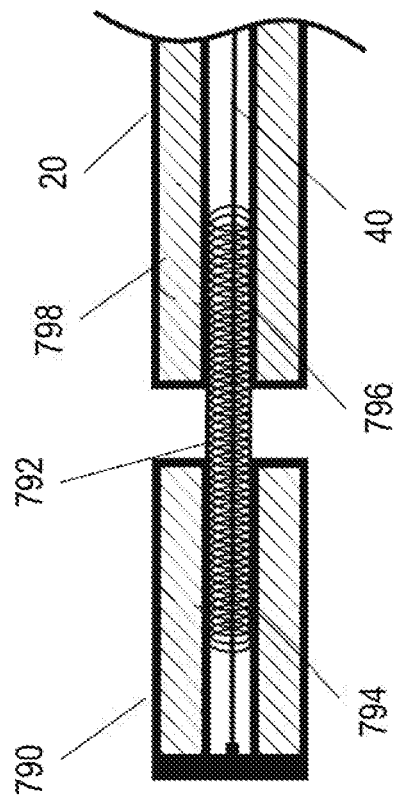
Figure 71B:
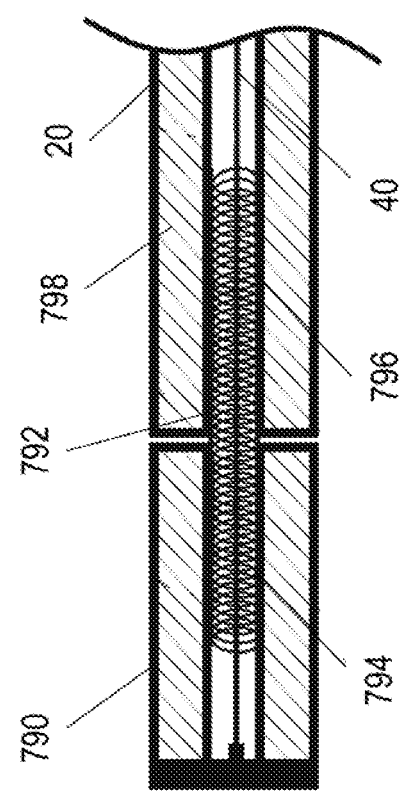

FIGS. 71A-71B illustrate another embodiment of the implant release control mechanism (790). As shown in FIG. 71A, the implant release control mechanism (790) has an inner lumen with a coil (792) partially fit inside the lumen. A proximal portion (794) of the coil (792) extends into the inner lumen of the implant release control mechanism (790), from its distal opening, and fixedly attaches to the implant release control mechanism (790). A distal portion (796) of the coil (792) remains outside of the implant release control mechanism (790). The distal portion (796) of the coil (792) is configured to releasably attach to an inner lumen (22) of the implant pusher shaft (20) at its proximal end portion (798). During implant delivery and deployment, as shown in FIG. 71A, the distal portion (796) of the coil (792) slides into the proximal end portion (798) of the implant pusher shaft (20) inner lumen. In one embodiment, the distal portion (796) of the coil (792) frictionally engages the implant pusher shaft (20). To actuate implant release, the implant release control mechanism (790) is pulled with sufficient force. In some embodiments, the retraction of the implant release control mechanism (790) causes a plastic or elastic deformation of the coil (792). In another embodiment, the distal portion (796) of the coil (792) threadably engages the implant pusher shaft (20). As such, the inner luminal wall of the implant pusher shaft (20) could have an inner threads to receive the coil (792). Alternatively, the inner luminal wall of the implant pusher shaft (20) could have sufficient softness so that as the coil (792) threads in, it carves and engages the soft inner wall of the implant pusher shaft (20). To actuate implant release, a clinician rotates the implant release control mechanism (790), thereby allowing the coil (792) to detach the implant release control mechanism (790).

In an alternative embodiment, although not shown in these figures, the distal end of the implant release control mechanism joins a proximal coil, the proximal end (24) of the implant pusher shaft (20) joins a distal coil. During implant delivery, the proximal and distal coil threadably engages each other. To actuate implant release, a clinician rotates the implant release control mechanism, thereby allowing the proximal coil to detach the distal coil.

Figure 72A:
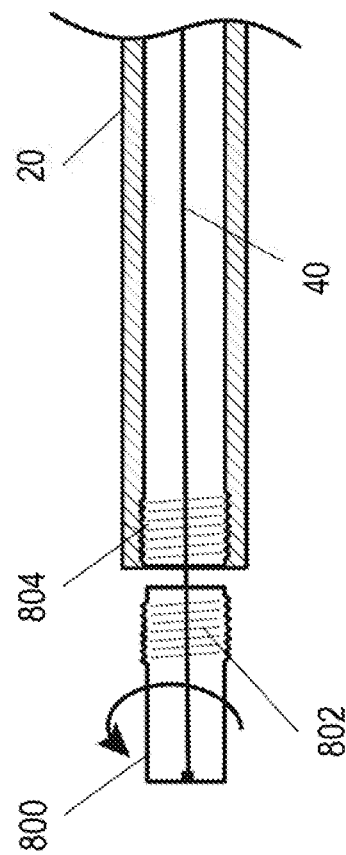
Figure 72B:
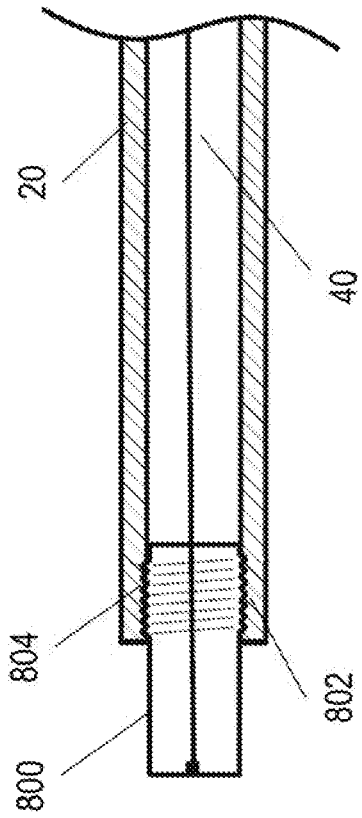

FIGS. 72A-72B illustrate another embodiment of the implant release control mechanism (800). As shown in FIG. 72A, the implant release control mechanism (800) has a general cylindrical profile. The distal portion of the implant release control mechanism (800) has an engagement threads (802) which are configured to engage the mating threads (804) at a proximal end portion of the implant pusher shaft (20). As the mating threads engages each other, the implant release control mechanism (800) engages the implant pusher shaft (20). In one embodiment, a release of the implant from the delivery system (10) is achieved when mating threads completely detaches from each other. In another embodiment, a release of the implant from the delivery system (10) is achieved even when mating threads remains partially attached.

FIGS. 60-72 illustrate various embodiments of the implant release control mechanism having a general elongated (such as cylindrical, or stepped cylindrical) profile. The proximal end of the engagement wire joins the implant release control mechanism through thermal, chemical, or mechanical mean known in the field. In one embodiment, the engagement wire joins the implant release control mechanism at its proximal end, such as most embodiments shown in FIGS. 60-72. In another embodiment, the implant release control mechanism has an inner lumen with a proximal cap. The proximal end of the engagement wire extends into the inner lumen of the implant release control mechanism, and joins its proximal cap, such as shown in FIGS. 63A-63B. In yet another embodiment, the engagement wire extends into the inner lumen of the implant release control mechanism and joins the inner lumen of the implant release control mechanism at a place such as shown in FIGS. 65A-65B.

Figure 73B:
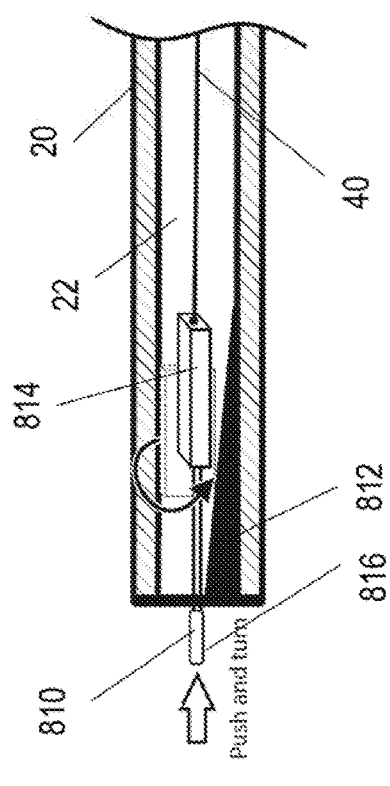
Figure 73A:
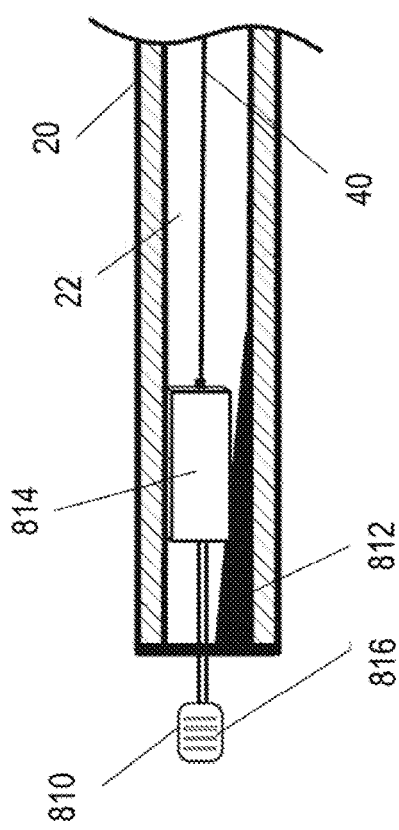

FIGS. 73A-73B illustrate another embodiment of the implant release control mechanism. As shown in FIG. 73A, the proximal end portion of the implant pusher shaft (20) has a blocking element (812), such as a wedge, fixedly attaches to the inner lumen (22) of the implant pusher shaft (20). This blocking element (812) narrows the general diameter of the proximal opening of the implant pusher shaft (20) in one orientation, while allows the general diameter of the proximal opening of the implant pusher shaft (20) unchanged in a second orientation. FIG. 73A further shows that the proximal end of the engagement wire (40) joins a plug (814) configured to engage/disengage the blocking element (812). A grasp element (816) joins the proximal end of the plug (814). In one embodiment, as shown in FIG. 73A, the plug (814) has an asymmetric shape, such as a shape of a rectangular prism with a width of its cross section less than its height. The height of the plug (814) is sized to be greater than narrowed diameter of the implant pusher shaft (20) in its first orientation, while smaller than unchanged diameter of the implant pusher shaft (20) in its second orientation. This allows the plug (814) to be blocked from moving proximally outside of the implant pusher shaft (20) during implant delivery and deployment. The width of the plug (814) is sized to be smaller than all diameter of the implant pusher shaft (20) opening in both first and second orientations. The grasp element (816) joins the proximal end of the plug (814), configured to be held by a clinician in order to advance, retract, and rotate the plug. During implant delivery and deployment, the plug (814) is positioned in such way as shown in FIG. 73A, with its height fit and blocked in between the blocking element (812) and the opposite luminal wall in the first orientation. To release the implant, a clinician rotates the grasp elements (816) causing the plug to turn about 90°, as shown in FIG. 73B. Then, the grasp element (816), the plug (814), and the engagement wire (40) can be retracted proximally.

Figure 74B:
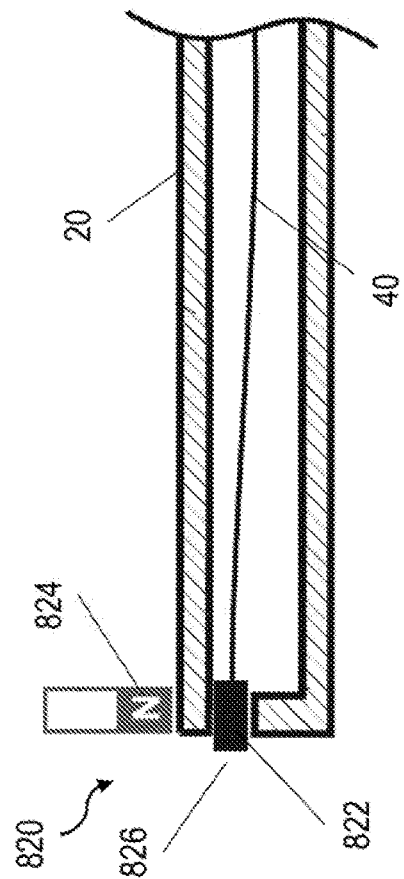
Figure 74A:
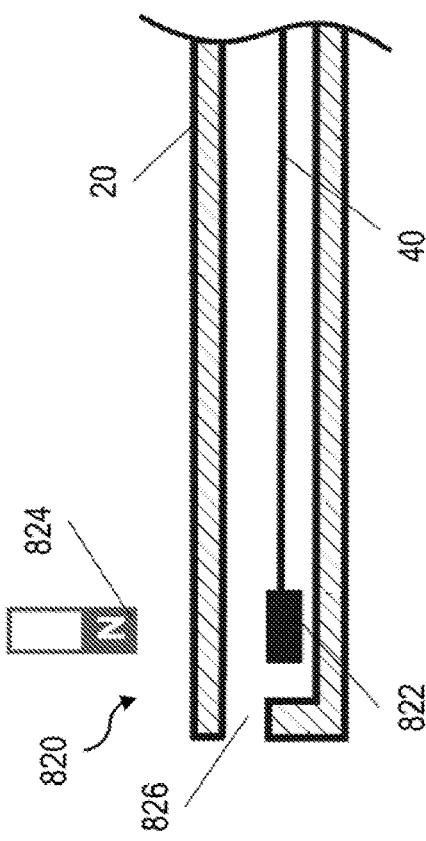

FIGS. 74A-74B illustrate another embodiment of the implant release control mechanism (820). As shown in FIG. 74A, the proximal end (24) of the implant pusher shaft (20) has a proximal opening (826). The implant release control mechanism (820) in the configuration of a magnetic element (822) fixedly joins the proximal end of the engagement wire (40). A second magnetic element (824) with opposite pole positioned adjacent to the outer surface of the implant pusher shaft (20) is used to manipulate the movement of the engagement wire (40). Two magnetic elements (822, 824) interacts with each other through the wall of implant pusher shaft (20), allowing proximal retraction or distal extension of the engagement wire (40). The interaction between the two magnetic elements (822, 824) would also lead the magnetic element (822) attached at the proximal end of the engagement wire (40) exit the proximal opening of the implant pusher shaft (20), such as shown in FIG. 74B. In some embodiments, magnetic elements (822, 824) are made of magnetic material, magnetized material, or non-magnetized ferromagnetic material, such as iron in a non-magnetized state. In another embodiments, the two interaction magnetic elements (822, 824) have attracting poles such as north or South Pole shown in FIG. 74A.

Figure 75A:
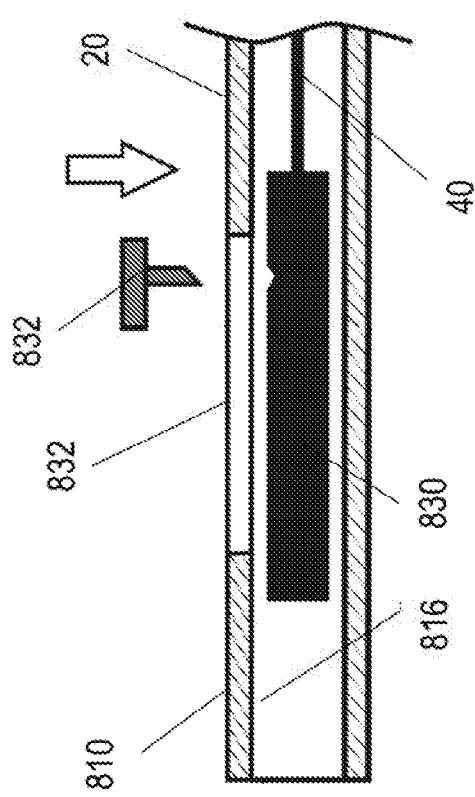
Figure 75B:
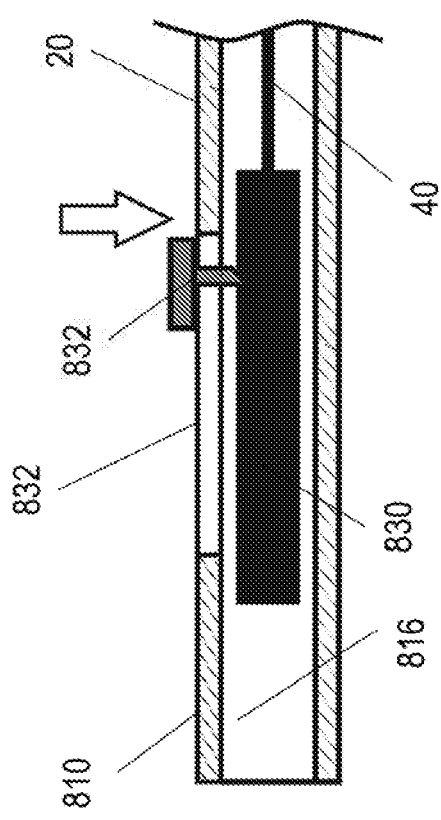

FIGS. 75A-75B illustrate another embodiment of the implant release control mechanism (830). As shown in FIG. 75A, the proximal end portion of the implant pusher shaft (20) has a sliding slot (832) along its luminal surface. The implant release control mechanism (830) joining the proximal end of the engagement wire (40) has a recess configured to align with the sliding slot (832). A projection (834) configured to engage the recess on the implant release control mechanism (830). As shown in FIG. 75A, the projection (834) is positioned within the sliding slot (832). The implant release control mechanism (830) has a first position where the projection (834) is at a relative distal location within the sliding slot (832). The implant release control mechanism (830) has a second position where the projection (834) is at a relative proximal location within the sliding slot (832). The projection (834) is configured to be actuated by a clinician in order to transfer the implant release control mechanism (830) from its first position to its second portion. In one embodiment, the implant release control mechanism (830) frictionally engages the inner lumen (22) of the implant pusher shaft (20) at its first position, while the projection (834) is used to apply a proximal pulling force in order to transfer the implant release control mechanism (830) to its second position. In another embodiment, the implant release control mechanism (830) is secured to its first position by the projection (834) being secured, such as "being trapped or locked" within the sliding slot (832), and the proximal movement of the projection (834) transfers the implant release control mechanism (830) to its second position. In another embodiment, the implant release control mechanism (830) is secured to its second position by the projection (834) being secured, such as "being trapped or locked" within the sliding slot (832), and the distal movement of the projection (834) transfers the implant release control mechanism (830) to its first position.

Figure 76A:
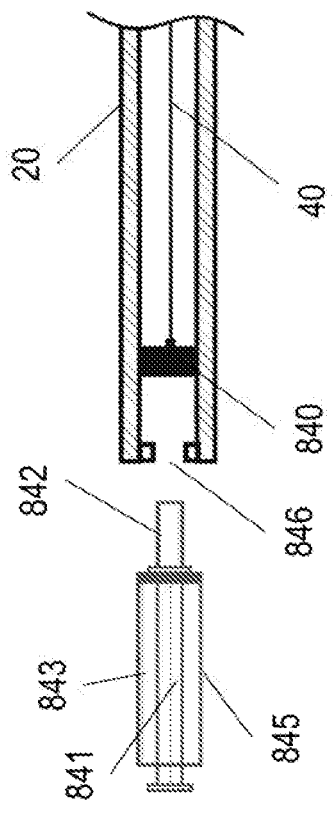
Figure 76B:
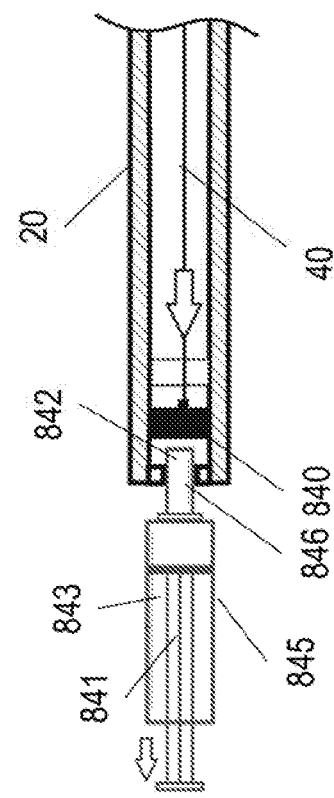

FIGS. 76A-76B illustrate another embodiment of the implant release control mechanism (840). As shown in FIG. 76A, the implant release control mechanism (840) in the shape of a plug fixedly joins the proximal end of the engagement wire (40). The implant pusher shaft (20) has a proximal opening (846) sized and configured to fit a syringe nozzle (842). The plug (840) frictionally engages the inner lumen (22) of the implant pusher shaft (20). The implant release control mechanism (840) has a first position where the plug (840) is at a relative distal location within the inner lumen (22) of the implant pusher shaft (20), and a second position where the plug (840) is at a relative distal location within the inner lumen (22) of the implant pusher shaft (20). A syringe (845) with its plunger (841) and barrel (843) collapsed together, and its nozzle (842) engages the proximal opening of the implant pusher shaft (20), forming a hermetic seal within the inner lumen of the pusher shaft (20) proximal to the plug (840). The plunger (841) is then pull proximally creates a vacuum inside the implant pusher shaft lumen. Such vacuum leads to a proximal motion of the plug (840) thereby transports the implant release control mechanism (840) to its second position.

Figure 77A:
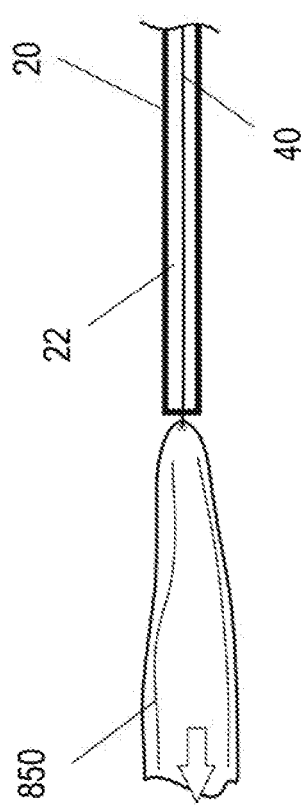
Figure 77B:
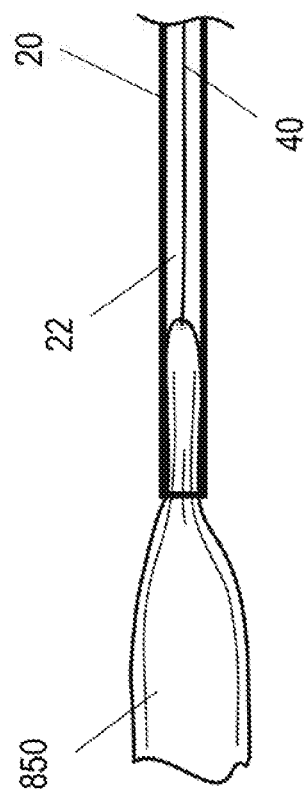

FIGS. 77A-77B illustrate another embodiment of the implant release control mechanism (850). As shown in FIG. 77A, the implant release control mechanism (850) in the shape of collapsible plug (850) fixedly joins the proximal end of the engagement wire (40). In one embodiment, the plug is made of flexible materials such as silicone, low durometer PEBAX, urethane, latex. During implant delivery and deployment, the plug (850) collapses, and frictionally engages the implant pusher shaft lumen (22) at its proximal end. To actuate implant release, the implant release control mechanism (850) retracts proximally and disengages the implant pusher shaft (20).

Figure 78A:
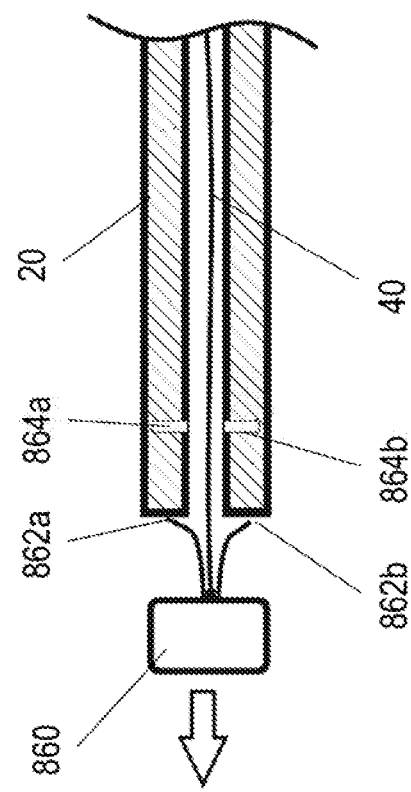
Figure 78B:
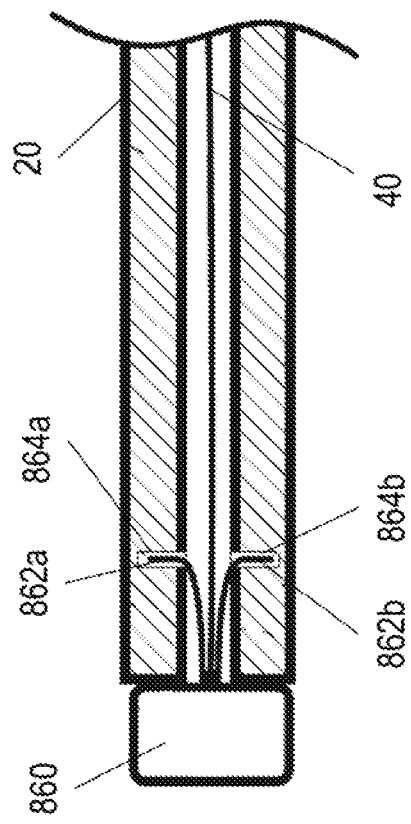

FIGS. 78A-78B illustrate another embodiment of the implant release control mechanism. As shown in FIG. 78A, the implant release control mechanism has a plug (860) with at least two collapsible arms (862a, 862b) configured to engage the implant pusher shaft lumen. The plus (860) fixedly joins to the proximal end of the engagement wire (40). In one embodiment, the at least two arms (862a, 862b) joins the distal end of the plug (860). The at least two arms (862a, 862b) has a radially expanded configuration and a radially collapsed configuration. In one embodiment, the at least two arms (862a, 862b) are made of a plastic material, a shape memory filaments, a superelastic filaments, stainless steel, nickel titanium alloy, cobalt-chromium, and/or other suitable material known in the field. FIG. 78A also shows that implant pusher shaft (20) has a plurality of recesses (864a, 864b) within its proximal end portion of the inner lumen. The number and profile of the recess (864a, 864b) matches the number and profile of the collapsible arms (862a, 862b) of the implant release control mechanism (860). During implant delivery and deployment, as shown in FIG. 78A, the arms (862a, 862b) position inside the recess (864a, 864b), allowing the implant release control mechanism (860) engage to the implant pusher shaft (20). In one embodiment, the collapsible arms (862a, 862b) are configured in such a way that a proximal retraction to the plug (860), would force the arms (862a, 862b) to collapse radially, and disengage from the recess (864a, 864b) as shown in FIG. 78B.

FIGS. 79A-79B illustrate a variation to the exemplary embodiment shown in FIGS. 78A-78B. Similar to what has shown in FIGS. 78A-78B, the implant release control mechanism has a plug (870) with at least two collapsible arms (872a, 872b) configured to engage the implant pusher shaft lumen (22). And the plug (870) fixedly joins to the proximal end of the engagement wire (40). Unlike what has shown in FIGS. 78A-78B, the proximal end portion of the implant pusher shaft (20) does not have recess to receive the arms (872a, 872b) of the implant release control mechanism. Instead, the arms (872a, 872b) are configured to frictionally engage the inner luminal wall (874) of the implant pusher shaft (20). To actuate implant release, the clinician simply retracts the implant release control mechanism plug (870) proximally, causing the arms (872a, 872b) to collapse radially and slides proximally.

FIGS. 80A-80B illustrate another embodiment of the implant release control mechanism (880). As shown in FIG. 80A, the implant release control mechanism (880) has a collapsible plug (880a, 880b) fixedly joins the proximal end of the engagement wire (40). The collapsible plug (880a, 880b) has at least two segments. The collapsible plug (880a, 880b) has a radially expanded profile with the at least two plug segments (880a, 880b) radially expanded so as to frictionally fit inside the implant pusher shaft luminal surface (884) and stable the engagement wire (40). The collapsible plug (880a, 880b) has a radially collapsed profile with the at least two plug segments (880a, 880b) radially contracts so that they could move freely inside the implant pusher shaft lumen (22). In one embodiment, a plurality of pull wires (882a, 882b), each with its distal end fixed joining a plug segment (880a, 880b), and all its proximal ends joining together, and under the control of a clinician. During implant delivery and deployment, the expanded plug segments (880a, 880b) engages implant pusher shaft (20) inner lumen. As the clinician pulls the pull wires (882a, 882b) proximally, the plug segments (880a, 880b) collapse radially, and disengage the implant release control mechanism (880) from the implant pusher shaft (20) as shown in FIG. 80B. In one embodiment, although not shown in FIGS. 80A-80B, the inner lumen (22) of the implant pusher shaft (20) could have one or more recesses configured to receive plug segments (880a, 880b).

FIGS. 60-80 illustrate various embodiments of the implant release control mechanism. In these exemplary embodiments, the implant release control mechanism is a separate component from the implant pusher shaft, has a different construct than the engagement wire, and is fixedly joins the proximal end of the engagement wire. During implant delivery and deployment, the implant release control mechanism engages a proximal end portion of the implant pusher shaft. To actuate implant release, the implant release control mechanism disengages the implant pusher shaft either by a liner retraction motion, a rotational motion, or a combination of both. In all these embodiments, the implant release control mechanism maintain its shape and profile the entire time.

FIGS. 81-84 illustrate another various embodiments of the implant release control mechanism which is an integral segment of the proximal end portion of the engagement wire. In one embodiment, the proximal end portion of the engagement wire is configured with a first profile that prevents any distal movement of the rest portion of the engagement wire, and a second profile that allows free movement of the rest portion of the engagement wire.

Figure 81:
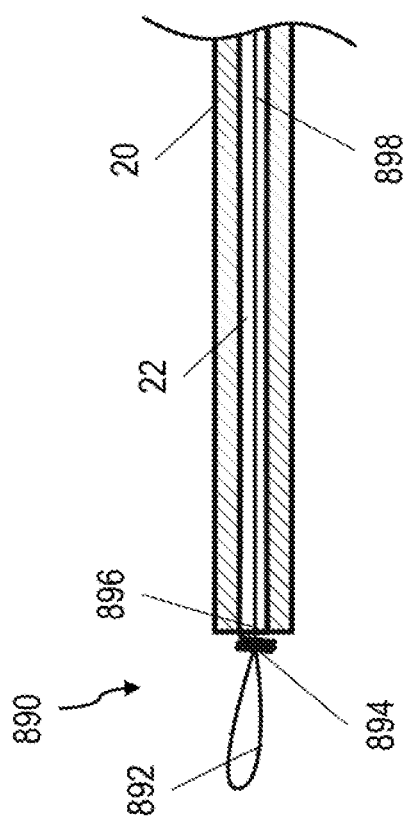

FIG. 81 illustrates another embodiment of the implant release control mechanism (890). As shown in FIG. 81, the implant release control mechanism (890) is the proximal end portion of the engagement wire (898) made into a grasping loop (892). In one embodiment, the grasping loop (892) is sized to be larger than proximal opening (896) of the implant pusher shaft (20), and stops further distal advancement of the loop (892) into the implant pusher shaft lumen (22). The gasping loop (892) allows the clinician to pull the engagement wire (40) proximally. And such proximal force applied by the clinician causes a proximal retraction of engagement wire (898). One skilled in the art should understand that grasping loops could adopt many shape and geometry so long as its intended purpose achieved.

Figure 82B:
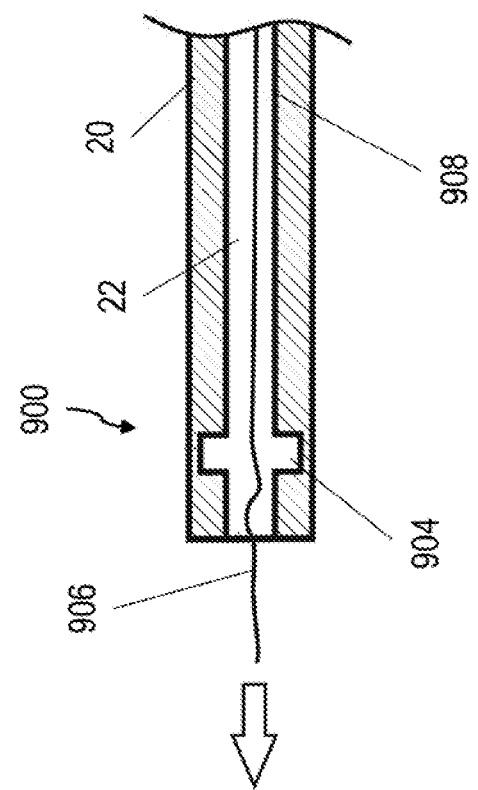
FIGS. 81-84 are perspective views of various exemplary implant release control mechanism where it is an integral segment of the proximal end portion of the engagement wire in accordance with the present teachings.
Figure 82A:
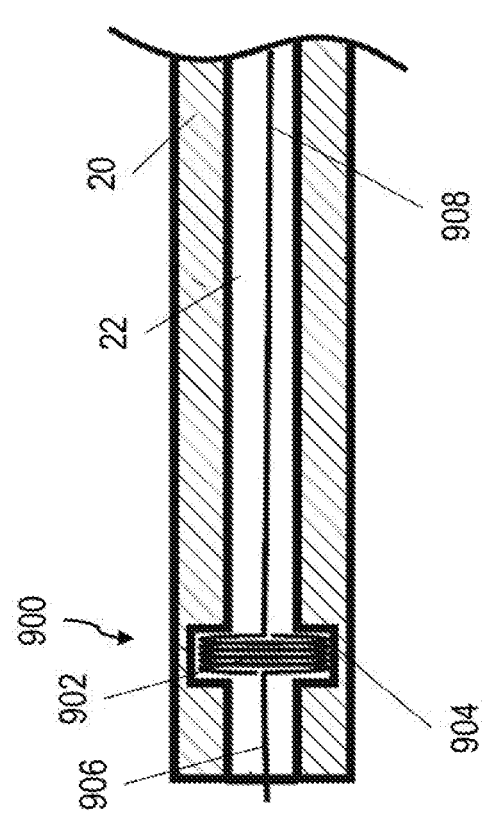

FIGS. 82A-82B illustrate another embodiment of the implant release control mechanism (900). As shown in FIG. 82A, the implant pusher shaft (20) has a recess within its inner lumen near its proximal end. The implant release control mechanism (900) is the proximal end portion (902) of the engagement wire (40) arranged in a first expanded orientation sized and shaped to frictionally engage the recess (904) within the implant pusher shaft lumen (22). In one embodiment, the first expanded orientation (902) of the engagement wire (40) is achieved by coiling, folding, twisting, wounding, and combinations thereof. As shown in FIG. 82A, during implant delivery and deployment, the expanded proximal portion (902) of the engagement wire (40) engages the recess (904) within the implant pusher shaft lumen (22). The remaining proximal portion (906) of the engagement wire (40) extends further proximally. The proximal end of the engagement wire (40) remains outside of the implant pusher shaft lumen (22). To actuate implant release, a clinician pulls the proximal end of the engagement wire (40), causes the expanded proximal portion (902) of the engagement wire (40) to unwind. As sufficient unwinding/contraction has occurred, the implant release control mechanism (900) disengages the implant pusher shaft (20).

Figure 83A:
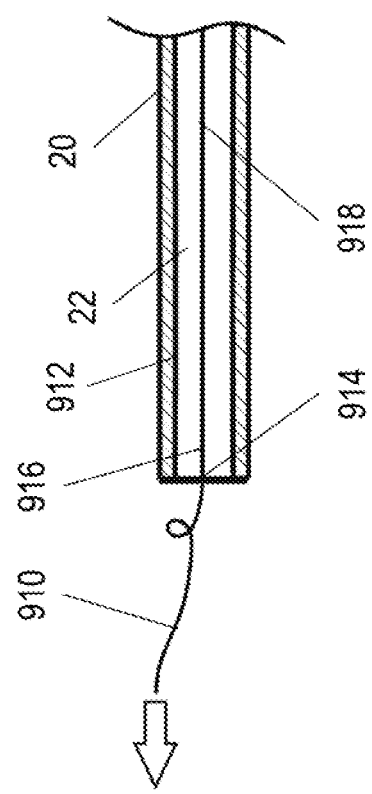
Figure 83B:
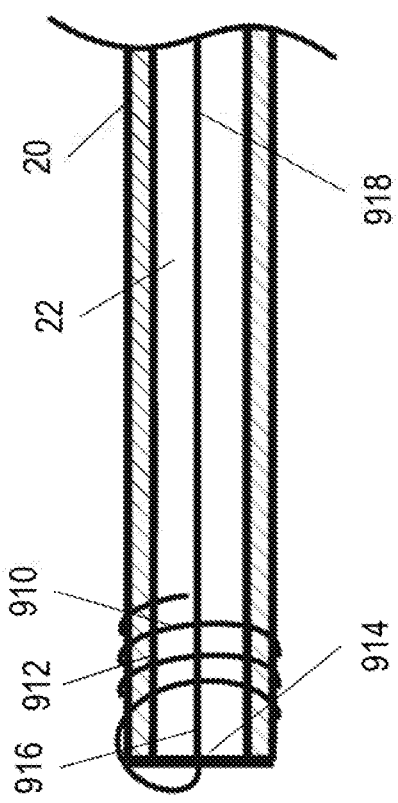

FIGS. 83A-83B illustrate a variation to the exemplary embodiment shown in FIGS. 82A-82B. Similar to what has shown in FIGS. 82A-82B, the implant release control mechanism (910) is the proximal end portion (916) of the engagement wire (918) arranged in an expanded coil (910). Unlike what has shown in FIGS. 82A-82B, when the implant release control mechanism (910) engages the implant pusher shaft (20), the proximal end portion (916) of the engagement wire (918) extends proximally outside of the proximal opening (914) of the implant pusher shaft lumen (22). The proximal end portion (916) of the engagement wire (918) then coils and frictionally engage with the outer surface of the proximal end portion (912) of the implant pusher shaft (20), such as by wrapping about the implant pusher shaft (20) as shown in FIG. 83A. To actuate implant release, a clinician pulls the proximal end of the engagement wire (918), causes the coiled proximal portion of the engagement wire (918) to unwind from the implant pusher shaft (20).

Figure 84A:
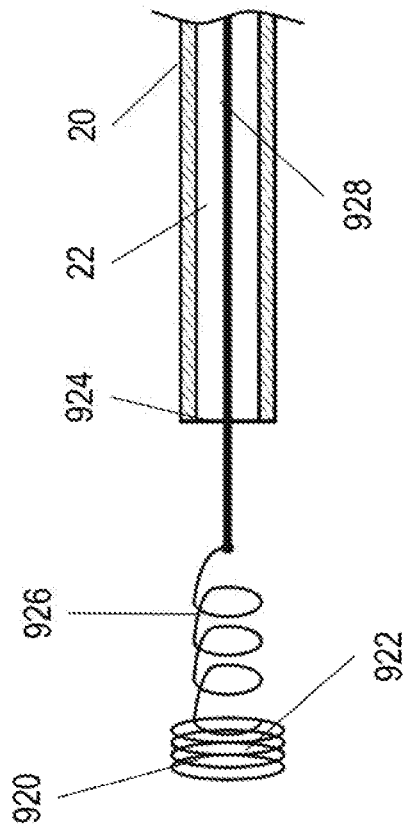
Figure 84B:
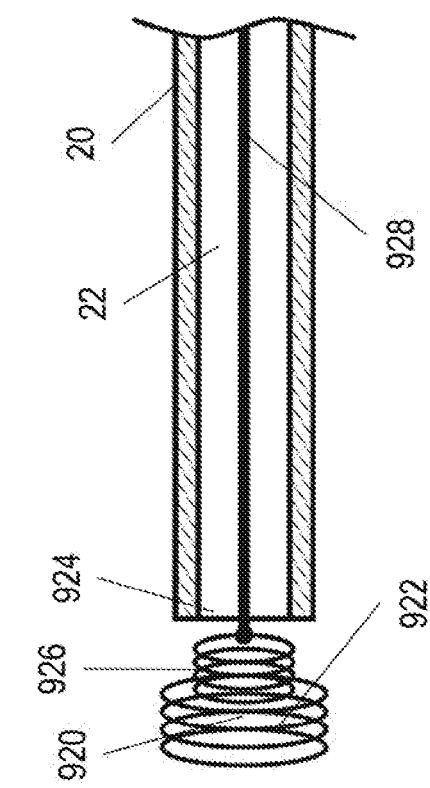

FIGS. 84A-84B illustrate another variation to the exemplary embodiment shown in FIGS. 82A-82B. Similar to what has shown in FIGS. 82A-82B, the implant release control mechanism (920) is the proximal end portion of the engagement wire (928) arranged in an expanded coil. Unlike what has described in FIGS. 82-83, during implant delivery and deployment, the expanded proximal end portion of the engagement wire (928) has a distal coil portion (926) which is sized and shaped frictionally engages a proximal opening (924) of the implant pusher shaft (20). The engagement wire (928) also has a proximal coil portion (922) which is sized to be larger than proximal opening (924) of the implant pusher shaft (20), to prevent any further distal movement of the engagement wire (928). To actuate implant release, the clinician pulls the proximal end of the engagement wire (928), causing all the proximal and distal coil (922, 926) of the implant release control mechanism (920) to contract/unwind, and eventually be released from the implant pusher shaft (20).

One skilled in the art should understand that in this embodiment, the coiled profile of the implant release control mechanism, shown in FIGS. 82-64, could function as a motion compensator such that without significant force being applied to coils, the engagement wire will not retract. In another embodiment, the proximal end of the engagement wire could also have a user-graspable element, such as a disk, ring, or bulbous element.

The various exemplary embodiments disclosed with reference to FIGS. 60-84 all involve the implant pusher shaft remains unchanged in its construct while the motion of the implant release control mechanism leads to the disengagement between the implant release control mechanism and the implant pusher shaft. FIGS. 85-90 illustrate another various exemplary embodiments where the disengagement between the implant release control mechanism and the implant pusher shaft also involves both a motion of the implant release control mechanism and a shape transformation of the proximal end portion of the implant pusher shaft.

Figure 85A:
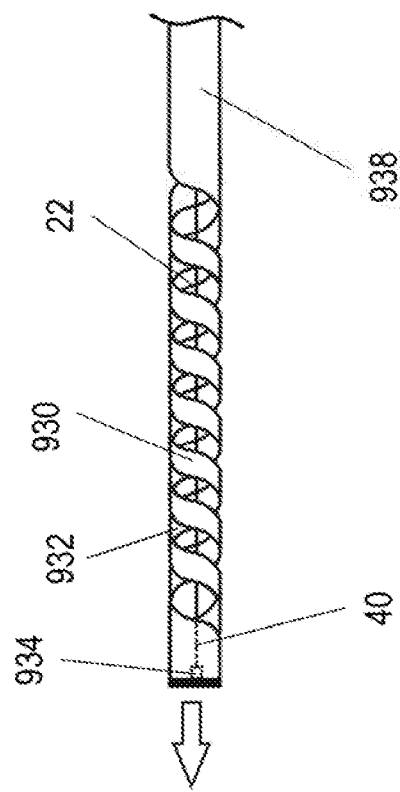
FIGS. 85-90 are perspective views of various exemplary implant release control mechanism where the disengagement between the implant release control mechanism and the implant pusher shaft involves a shape transformation of the proximal end portion of the implant pusher shaft in accordance with the present teachings.
Figure 85B:
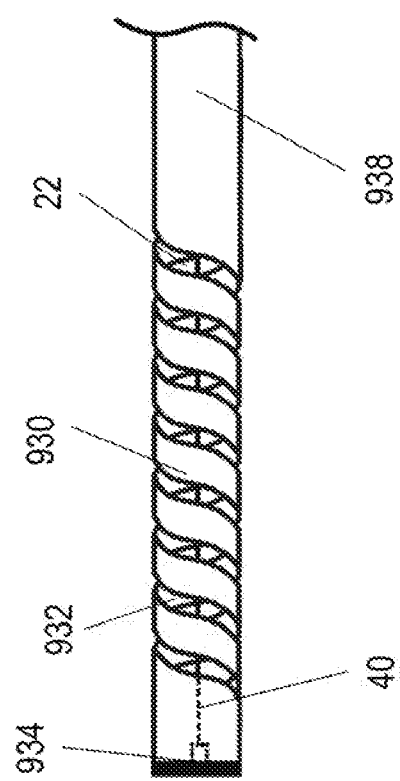

FIGS. 85A-85B illustrate an embodiment of the engagement/disengagement mechanism between the implant release control mechanism (930) and the implant pusher shaft (20). As shown in FIG. 85A, the implant pusher shaft (938) has an inner lumen (22) with a proximal cap (934). The engagement wire (40) extends inside the inner lumen (22) and fixedly attaches to the proximal cap (934) of the implant pusher shaft (20). The proximal end portion (930) of the implant pusher shaft (938) has one or more grooves (932) arranged in a spiral orientation. Such spiral groove (932) allows the proximal end portion (930) of the implant pusher shaft (938) to be stretched. In some embodiments, the grooves (932) is etched, ground, laser cut, or via other known method in the field incorporated into implant pusher shaft (938). During implant delivery and deployment, the proximal end portion (930) is at its shortest length. To retract the engagement wire (40), a clinician pulls the proximal end (24) of the implant pusher shaft (938), stretches the spiral groove portion (932). As the proximal end portion (930) of the implant pusher shaft (938) extends, the proximal end cap (934) pulls the engagement wire (40) proximally as shown in FIG. 85B.

Figure 86A:
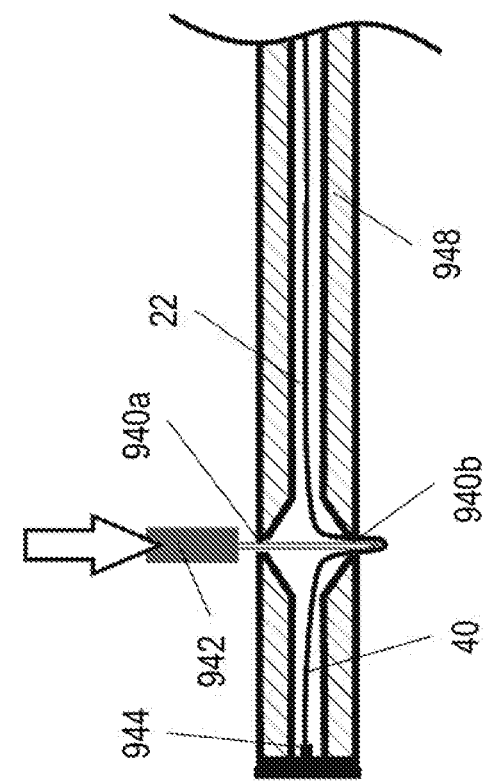
Figure 86B:
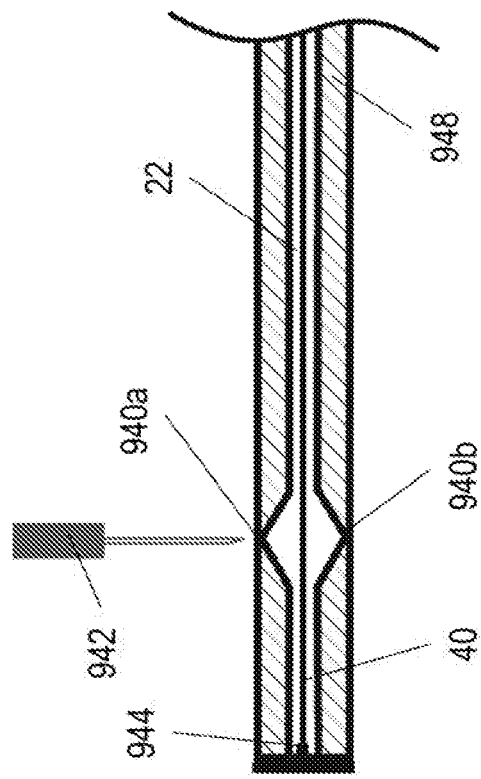

FIGS. 86A-86B illustrate another embodiment of the engagement/disengagement mechanism between the implant release control mechanism and the implant pusher shaft (20). As shown in FIG. 86A, the implant pusher shaft (948) has an inner lumen (22) with a proximal cap (944). The engagement wire (40) extends inside the inner lumen and fixedly attaches to the proximal cap (944) of the implant pusher shaft (948). The proximal end portion of the implant pusher shaft (948) has two aligned side holes (940a, 940b) configured to receive a projection (942). In one embodiment, the thickness of the inner luminal wall adjacent to the side holes (940a, 940b) are reduced to allow the projection (942) extending through the holes (940a, 940b) with minimum strength. During implant delivery and deployment, as shown in FIG. 86A, the engagement wire (40) extends inside the implant pusher shaft (948) and fixedly attaches to the proximal cap (944) of the implant pusher shaft (948). To retract the engagement wire (40), a clinician inserts the projection (942) into the first side hole (940a) from one side of the implant pusher shaft (948), engages the engagement wire (40) inside the implant pusher shaft lumen, and extends the projection (942) further through the second side hole (940b) on the other side of the implant pusher shaft (948). As shown in FIG. 86B, the projection (942) displaces the engagement wire (40) resulting in a proximal retraction of the engagement wire (40).

Figure 87A:
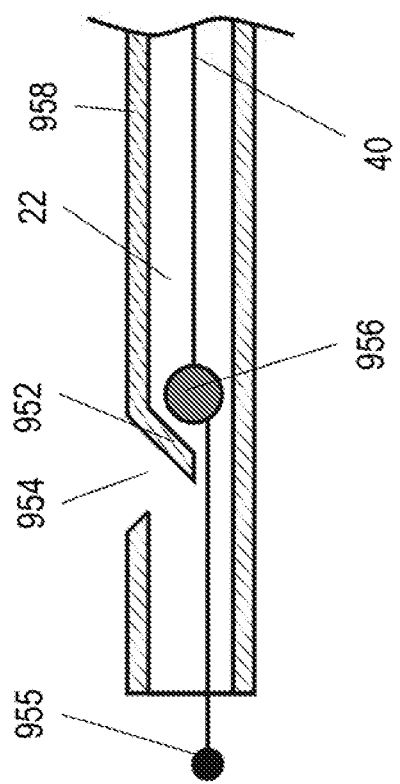
Figure 87B:
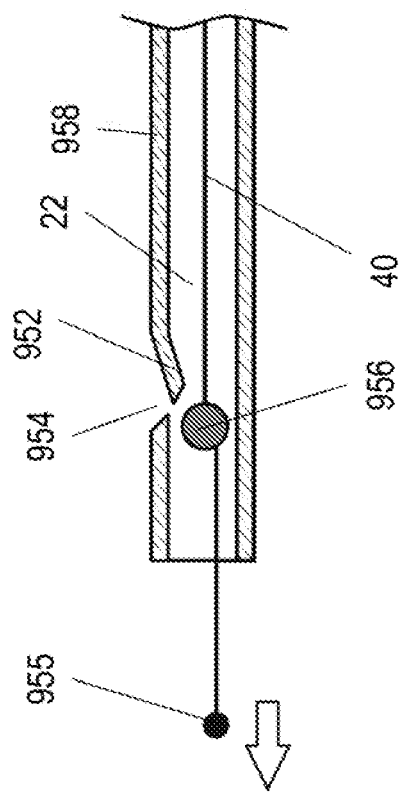

FIGS. 87A-87B illustrate another embodiment of the engagement/disengagement mechanism between the implant release control mechanism (950) and the implant pusher shaft (20). As shown in FIG. 87A, the implant pusher shaft (958) has a proximal end portion with a side opening (954). A bendable flap (952) is positioned at the distal end of the side opening (954) with a first bending angle and a second bending angle. The proximal end portion of the engagement wire (40) has an enlarged portion (956), such as in the shape of a ball, configured to be blocked by the bendable flap (952) at its first bending angle such as shown in FIG. 87A. At its second bending angle, the bending flap (952) opens the blockage and allows the enlarged portion (956) of the engagement wire (40) to freely move inside the implant pusher shaft lumen (22). A proximal end portion of the engagement wire (40) further extends proximally from the enlarged portion (956) of the engagement wire (40). As shown in FIG. 87A, during implant delivery and deployment, the enlarged ball (9526) on the engagement wire (40) is blocked by the bendable flap (952) at its first bending angle, and the proximal end portion of the engagement wire

(40) proximal to the ball (956) further extends proximally outside of the proximal opening of the implant pusher shaft (958). To retract the engagement wire (40), a clinician pulls the proximal end (955) of the engagement wire (40), causing the ball (956) to push against the bendable flap (952). With sufficient force, the bendable flap is pushed to its second bending angle and thereby opening up the implant pusher shaft lumen. The engagement wire (40) is then retracts proximally as shown in FIG. 87A.

Figure 88A:
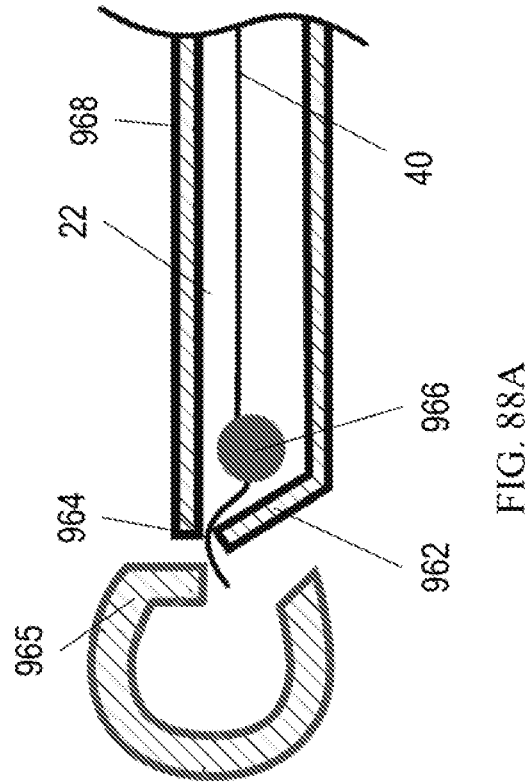
Figure 88B:
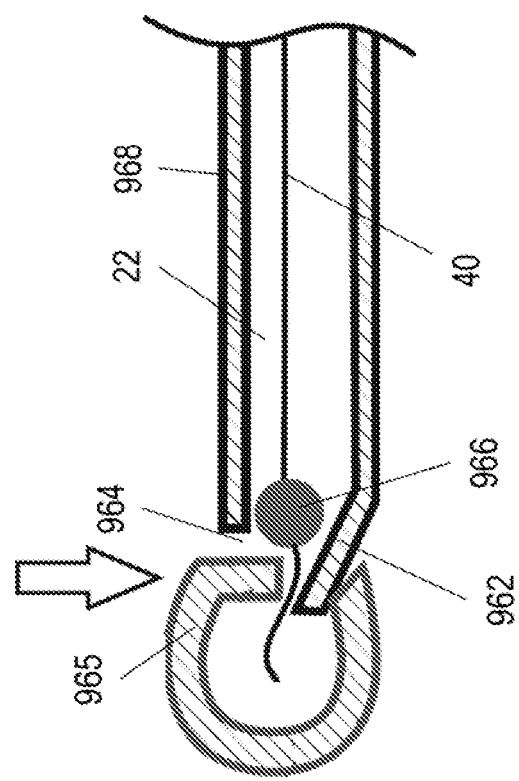

FIGS. 88A-88B illustrate a variation to the exemplary embodiment shown in FIGS. 87A-87B. Similar to what has shown in FIGS. 87A-87B, the implant pusher shaft (968) has a bendable flap (962) having a first bending angle and a second bending angle. Also similar to what has shown in FIGS. 87A-87B, the proximal end portion of the engagement wire (40) has an enlarged portion (966), such as in the shape of a ball, configured to be blocked by the bendable flap (962) at its first bending angle such as shown in FIG. 88A. At its second bending angle, the bending flap (962) opens the blockage and allows the enlarged portion (966) of the engagement wire (40) to freely extend outside of the implant pusher shaft lumen. Unlike what has shown in FIGS. 87A-87B, the bendable flap (962) is positioned at the proximal opening (964) of the implant pusher shaft (968). In addition, this exemplary embodiment further includes an additional tool (965) to allow a clinician to engage and manipulate the bendable flap (962). To retract the engagement wire (40), a clinician pulls the proximal end of the engagement wire (40) with sufficient force, and/or uses the tool (965) to force the bendable flap (962) to its second bending angle, and thereby allowing the engagement wire (40) to retract proximally as shown in FIG. 88A.

Figure 89A:
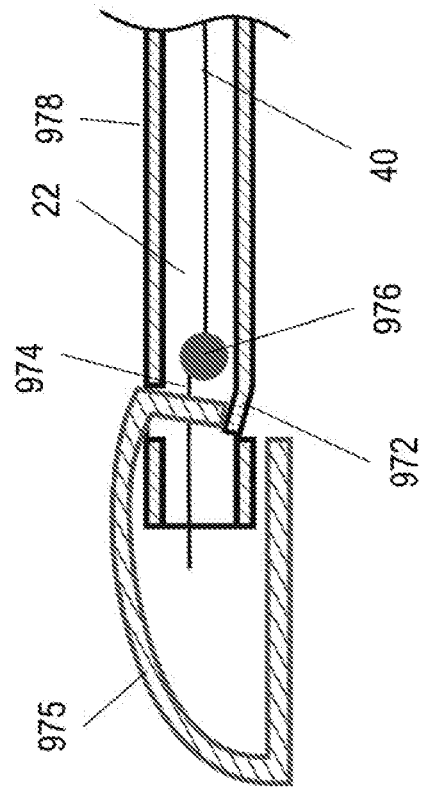
Figure 89B:
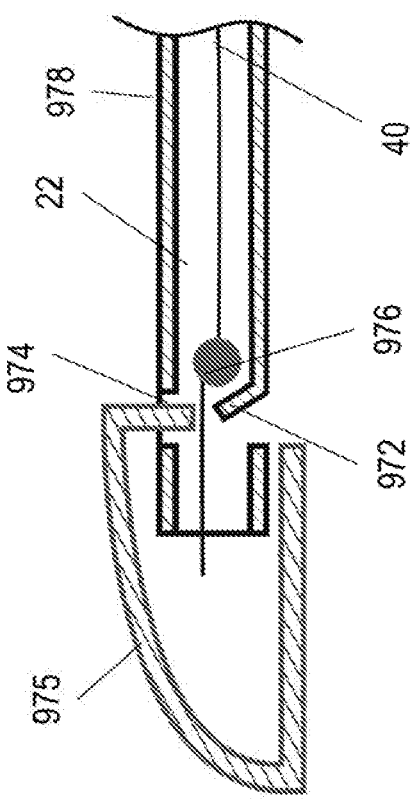

FIGS. 89A-89B illustrate a variation to the exemplary embodiments shown in FIGS. 87-88. Similar to what has shown in FIGS. 87-88, the implant pusher shaft (978) has a bendable flap (972) with a first bending angle and a second bending angle. Also similar to what has shown in FIGS. 87-88, the proximal end portion of the engagement wire (40) has an enlarged portion (976), such as in the shape of a ball, configured to be blocked by the bendable flap (972) at its first bending angle. At its second bending angle, the bending flap (972) opens the blockage and allows the enlarged portion (976) of the engagement wire (40) to freely extend outside of the implant pusher shaft lumen (22). Unlike what has shown in FIGS. 88A-88B, the proximal end portion of the implant pusher shaft (978) further has a side opening (974) across the longitudinal axis of the pusher shaft lumen (22) from the bendable flap (972). This exemplary embodiment also includes an additional tool (975) to allow a clinician to engage and manipulate the bendable flap (972). Unlike what has shown in FIGS. 88A-88B, the tool (975) enters a side opening (974) on the implant pusher shaft (978), into the implant pusher shaft lumen (22), then engages the bendable flap (972). Also similar to what has shown in FIGS. 88A-88B, to retract the engagement wire (40), a clinician pulls the proximal end of the engagement wire (40) with sufficient force, and/or uses the tool (975) to force the bendable flap (972) to its second bending angle, and thereby allowing the engagement wire (40) to retract proximally as shown in FIG. 89A.

Figure 90A:
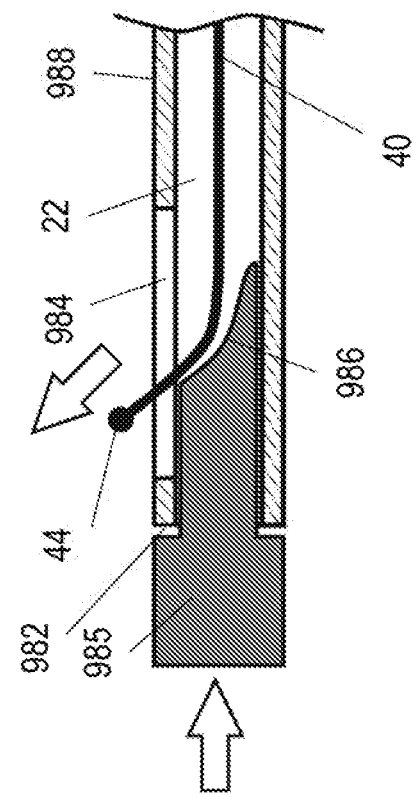
Figure 90B:
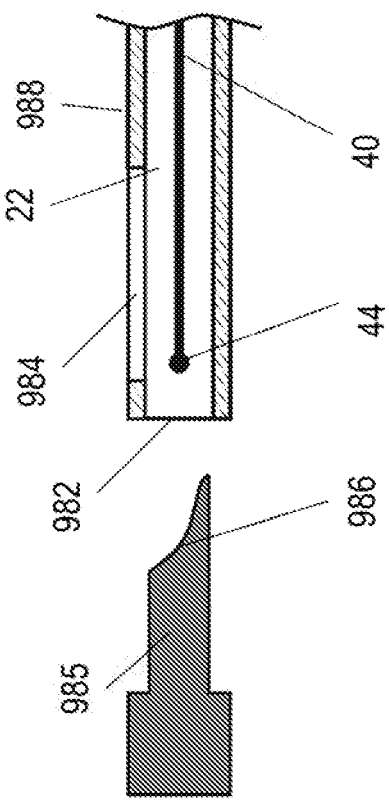

FIGS. 90A-90B illustrate another embodiment of the engagement/disengagement mechanism between the implant release control mechanism and the implant pusher shaft (978). As shown in FIG. 90A, the implant pusher shaft (988) has an inner lumen (22) with a proximal opening (982) and a side opening (984) at its proximal end portion. The engagement wire (40) extends inside the implant pusher shaft lumen (22). Acceding to one embodiment of the present teaching, during implant delivery and deployment, as the distal end of the engagement wire (40) engages the implant, the frictional force of the engagement is sufficient to keep the proximal end (44) of the engagement wire (40) relative stable in its positon as shown in FIG. 90A. This exemplary embodiment further includes a releasing tool configured to assist the movement of the proximal end (44) portion engagement wire (40). In one embodiment, the releasing tool (985) has a distal portion sized and shaped to extend into the proximal opening (982) of the implant pusher shaft lumen (22). The distal end of the releasing tool (985) further includes a sloped distal surface (986). As shown in FIG. 90B, the releasing tool (985) enters the proximal opening (982) of the implant pusher shaft lumen (22), the distal sloped surface (986) of the releasing tool (985) pushes the proximal end portion (44) of the engagement wire (40) toward the side opening (984) of the implant pusher shaft (978). A clinician can then grasp and pull proximal end (44) of the engagement wire (40).

Disclosure with reference to FIGS. 60-90 teach exemplary embodiment where the implant release control mechanism at the proximal end of the engagement wire releasable joins the proximal end the implant pusher shaft during implant delivery and deployment. The implant release control mechanism actuate implant release by detaches from the proximal end of the implant pusher shaft. FIGS. 91-110 illustrate another embodiment of the present teaching where the implant release control mechanism is constructed as part of the proximal end portion of the implant pusher shaft. According to some embodiments, the implant release control mechanism is configured to be breakable from the implant pusher shaft in order to actuate implant release. In one embodiment, the proximal end of the engagement wire fixedly joins the breakable proximal portion of the implant pusher shaft. During implant delivery and deployment, the breakable portion of the implant pusher shaft remains a unity to the implant pusher shaft. To actuate implant release, the breakable portion of the implant pusher shaft is broken away from the implant pusher shaft.

Figure 91A:
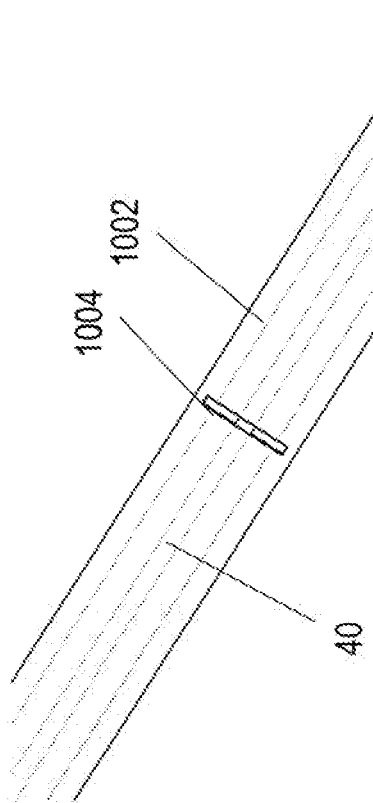
Figure 91B:
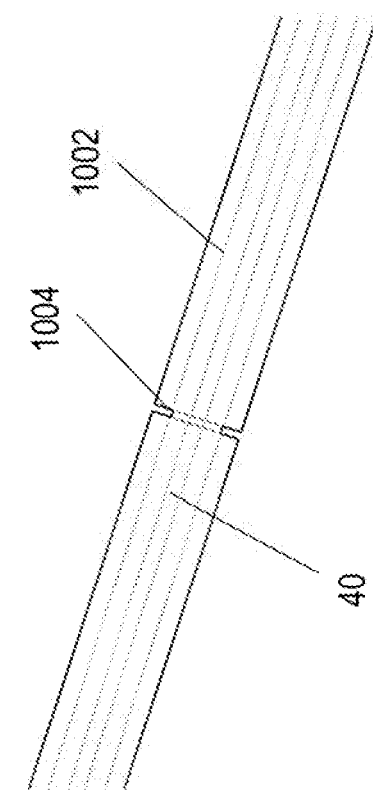

FIGS. 91A-91B illustrate an embodiment of the engagement/disengagement mechanism between the implant release control mechanism and the implant pusher shaft (1002). As shown in FIG. 91A, the implant pusher shaft (1002) has a breakable proximal portion (1000) separated from the remaining portion of the implant pusher shaft (1002) by a groove (1004). The proximal end of the engagement wire (40) fixedly attaches to the proximal portion (1000) of the implant pusher shaft (1002) proximal to the groove. In one embodiment, the groove (1004) is a full or partial circumferential recess achieved by removing material either via ground, laser-cut or other methods known in the field. During implant delivery and deployment, the breakable proximal portion (1000) remains a unity to the rest portion of the implant pusher shaft (1002). To retract the engagement wire (40) proximally, a clinician applies force to the breakable proximal portion (1000) of the implant pusher shaft (1002), causing it to snap or otherwise detach from the remaining portion of implant pusher shaft (1002). Subsequently retraction of the now broken away proximal portion (1000) of the implant pusher shaft (1002) results a corresponding retraction of the engagement wire (40).

Figure 92A:
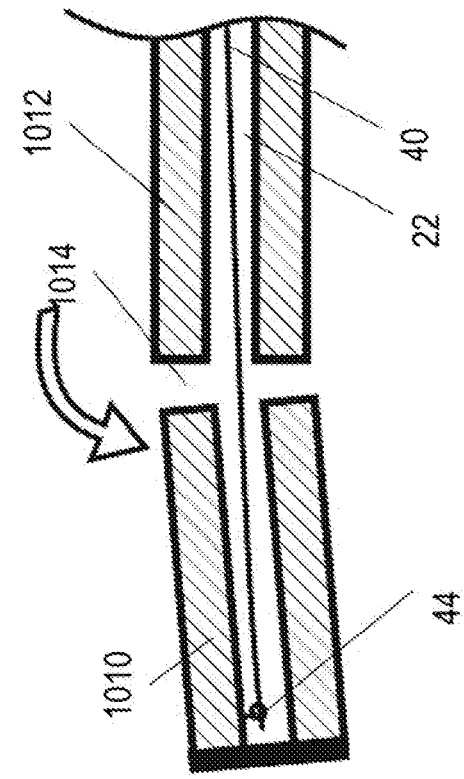
Figure 92B:
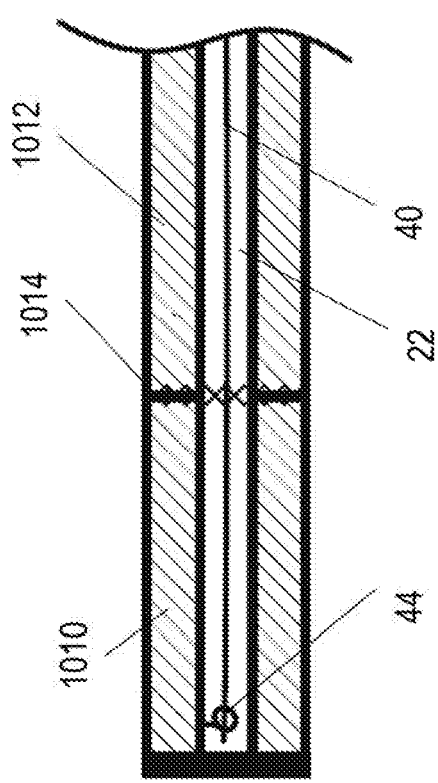

FIGS. 92A-92B illustrate a variation to the exemplary embodiment shown in FIGS. 91A-91B. Similar to what has shown in FIGS. 91A-91B, the implant pusher shaft (1012) also has a breakable proximal portion (1010) separated from the remaining portion of the implant pusher shaft (1012) by a weakened location (1014). Unlike what has shown in FIGS. 91A-91B, the proximal end (44) of the engagement wire (40) joins the breakable proximal portion (1010) by a lasso. Similar to what has been described above with reference to FIGS. 91A-91B, to retract the engagement wire (40) proximally, a clinician applies sufficient force to the breakable proximal portion (1010) of the implant pusher shaft (1012) first, followed by subsequently retraction of the now broken away proximal portion (1010) of the implant pusher shaft (1012).

In some embodiments, the weakened location could be constructed by two mating shafts, for example, two shafts with their adjacent ends joined by various thermal, chemical, or mechanical methods that provides sufficient attachment strength during delivery and deployment, while still remains breakable by a clinician. In some embodiments, the chemical attachment methods could be adhesive, solvent bonding; thermal attachment methods could be welding. In another embodiments, the weakened location could be constructed by removing material from a full or partial circumference of a portion of the implant pusher shaft (20), for example, by chemical or laser etching, perforating, partial slicing, routing, machining and/or other known methods.

FIGS. 93A-93B illustrate a variation to the exemplary embodiment shown in FIGS. 91A-91B. Similar to what has shown in FIGS. 91A-91B, the implant pusher shaft (1022) also has a breakable proximal portion (1020) separated from the remaining portion of the implant pusher shaft (1022) by a weakened location (1024). Unlike what has shown in FIGS. 91A-91B, the weakened location (1024) is achieved by removing material at a portion of the implant pusher shaft (1022). Similar to what has been described above with reference to FIGS. 91A-91B, to retract the engagement wire (40) proximally, a clinician applies sufficient force to the breakable proximal portion (1020) of the implant pusher shaft (1022) first, followed by subsequently retraction of the now broken away proximal portion (1020) of the implant pusher shaft (1022).

FIGS. 94A-94B illustrate an embodiment of the engagement/disengagement mechanism between the implant release control mechanism and the implant pusher shaft (1032). As shown in FIG. 94A, the proximal portion of the implant pusher shaft (1032) has an L-shaped profile. The implant release control mechanism (1030) also has an L-shaped distal end. Although it is described here as a separate portion, according to one embodiment, the implant release control mechanism (1030) and the implant pusher shaft (1032) are integrally connected together by a pin (1034). In one embodiment, the pin (1034) has a weakened location (1036) in the middle. Similar to what has been described above, to retract the engagement wire (40) proximally, a clinician applies sufficient force to break the pin at its weakened location (1036), followed by subsequently retraction of the now broken away proximal portion (1030) of the implant pusher shaft (1032).

Figure 95:
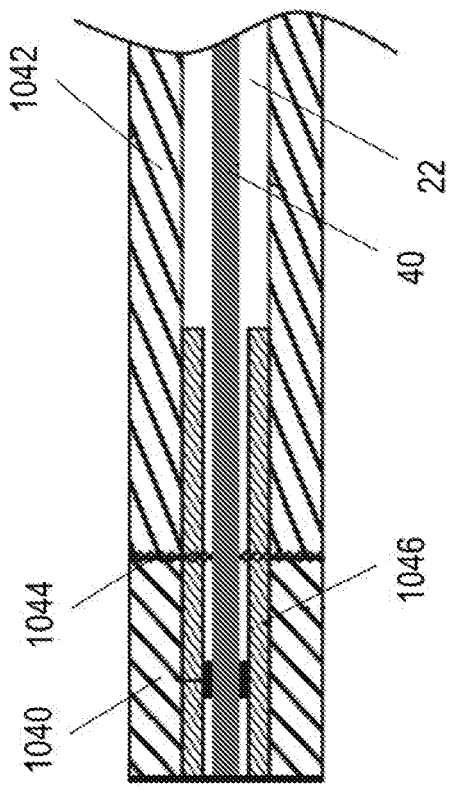

FIG. 95 illustrates another variation to the exemplary embodiment shown in FIGS. 91A-91B. Similar to what has shown in FIGS. 91A-91B, the implant pusher shaft (1042) also has a breakable proximal portion (1040) separated from the remaining portion of the implant pusher shaft (1042) by a weakened location (1044). Unlike what has shown in FIGS. 91A-91B, the proximal end (44) of the engagement wire (40) fixedly joins to an inner tube (1046). The inner tube (1046) fixed joins the proximal end of the breakable proximal portion (1040) of the implant pusher shaft (1042), slidably disposed within the implant pusher shaft lumen (22) extending distally beyond the weakened location (1044). As the breakable proximal portion (1040) breaks away from the rest of the implant pusher shaft (1042), the tube carrying the engagement wire (40) also retracts proximally.

FIGS. 91-95 illustrate various embodiments where disengagement between the breakable implant release control mechanism and the rest of the implant pusher shaft are done by a clinician manually applying sufficient force. FIGS. 96-103 illustrate various embodiments where disengagement between the breakable implant release control mechanism and the rest of the implant pusher shaft are done with the assistance of a tool. Among other things, FIGS. 96-103 all illustrate that the implant pusher shaft also has a breakable proximal portion separated from the remaining portion of the implant pusher shaft by a weakened location, and the proximal end of the engagement wire fixedly joins the breakable proximal portion of the implant pusher shaft. To release the implant, the clinician applies sufficient force to weakened location of the implant pusher shaft through the tool, causing circumferential fracture at the weakened location. Subsequently retraction of the now broken away proximal portion of the implant pusher shaft (20) results a corresponding retraction of the engagement wire.

Figure 96A:
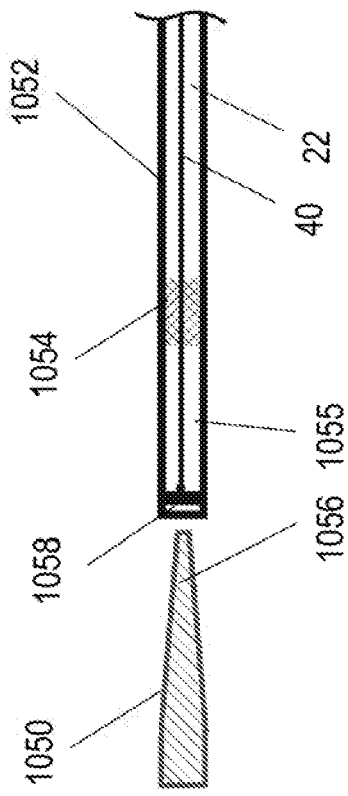
Figure 96C:
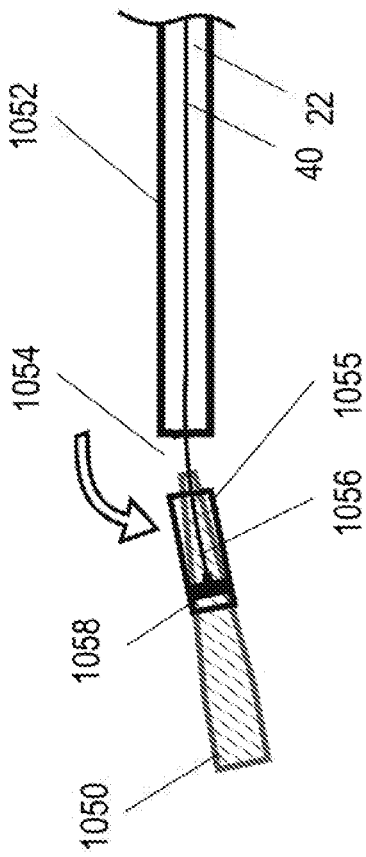
Figure 96B:
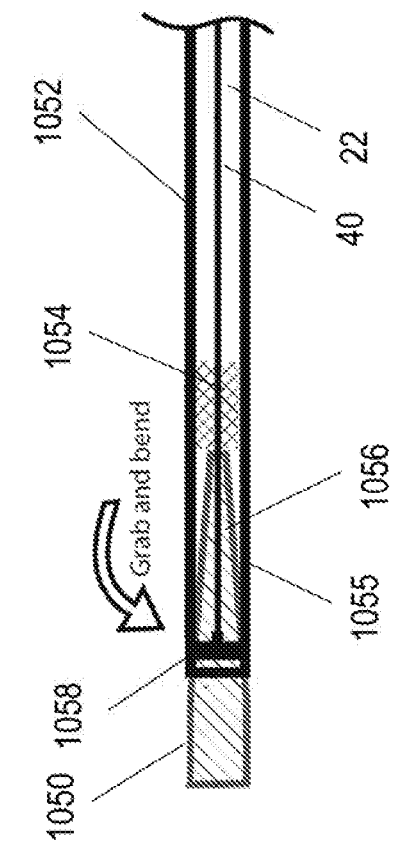

FIGS. 96A-96C illustrate an embodiment of the disengagement tool (1050) having a tapered distal end (1056) configured to extend from the proximal opening (1058) of the implant pusher shaft (1052) into its lumen (22). As the tool (1050) sufficiently advanced into implant pusher shaft (1052) as seen in FIG. 96B, a clinician applies sufficient force causing circumferential fracture at the weakened location (1054) as shown in FIG. 96C. Subsequently retraction of the now broken away proximal portion (1055) of the implant pusher shaft (1052) results a corresponding retraction of the engagement wire (40).

Figure 97A:
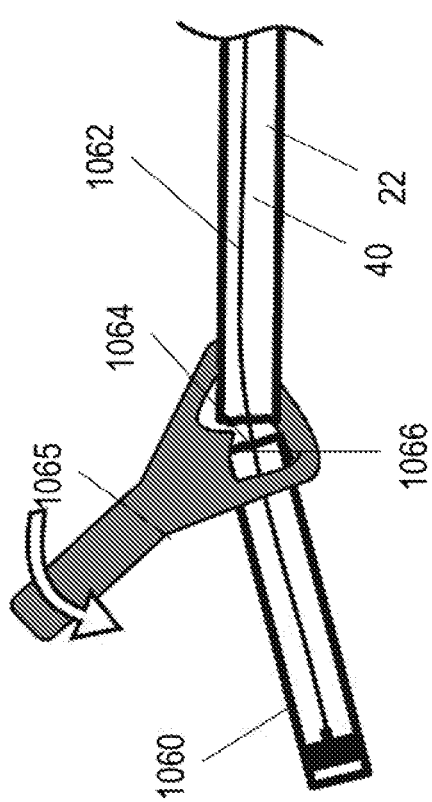
Figure 97B:
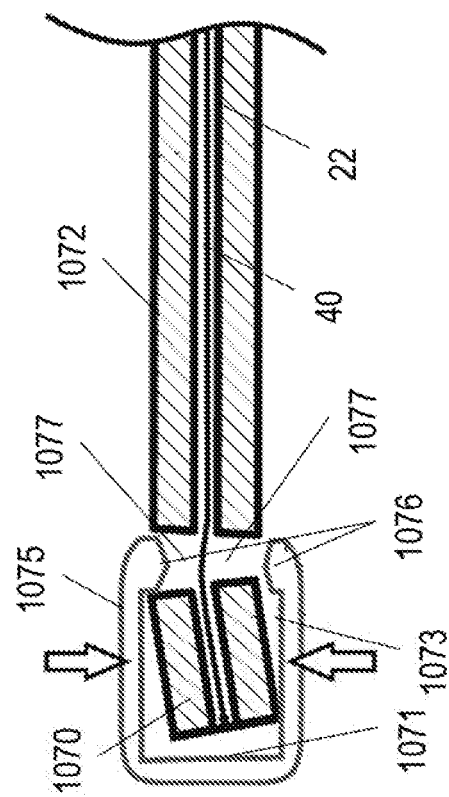

FIGS. 97A-97B illustrate another embodiment where a disengagement tool (1065) is used to actuate implant release. The disengagement tool (1065) in this exemplary embodiment has a body with an aperture sized and configured to slide over the implant pusher shaft (1062). A sharp point (1066) within the aperture of the tool (1065) body is configure to function as a force concentration point to break the breakable proximal portion (1060) from the remaining portion of the implant pusher shaft (1062). As the sharp point (1066) engages the weakened location (1064) of the implant pusher shaft (1062), a clinician applies sufficient force to the tool (1065), causing circumferential fracture at the weakened location (1064) as shown in FIG. 97B.

Figure 98A:
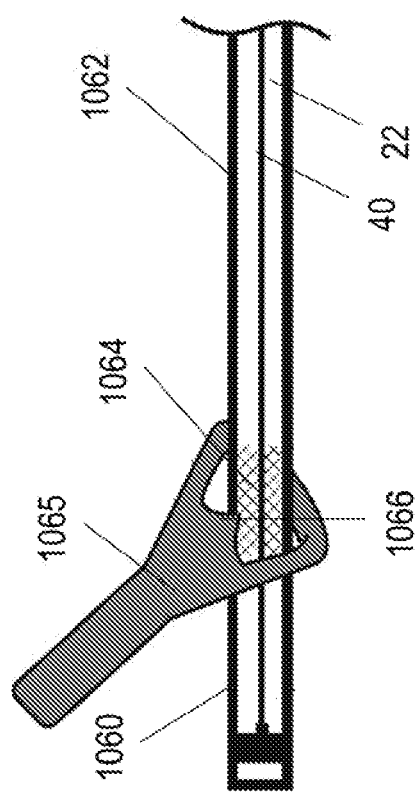
Figure 98B:
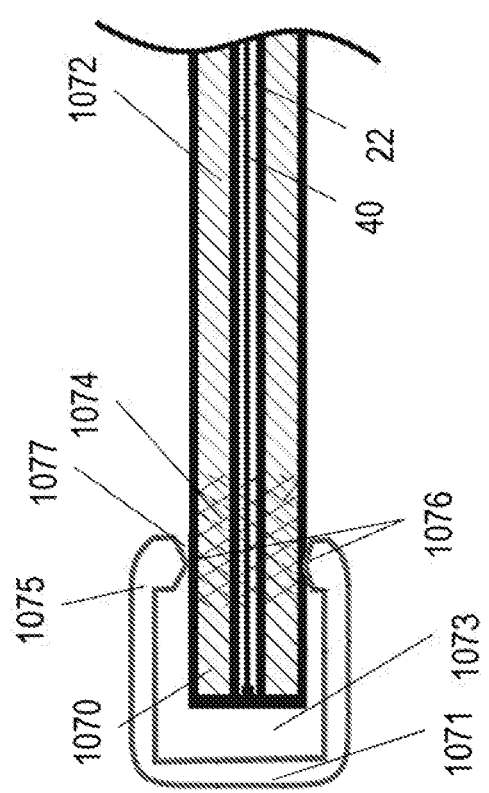

FIGS. 98A-98B illustrate another embodiment of the disengagement tool (1075). The tool (1075) has a cavity (1073), a proximal stop (107q) and a distal opening (1077). The cavity (1073) of the disengagement tool (1075) has an insertion distance configured to slidably receives the proximal end portion of the implant pusher shaft (1072). The disengagement tool (1075) includes one or more projections (1076) configured to frictionally engage the outer surface of the implant pusher shaft (1072), as shown in FIG. 98A. Force applied by a clinician to the tool (1075) causing circumferential fracture at the weakened location (1074) of the implant pusher shaft (1072) as shown in FIG. 98B.

Figure 99A:
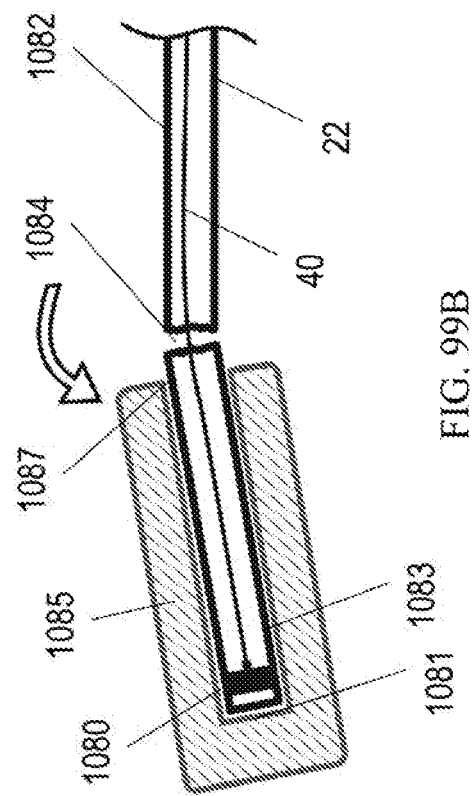
Figure 99B:
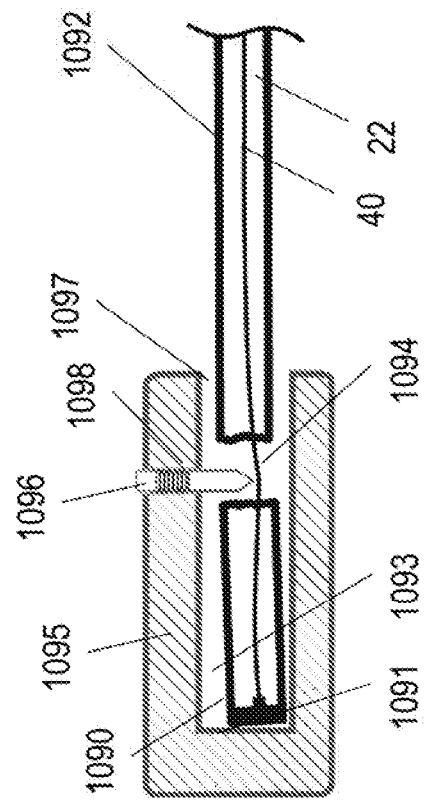

FIGS. 99A-99B illustrate another embodiment of the disengagement tool (1085) also having a cavity (1083), a proximal stop (1081) and a distal opening (1087), similar to what has been shown in FIGS. 98A-98B. When the tool (1075) engages the proximal end of the implant pusher shaft (1082), the proximal end portion (1080) of the implant pusher shaft (1082) sufficiently advances into tool (1085) to engage the proximal stop (1081) of the tool (1085). Force applied by a clinician to the tool (1085) causing circumferential fracture at the weakened location (1084) of the implant pusher shaft (20) as shown in FIG. 99B.

Figure 100A:
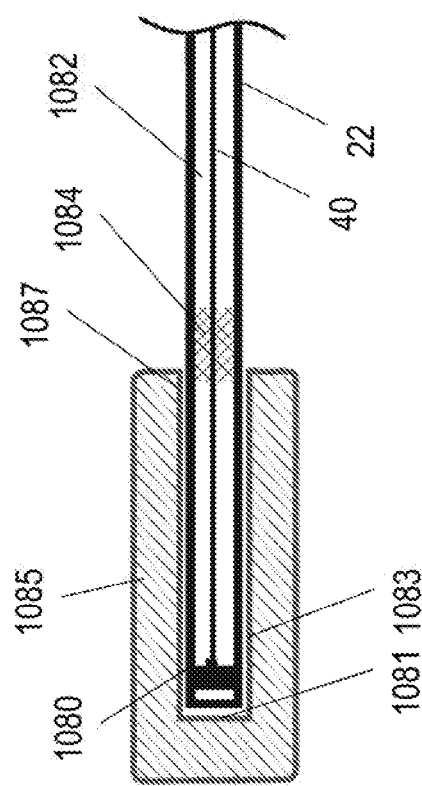
Figure 100B:
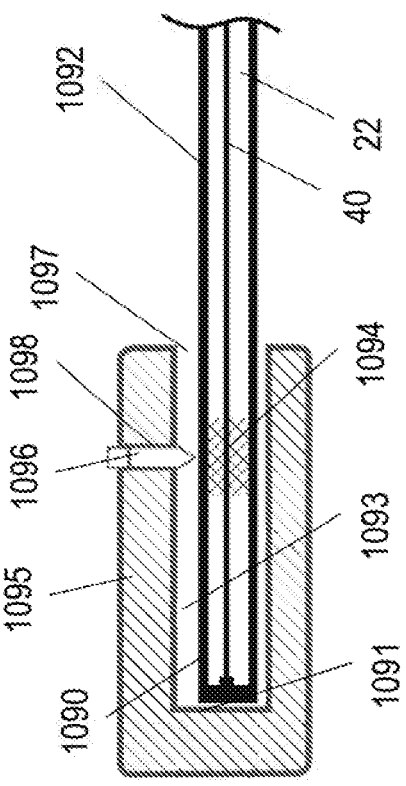

FIGS. 100A-100B illustrate another embodiment of the disengagement tool (1095) also having a cavity (1093), a proximal stop (1091), a distal opening (1097). The disengagement tool (1095) shown in these figures also has a side opening (1098), and a spring loaded actuator (1096) sized and shaped to fit through the side opening (1098). When the tool (1095) engages the proximal end of the implant pusher shaft (1092), the proximal end portion (1090) of the implant pusher shaft (1092) sufficiently advances into disengagement tool (1095) to engage the proximal stop (1091) of the tool (1095), and the spring loaded actuator (1096) is positioned against the weakened location (1094) of the implant pusher shaft (1092). Force applied by a clinician to the actuator causes circumferential fracture at the weakened location (1094) of the implant pusher shaft (1092) as shown in FIG. 100B.

Figure 101A:
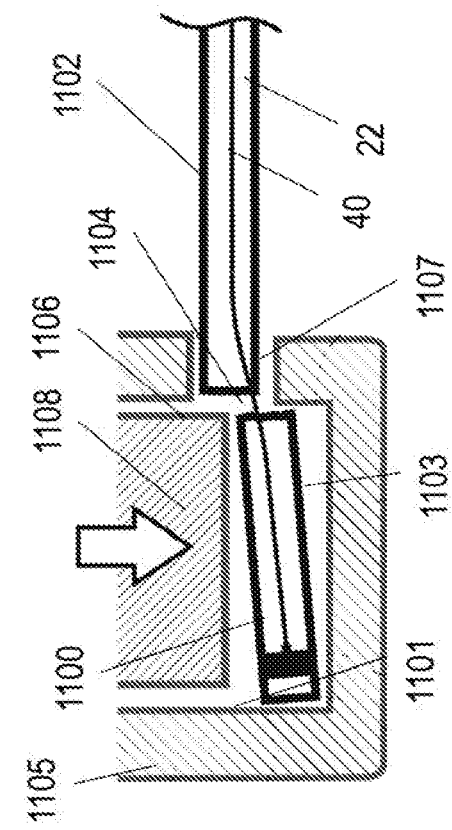
Figure 101B:
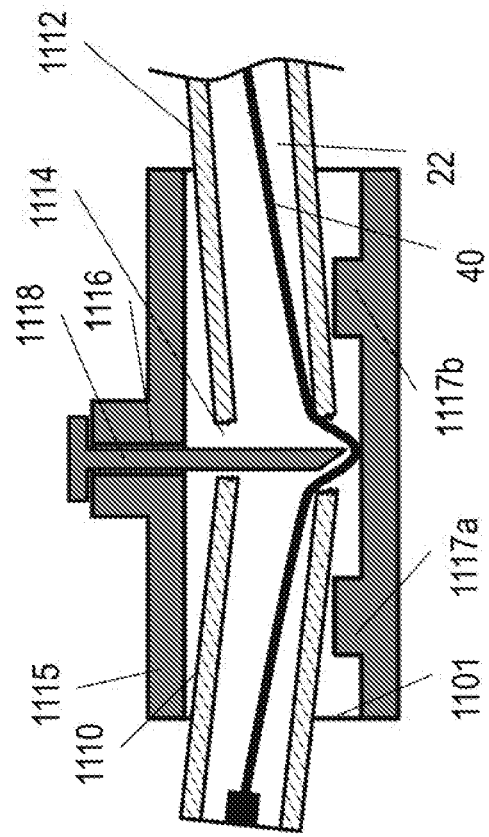

FIGS. 101A-101B illustrate a variation to the embodiment of the disengagement tool (1105) shown in FIGS. 100A-100B. Similar to what has been shown in FIGS. 100A-100B, the tool (1105) also has a cavity (1103), a proximal stop (1101), a distal opening (1107), and a side opening (1106) fitted with an actuator (1108). When the tool (1105) engages the proximal end of the implant pusher shaft (1102), the cavity (1103) slidably receives the proximal end portion (1100) implant pusher shaft (1102). Unlike what has been shown in FIGS. 100A-100B, the actuator (1108) is positioned against the breakable proximal portion (1100) of the implant pusher shaft (1102), proximal to the weakened location (1104) of the implant pusher shaft (20). Force applied by a clinician to the actuator (1108) causing circumferential fracture at the weakened location (1104) of the implant pusher shaft (20) as shown in FIG. 101B.

Figure 102A:
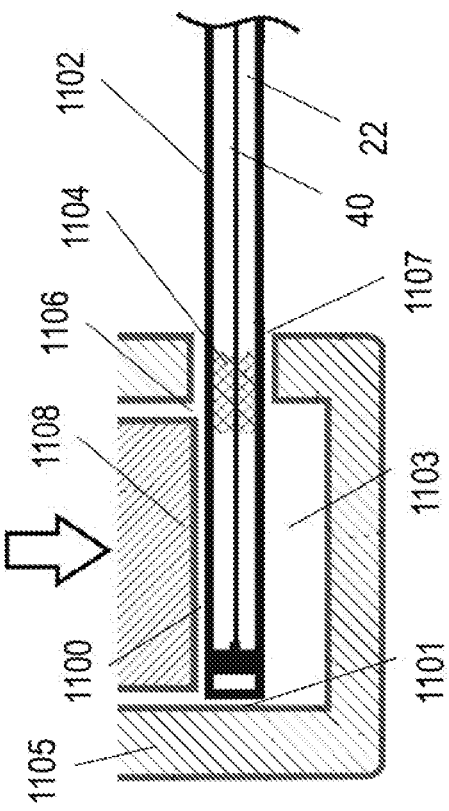
Figure 102B:
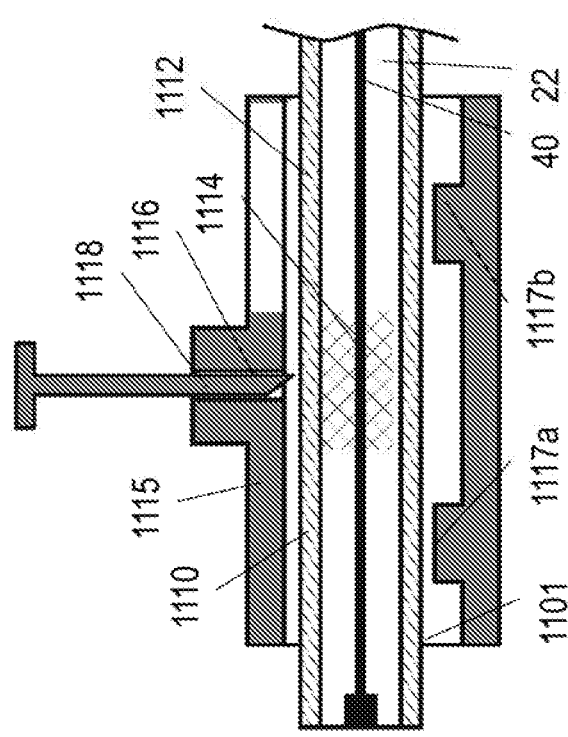

FIGS. 102A-102B illustrate a variation to the embodiment of the disengagement tool (1115) shown in FIGS. 100A-100B. Similar to what has been shown in FIGS. 100A-100B, the tool (1115) has a cavity (1113), a distal opening (1117), a side opening (1116), and an actuator (1118) size and shaped to fit into the side opening (1116). Unlike what has been shown in FIGS. 100A-100B, the disengagement tool (1115) has a proximal opening (111) instead of a proximal stop. In one embodiment, the cavity (1113) of the disengagement tool (1115) opposite to the side opening (1116) includes two projections (1117a, 1117b). These (1117a, 1117b) are configured to provide pivot points resisting movement of implant pusher shaft (1112). When the disengagement tool (1115) engages the proximal end portion (1110) of the implant pusher shaft (1112), the actuator (1118) is positioned against the weakened location (1114) of the implant pusher shaft (1112), and the weakened location (1114) of the implant pusher shaft (1112) positioned is in between the two projections (1117a, 1117b). Force applied by a clinician to the actuator causes circumferential fracture at the weakened location (1114) of the implant pusher shaft (1112) as shown in FIG. 102B.

FIGS. 103A-103B illustrate another embodiment of the disengagement tool (1125) also having a cavity (1123), a proximal stop (1121) and a distal opening (1127). The tool (1125) further includes an actuator (1128), such as a ball as shown in FIG. 103A. In one embodiment, the disengagement tool (1125) has an enlarged portion (1126) configured to receive the ball (1128) shaped actuator. One skilled in the art should understand that, with other shaped actuator (1128), the disengagement tool (1125) may or may not have an enlarged portion. Similar to what has been described with reference to FIGS. 100A-100B, when the proximal portion (1120) of the implant pusher shaft (20) sufficiently advances into the disengagement tool (1125) to engage the proximal stop (1121) of the tool (1125), and the actuator (1128) is positioned against the weakened location (1124) of the implant pusher shaft (1122). Force applied by a clinician to the actuator causes circumferential fracture at the weakened location (1124) of the implant pusher shaft (1122) as shown in FIG. 103B.

FIGS. 104A-104B illustrate another embodiment of the disengagement tool (1135) also having a cavity, a proximal opening and a distal opening. In additional, the tool (1135) further has two magnets (1136a, 1136b). The two magnets (1136a, 1136b) interacts with each other thereby joining a proximal portion (1138) and a distal portion (1139) of the disengagement tool (1135). Similar to what has been described with reference to FIGS. 100A-100B, when the proximal portion (1130) of the implant pusher shaft (20) sufficiently advances into disengagement tool (1135) to engage the proximal stop of the tool (1135), the two magnets (1136a, 1136b) are positioned against the weakened location (1134) of the implant pusher shaft (1130). Force applied by a clinician to break apart two magnets (1136a, 1136b) causes a circumferential fracture at the weakened location (1134) of the implant pusher shaft (20) as shown in FIG. 104B.

FIGS. 105A-105B illustrate another embodiment of the disengagement tool (1145) also having a cavity (1143), a proximal stop (1141) and a distal opening (1147). In addition, the tool (1145) further has two actuators (1146a, 1146b). In one embodiment, the two actuators (1146a, 1146b) are configured to be positioned across the longitudinal axis of the implant pusher shaft lumen (22), while not directly opposite to each other. When the proximal portion (1140) of the implant pusher shaft (20) sufficiently advances into the disengagement tool (1145) to engage the proximal stop (1141) of the tool (1145), and the weakened location (1144) of the implant pusher shaft (1142) is positioned in between the two actuators (1146a, 1146b). Force applied by a clinician to both actuators (1146a, 1146b) causes circumferential fracture at the weakened location (1144) of the implant pusher shaft (1142) as shown in FIG. 105B. In some embodiments, actuators has threads that mate with corresponding threads of the disengagement tool (1145). To release the implant, a clinician rotates both actuators (1146a, 1146b), such that the actuators (1146a, 1146b) advances radially inward. As both actuators (1146a, 1146b) engage the implant pusher shaft (1142), a torsional force is then applied to implant pusher shaft (1152) causing implant pusher shaft (1142) to circumferential fracture at its weakened location (1154).

FIGS. 106A-106B illustrate another embodiment of the disengagement tool (1155) also having a cavity (1153), a proximal stop (1151) and a distal opening (1157). As shown in the FIG. 106A, the disengagement tool (1155) has one or more mechanical hinges (1159) configured to interact with the implant pusher shaft (1152). In some embodiments, the hinges (1159) is made of flexible arms configured to bend. In addition, according to some embodiments, the disengagement tool (1155) also includes an actuator (1158) configured to be used by a clinician to stabilize the implant pusher shaft (1152) during implant release. In one embodiment, the actuator (1158) has a first position in relation to the disengagement tool (1155) during implant delivery and deployment. In another embodiment, the actuator (1158) has a second position in relation to the disengagement tool (1155) during implant releasement. For example, the actuator (1158) has threads that mate with corresponding threads of disengagement tool (1155), such that rotation of actuator (1158) advances actuator (1158) to engage and stabilize implant pusher shaft (1152). In one embodiment, when the proximal portion (1150) of the implant pusher shaft (1152) sufficiently advances into disengagement tool (1155) to engage the proximal stop (1151) of the tool (1155), the hinges is positioned about the weakened location (1154) of the implant pusher shaft (1152). Force applied by a clinician to proximal portion (1150) of the implant pusher shaft (1152) results in the rotation about the hinges (1159), and causes the implant pusher shaft (1152) to circumferentially fracture at its weakened location (1154) as shown in FIG. 106B.

FIGS. 107A-107B illustrate a variation to the embodiment of the disengagement tool (1165) described with reference to FIGS. 106A-106B. Similar to what has shown in FIGS. 106A-106B, the disengagement tool (1165) has a cavity (1163), a proximal end (1161) and a distal opening (1167). The disengagement tool (1165) also has a distal portion (1168) and a proximal portion (1169) joining by a breakable portion (1166). In one embodiment, when the proximal portion (1160) of the implant pusher shaft (1162) sufficiently advances into disengagement tool (1165) to engage the proximal stop (1161) of the tool (1165), the weakened location (1164) is positioned against the breakable portion (1166) of the disengagement tool (1165). Force applied by a clinician to proximal portion (1160) of the implant pusher shaft (1162) results in the disengagement tool (1165) breaks at its breakable portion (1166), and causes the implant pusher shaft (1162) to circumferentially fracture at its weakened location (1164) as shown in FIG. 107B.

FIGS. 108A-108B illustrate another embodiment of the disengagement tool (1175) also having a cavity (1173), a proximal stop (1171) and a distal opening (1177). As shown in the FIG. 108A, the disengagement tool (1175) has a sharpened projection (1176) at one side of its inner luminal wall, and a rolling member (1179) along the opposite wall from the sharpened projection (1176). In some embodiment, the sharpened projection (1176) is configured to concentrate the force applied by the clinician to the weakened location (1174) of the implant pusher shaft (1172). In another embodiment, the rolling member (1179) has a wheel configured to travel along a track (1178) via an axle such as a recess on the outer surface of the implant pusher shaft (1172). In one embodiment, when the proximal portion (1170) of the implant pusher shaft (1172) sufficiently advances into disengagement tool (1175) to engage the proximal stop (1171) of the tool (1175), the sharpened projection (1176) is positioned about the weakened location (1174) of the implant pusher shaft (1172). Force applied by a clinician to the roller (1179) results in roller traveling proximally and frictionally engaging the implant pusher shaft (1172). This in turn causes the implant pusher shaft (1172) to circumferentially fracture at its weakened location (1174) as shown in FIG. 108B.

FIGS. 109A-109B illustrate another embodiment of the disengagement tool (1185) having a cavity (1183) configured in a curvilinear geometry. The cavity (1183) has an open end (1187) for the proximal portion (1180) of the pusher shaft (1182) to extend in and a closed end (1181). In one embodiment, the disengagement tool (1185) has a curve with a relatively small radius, approximately between 0.125" and 1". Cavity (1183) is configured to slidably receive the proximal portion (1180) of the implant pusher shaft (1182) via its open end (1187). In one embodiment, the proximal portion (1180) of the implant pusher shaft (1182) advances into disengagement tool (1185). The flexibility of the proximal portion (1180) of the implant pusher shaft (1182) is configured to accommodate the curvature of the cavity (1183). This flexibility can either be achieved by material choice or by physical construction. In one embodiment, when the proximal portion (1180) of the implant pusher shaft (1182) s reaches the closed end (1181) of the cavity, the weakened location (1184) of the implant pusher shaft (1182) is positioned adjacent to the most curved position of the cavity (1183), such as the apex of the "U" as shown in FIG. 109B. This forced bending of the implant pusher shaft (1182) causes implant pusher shaft (20) to circumferentially fracture at its weakened location (1184) as shown in FIG. 109B.

FIGS. 110A-110B illustrate another embodiment of the disengagement tool (1195) also having a cavity (1193), a proximal stop (1191) and a distal opening (1197). As shown in the FIG. 110A, the disengagement tool (1195) has two tubes, a proximal tube (1198) and a distal tube (1199). The two tubes (1198, 1199) are configured to abut each other at their diagonally cut ends (1196a, 1196b). In one embodiment, disengagement tool (1195) is made of flexible materials, such as silicone, urethane, latex, and combinations of these. This allows the tool (1195) to twist, bend, or otherwise deformed during implant release. Similar to what has been described above, in one embodiment, when the tool (1195) engages the proximal portion (1190) of the implant pusher shaft (1192), the p proximal portion (1190) of the implant pusher shaft (1192) sufficiently advances into disengagement tool (1195) disengagement tool (1195) to engage the proximal stop (1191) of the tool (1195). Force applied by a clinician to the tool, as shown by the arrow in FIG. 110B, causes disengagement tool (1195) to deform such that its proximal tube (1198)'s central axis moves away from the central axis of distal tube due to the interaction of their diagonally cut end (1196a, 1196b). Such displacement of tubes (1198, 1199) causes implant pusher shaft (1192) to circumferentially fracture at its weakened location (1194).

FIGS. 111-118 illustrate various embodiments where the implant release control mechanism has an additional element used to cover the weakened location of the implant pusher shaft so that a clinician is not exposed with fracture. In one embodiment, such element is configured to position over the weakened location of the implant pusher shaft. Such element has a flexible nature that allows a clinician to bend and/or fracture the implant pusher shaft through this element without being exposed to the fracture.

Figure 111A:
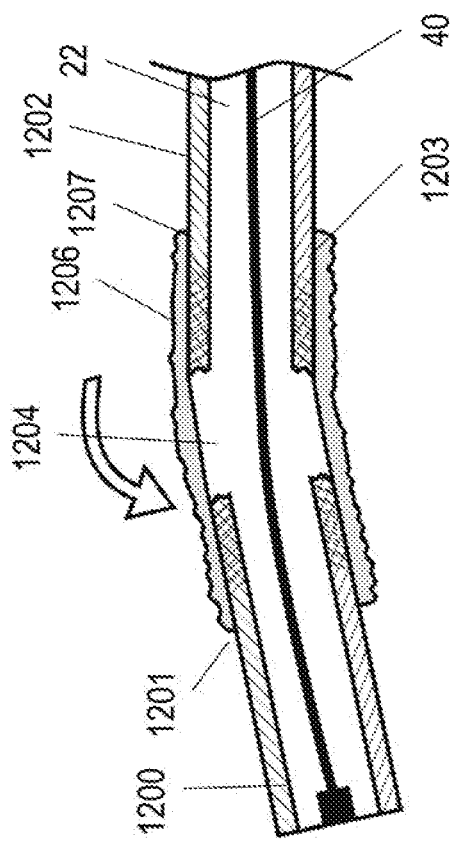
FIGS. 111-118 are perspective views of various exemplary embodiments where the engagement and disengagement between the implant release control mechanism and the implant pusher shaft is covered in accordance with the present teachings.
Figure 111B:
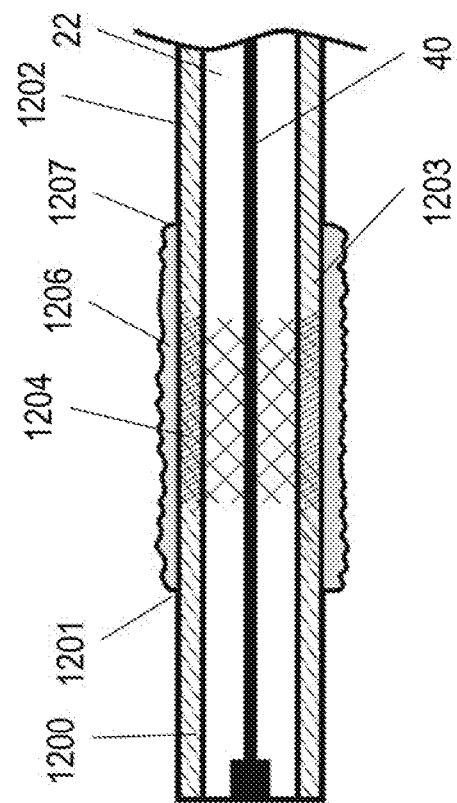

FIGS. 111A-111B illustrate another embodiment of the disengagement tool (1206) in the configuration of band with a center lumen (1203), a proximal opening (1201) and a distal opening (1207). As shown in the FIG. 111A, the band (1206) has a flexible nature and is configured to cover the weakened location of the implant pusher shaft (1202). In one embodiment, the band (1206) is made of one or more flexible materials, such as silicone, low durometer PEBAX, urethane, latex, and/or others known in the field. Band (1206) is configured to elastically and/or plastically expand or otherwise deform in response to an external force. In one embodiment, when the tool (1206) engages the proximal portion (1200) of the implant pusher shaft (1202), the band (1206) is positioned over the weakened location (1204) of the implant pusher shaft (1202). Force applied by a clinician to band causes implant pusher shaft (1202) to circumferentially fracture at its weakened location (1204). This band allows implant pusher shaft (1202) to break without exposing the clinician to any fracture.

Figure 112A:
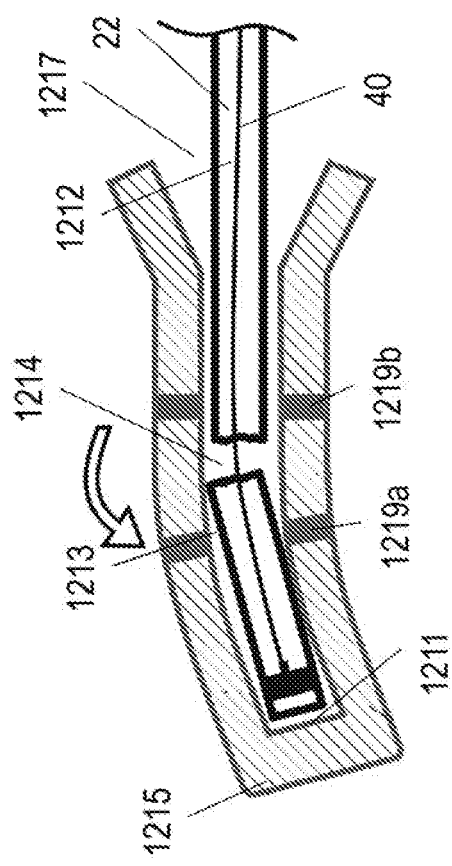
Figure 112B:
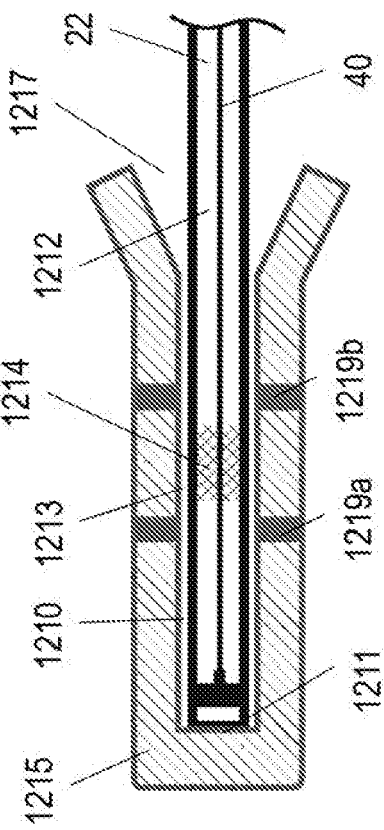

FIGS. 112A-112B illustrate another embodiment of the disengagement tool (1215) also having a cavity (1213), a proximal stop (1211) and a distal opening (1217). As shown in the FIG. 112A, the disengagement tool (1215) has a funnel-shaped distal opening (1217). In one embodiment, the disengagement tool (1215) could also have one or more visible markers (1219a, 1219b), such as two markers (1219a, 1219b) shown in FIG. 112A. In one embodiment, when the proximal portion (1212) of the implant pusher shaft (1212) sufficiently advances into disengagement tool (1215) to engage the proximal stop (1211) of the disengagement tool (1215), the weakened location (1214) of the implant pusher shaft (1212) is positioned in between the two visible markers (1219a, 1219b). Force applied by a clinician to the disengagement tool (1215) causes implant pusher shaft (20) to circumferentially fracture at its weakened location (1214b). This disengagement tool (1215) allows implant pusher shaft (20) to break without exposing the clinician to any fracture.

Figure 113A:
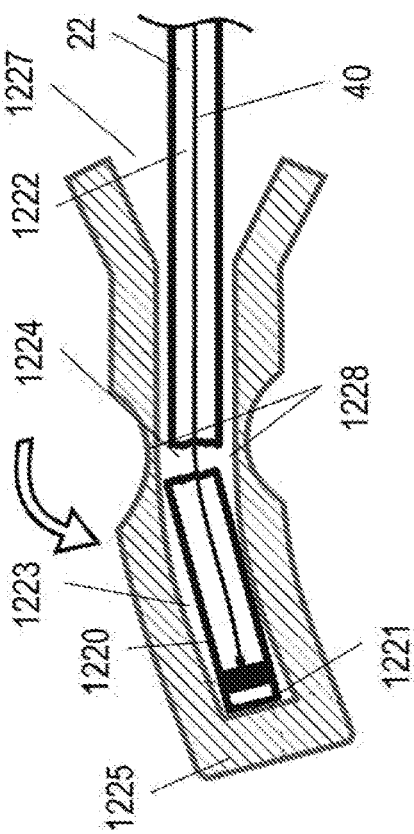
Figure 113B:
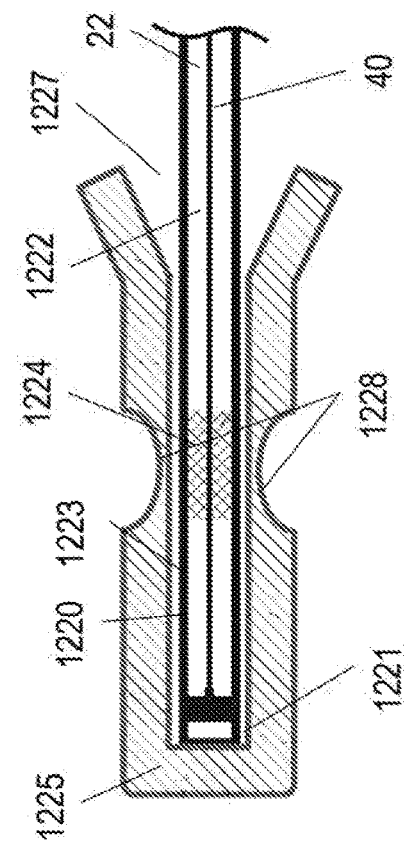

FIGS. 113A-113B illustrate a variation to the embodiment of the disengagement tool (1225) described with reference to FIGS. 112A-112B. Similar to what has shown in FIGS. 112A-112B, the disengagement tool (1225) has a cavity (1223), a proximal end (1221) and a distal opening (1227). Unlike embodiments described above, the disengagement tool (1225) has one or more depression (1228), such as the depressions shown in FIG. 113A. In one embodiment, when the proximal portion (1220) of the implant pusher shaft (1222) sufficiently advances into disengagement tool (1225) to engage the proximal stop (1221) of the tool (1225), the weakened location (1224) of the implant pusher shaft (20) is positioned against the depressions (1228) on the disengagement tool (1225). Force applied by a clinician to disengagement tool (1225) causes implant pusher shaft (1222) to circumferentially fracture at its weakened location (1224). This disengagement tool (1225) allows implant pusher shaft (20) to break without exposing the clinician to any fracture.

Figure 114A:
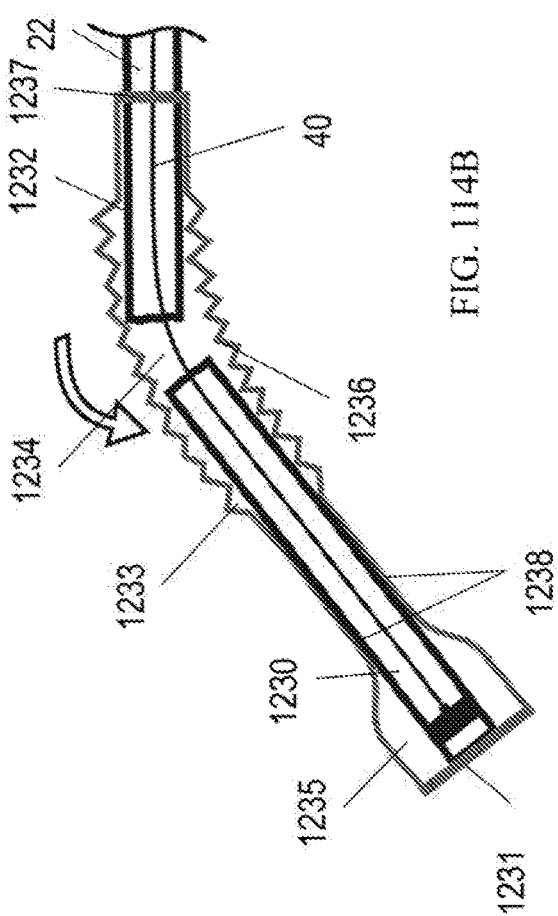
Figure 114B:
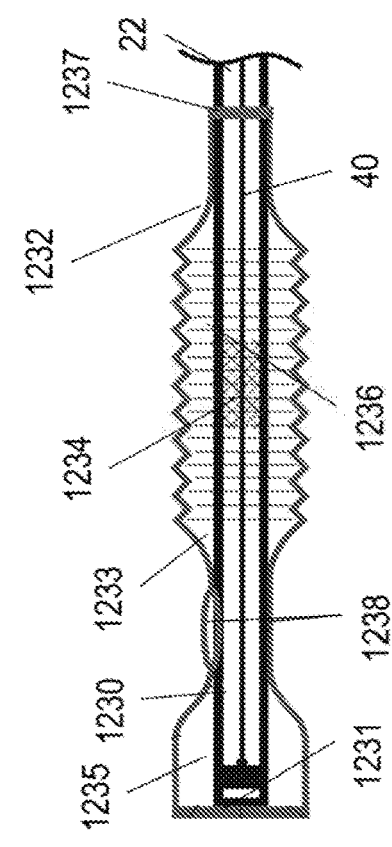

FIGS. 114A-114B illustrate another embodiment of the disengagement tool (1235) also having a cavity, a proximal stop and a distal opening. As shown in the FIG. 114A, the disengagement tool (1235) has one or more user-graspable portion (1238). For example, as shown in FIG. 114A, the graspable portion (1238) includes a recessed geometry configured to be grasped by fingers. Graspable portion (1238) has an inner diameter and inner surface configured to engage the outer surface of the implant pusher shaft (1232). Disengagement tool (1235) also has one or more stretchable portions (1238), such as a portion of concertinaed sides to allow for expansion and contraction, or a bellows construction as shown in the FIGS. 114A and 114B. In some embodiments, the graspable portion (1238) includes one or more holes to allow an opening of sufficient size for the user to make direct, tactile contact with implant pusher shaft (1232). In one embodiment, when the proximal portion (1230) of the implant pusher shaft (1232) sufficiently advances into disengagement tool (1235) to engage the proximal stop (1231) of the tool, the weakened location (1234) of the implant pusher shaft (1232) is positioned against the flexible portion (1236) of the disengagement tool (1235). Force applied by a clinician to disengagement tool (1235) causes implant pusher shaft (1232) to circumferentially fracture at its weakened location (1234). This flexible disengagement tool (1235) allows implant pusher shaft (1232) to break without exposing the clinician to any fracture.

Figure 115A:
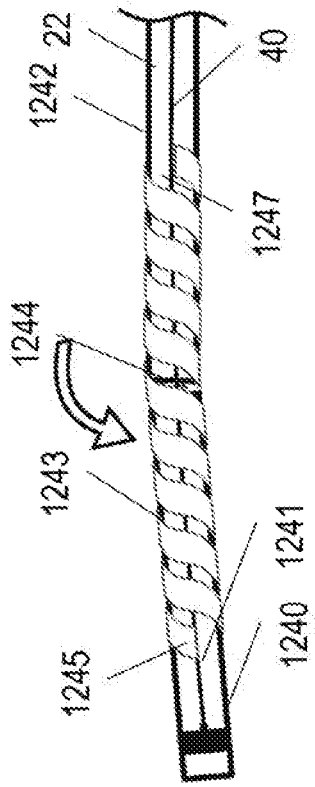
Figure 115B:
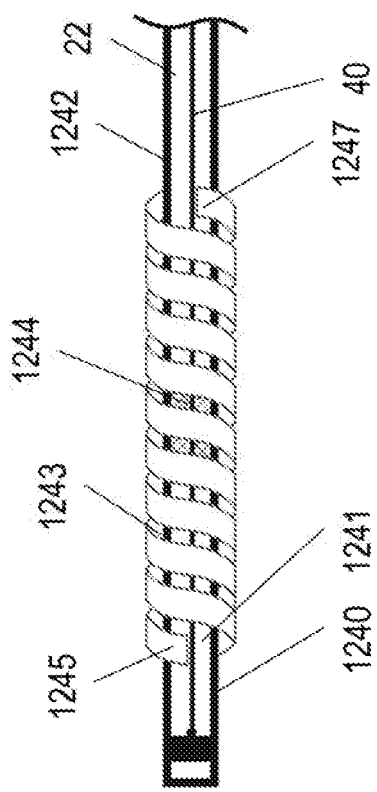

FIGS. 115A-115B illustrate another embodiment of the disengagement tool (1245) in the configuration of an expandable band with a center lumen (1243), a proximal opening (1241) and a distal opening (1247). As shown in FIG. 115A, the expandable band (1245) could be a helical coil. In one embodiment, the coil (1245) could be constructed with ABS, PVC, urethane, PEBAX, or other one or more semi-transparent and/or transparent materials, to allow visualization to the implant pusher shaft (1242). Coil (1245) could be made of material such as nylon, urethane, ABS, or PVC, urethane, silicone, or low durometer PEBAX, and others known in the field. In one embodiment, the coil (1245) has a radially expanded state, configured to slide over the proximal portion (1240) of the implant pusher shaft (1242), and covers the weakened location (1244). Force applied by a clinician to the coil and its covered weakened location (1244), causes implant pusher shaft (1242) to circumferentially fracture at its weakened location (1244). This coil (1245) allows implant pusher shaft (1242) to break without exposing the clinician to any fracture.

Figure 116A:
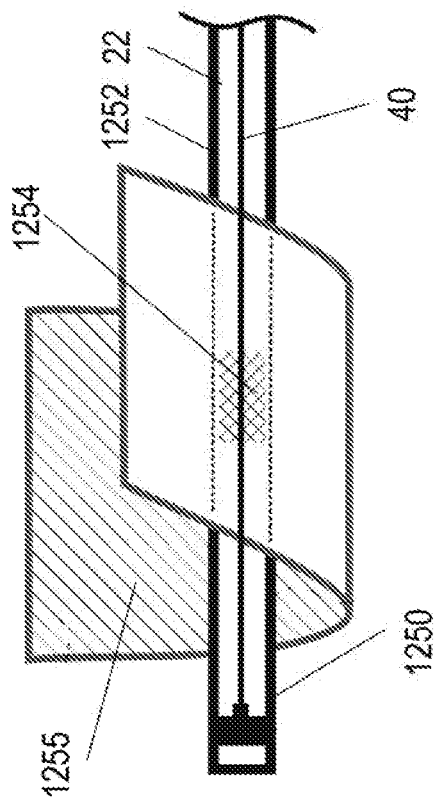
Figure 116B:
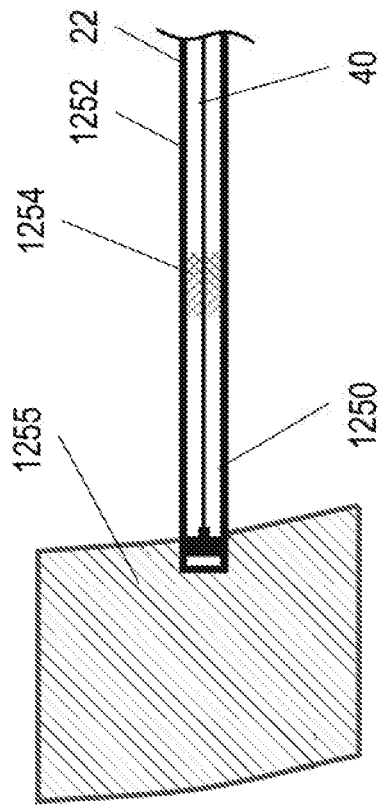

FIGS. 116A-116B illustrate another embodiment of the disengagement tool (1255) in the configuration of a flexible sheet. In one embodiment, the sheet (1255) could be made of one or more semi-transparent and/or transparent material to allow visualization of the implant pusher shaft (1252). In some embodiments, the sheet (1255) could be made of material such as urethane, low durometer PEBAX, silicone, latex, and others known to the field. In one embodiment, sheet (1255) could be folded and/or wrapped about the proximal end portion (1250), including the weakened location, of the implant pusher shaft (1552). Force applied by a clinician to the sheet (1255) and its covered weakened location (1254), causes implant pusher shaft (1552) to circumferentially fracture. This sheet (1255) allows implant pusher shaft (1552) to break without exposing the clinician to any fracture.

Figure 117B:
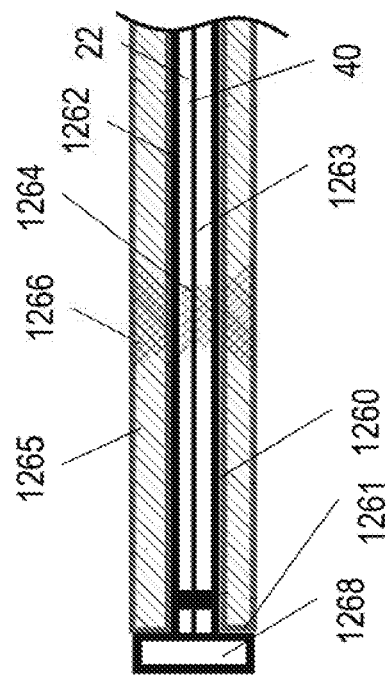
Figure 117A:
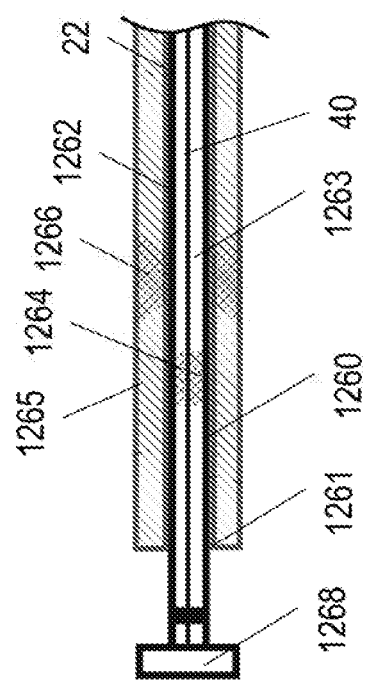
Figure 117C:
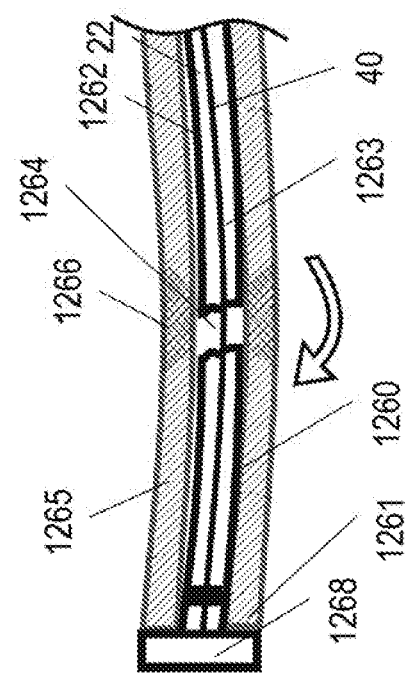

FIGS. 117A-117C illustrate another embodiment of the disengagement tool (1265) in the configuration of an elongated sheath. In one embodiment, the sheath (1265) could have a flexible proximal portion (1266) configured to allow twist, bend, and/or other deformation. In another embodiment, the sheath can have a flexible portion (1266) configured to be position over the weakened location (1264) of the implant pusher shaft (1262) as shown in FIG. 117B. In one embodiment, the proximal portion (1260) of the implant pusher shaft (1262) has an enlarged end stop (1268) to be positioned against the proximal end (1261) of the sheath (1265) as shown in FIG. 117B. In another embodiment, as the sheath (1265) is generally flexible throughout its entire length, the proximal portion (1260) of the implant pusher shaft (1262) does not have an enlarged end stop (1268). And a clinician could grab anywhere along the sheath (1265) to bend the implant pusher shaft (1262). In one embodiment, the sheath (1265) could be made of one or more semi-transparent and/or transparent material to allow visualization of the implant pusher shaft (20). In some embodiments, sheath (1265) could be made of material such as PE, PP, PTFE, and others known in the field. In one embodiment, when the sheath (1265) engages the proximal end portion (1260) of the implant pusher shaft (1262), the weakened location (1264) of the implant pusher shaft (1262) is positioned inside the sheath (1265). Force, such as the torsional force as shown by the arrow in FIG. 117C, applied by a clinician to the sheath (1265), causes the implant pusher shaft (1262) to circumferentially fracture. The sheath (1265) allows the implant pusher shaft (1262) to break without exposing the user to any fracture.

Figure 118A:
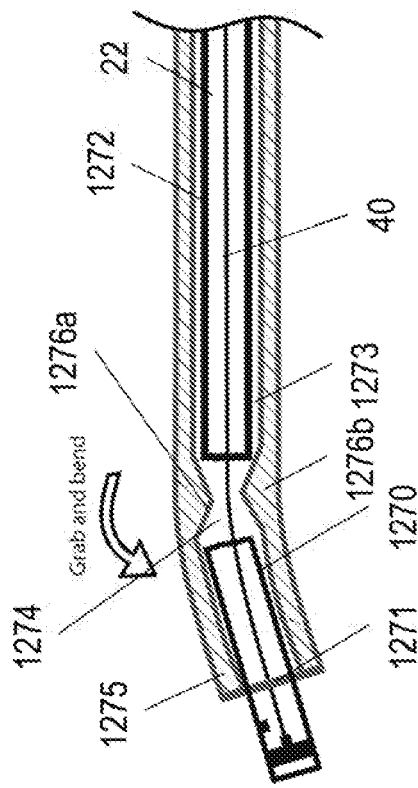
Figure 118B:
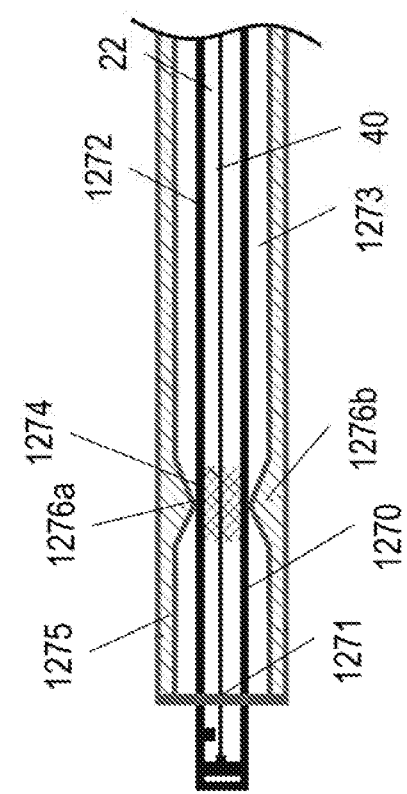

FIGS. 118A-118B illustrate another embodiment of the disengagement tool (1275) in the configuration of a flexible sheath. In one embodiment, the sheath (1275) could be made of one or more semi-transparent and/or transparent material to allow visualization of the implant pusher shaft (1272). In some embodiments, sheath (1275) could be made of material such as PE, PP, PTFE, and others known in the field. In one embodiment, sheath (1275) has two inwardly facing projections (1276a, 1276b) configured to engage the outer surface of the implant pusher shaft (1272). In one embodiment, when the sheath (1275) engages the proximal portion (1270) of the implant pusher shaft (1272), the weakened location (1274) of the implant pusher shaft (1272) is positioned inside the sheath (1275) against the projections (1276a, 1276b). Force, such as the torsional force as shown by the arrow in FIG. 118B, applied by a clinician to the sheath (1275), causes the implant pusher shaft (1272) to circumferentially fracture, via resultant force applied by projections (1276a, 1276b). The sheath (1275) allows the implant pusher shaft (1272) to break without exposing the user to any fracture.

According to some embodiment of the present teaching, for embodiments where the implant release control mechanism is configured to break apart from the implant pusher shaft in order to actuate implant release, an indicator could be incorporated to the exterior surface of the proximal end of the delivery system. This gives a clinician an accurate spot to grab. This would ease the breaking mechanism and result to a more reliable detachment.

Figure 119A:
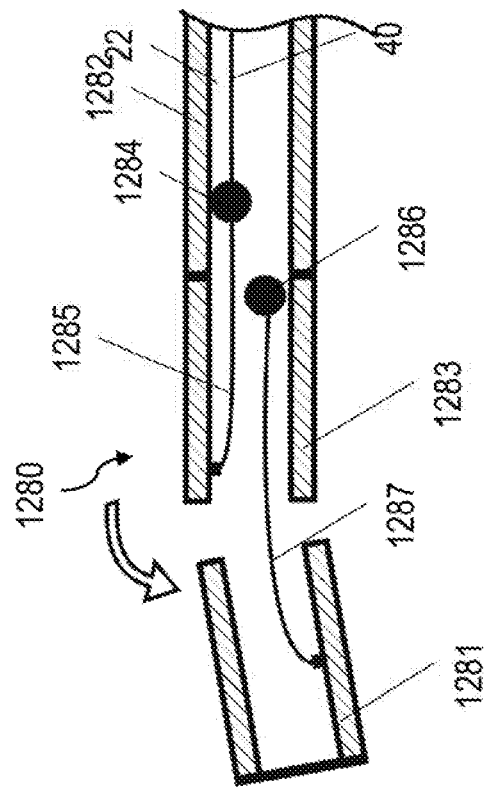
Figure 119B:
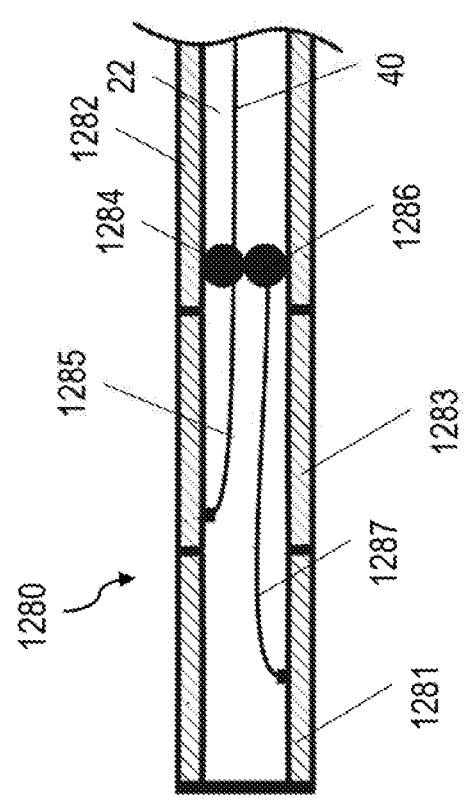

FIGS. 119A-119B illustrate another embodiment of the implant release control mechanism (1280). As shown in FIG. 119A, the implant release control mechanism (1280) has two shaft extensions (1281, 1283). In some embodiments, a distal shaft (1283) extension is positioned proximal to the implant pusher shaft (1282), and a proximal shaft extension (1281) is positioned proximal to the distal shaft extension (1283). A stopping member (1284, 1286) fixed to each shaft extension via a filament (1285, 1287). In one embodiment, the stopping member (1284, 1286) has a ball shape such as shown in FIG. 119A, and the filament (1285, 1287) is fixed to the inner lumen of shaft extension (1281, 1283) via thermal, chemical, and other mechanism known in the field. The proximal end of the engagement wire (40) fixedly joins the stopping member (1284) of the distal shaft extension (1283). FIG. 119A shows an embodiment of the implant delivery and deployment, where the distal shaft extension (1283) joins the proximal end of the implant pusher shaft (1282), the distal shaft extension (1283) joins the proximal end of the proximal shaft extension (1281), the stopping member (1284) of the distal shaft extension (1283) frictionally engages the stopping member (1286) of the proximal shaft extension (1281). To retract the engagement wire (40), a clinician detaches the proximal shaft extension (1281), causes the ball (1286) to disengage from ball (1284). Subsequently, a clinician detaches distal shaft extension (1283) from the implant pusher shaft (1282), allows retraction of distal shaft extension (1283). Retraction of the distal shaft extension (1283) then leads to a retraction of the engagement wire (40).

FIGS. 120A-120B illustrate another embodiment of the implant release control mechanism (1290). As shown in FIG. 120A, the implant release control mechanism (1290) has an elongated body (1296) an inner lumen (1293) with a coil (1295) partially fit inside the lumen (1293). The proximal end of the engagement wire (40) extends proximally through an opening (1297) of at the proximal end (1291) of the implant release control mechanism (1295) and further extends proximally outside of the body. The proximal end (1291) of the coil (1295) fixedly attaches to the proximal end (1291) of the inner lumen (1293) of the implant release control mechanism (1290). The coil (1295) has a tensioned state and a relaxed state. In its tensioned state, the coil (1295) elongates in length and narrows in diameter and configured to trap the proximal end of the engagement wire (40) as shown in FIG. 120A. In its relaxed state, the coil (1295) shortens in length and enlarges in diameter and therefore releases the proximal end of the engagement wire (40) as shown in FIG. 120B. In one embodiment, the elongated body (1296) of the implant release control mechanism (1290) is configured to frictionally engage the proximal end portion of the implant pusher shaft lumen (22). During implant delivery and deployment, the coil (1295) in its tensioned state, traps the proximal end of the engagement wire (40). At this state, the engagement wire (40) is trapped by the coil (1295) of the implant release control mechanism (1290) thereby prevented to either advance distally or retract proximally. To release the implant, the clinician pushes the implant release control mechanism (1290) distally, allowing the coil (1295) to relax, and free the engagement wire (40). At this point, a clinician can advance or retract the engagement wire (40) in order to release the implant.

According to some embodiments of the present teaching, the implant release control mechanism is actuated manually by a clinician. In another embodiment, the implant release is also facilitated with the assistance of vibrational energy, fatigue of a component, light (e.g. via one or more optical fibers); tension; compression; torsion; torque; heating or cooling (e.g. a temperature change for phase transformation or for thermal expansion or contraction); injection of a fluid or solid, electrical induced force; magnetics; a piezo electric component; a piezo resistive component; a biochemical reaction; a hydroactive component; a bioactive component; and/or a chemical reaction.

According to one embodiment, the exemplary implant-delivery system assembly could also include a sensor, a transducer, such as a wire, an optical fiber, a fluid delivery tube, a mechanical linkage that is operatively attached to the proximal end of the delivery system (10). In one embodiment, the sensor could be a physiologic sensor such as a blood sensor or a blood gas sensor, an electrical sensor such as a voltage sensor or a current sensor, a magnetic sensor such as a hall effect sensor, a mechanical sensor such as a strain gauge, an accelerometer or a flow sensor such as an ultrasonic flow sensor, a chemical sensor, and combinations of one or more of these. In another embodiment, the transducer can include an electrode that receives electrical energy, and distributes the electrical energy to tissue (e.g. based on the size of the electrode). In some configurations, a transducer converts an electrical signal into any output, such as light (e.g. a transducer comprising a light emitting diode or light bulb), sound (e.g. a transducer comprising a piezo crystal configured to deliver ultrasound energy), pressure, heat energy, cryogenic energy, chemical energy; mechanical energy (e.g. a transducer comprising a motor or a solenoid), magnetic energy, and/or a different electrical signal (e.g. a Bluetooth or other wireless communication element). In another configurations, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one or more of these.

Although not specifically described in above description, one skilled in the art should understand that additional access devices could also be used during a treatment procedure. For example, a vascular introducer sheath, such as an introducer sheath comprising high-density polyethylene (HDPE) and/or polypropylene can be used for creating a conduit for advancing the delivery system (10) and coil implant (80) assembly to a treatment location. Access devices can also include one or more standard guide catheters, interventional guidewires, and/or microcatheters. A delivery and deployment describe above, although what has been described herein is a coil implant (80), one skilled in the art should understand that the inventive principle disclosed herein could also apply to other medical implant such as a vaso-occlusive device, a stent and another drug delivery implant.

Although most implant release control mechanism disclosed above are configured to allow a clinician retracting engagement wire proximally, one skilled in the art should understand that exemplary embodiments disclosed with reference to FIGS. 60, 61, 62, 63, 65, 67, 68, 69, 70, 71, 72, 73, 75, and 76 could be adopted directly or with some modification to advance the engagement wire) in order to release the implant such as those illustrated in FIGS. 8, 18, 21, 22, 24, 25, 27, 32, and 34.

Although not specifically described in above disclosure, one skilled in the art should understand that a clinician may also employ other tools during a treatment procedure. For example, imaging devices such as fluoroscope; X-ray; CT scanner; MRI; ultrasound imager; and combinations of these could be used during delivery and positioning. In another embodiment, one or more radioopaque markers are used to aid visualization. Such marker could be incorporated either on the medical implant or the delivery system. Without attempting to limit to any particular function, these radioopaque markers can be visualized by using radiographic imaging equipment such as X-ray, magnetic resonance, ultrasound or other imaging techniques. Marker as disclosed herein can be applied to any part of a device or a delivery system of the present teachings. A radioopaque marker can be sewed, adhered, swaged riveted, otherwise placed, and secured in or on the device. The radioopaque marker may be made of tantalum, tungsten, platinum, irridium, gold, or alloys of these materials or other materials that are known to those skilled in the art. The radioopaque marker can also be made of numerous paramagnetic materials, including one or more elements with atomic numbers 21-29, 42, 44, and 58-70, such as chromium (III), manganese (II), iron (III), iron (II), cobalt (II), copper (II), nickel (II), praesodymium (III), neodymium (III), samarium (III), ytterbium (III), gadolinium (III), terbium (III), dysprosium (III), holmium (III) and erbium (III), or other MR visible materials that are known to those skilled in the arts.

One skilled in the art should understand, although most exemplary embodiments described above refers to an embolic coil implant, exemplary embodiments for implant-delivery system attachment embodiments and for the implant release control mechanism could be used with other implants such as other vaso-occlusive devices, stents, and etc. In some embodiments, exemplary embodiment for delivery system is constructed and arranged to precisely deliver an implant into an aneurysm, such as a brain aneurysm. In another embodiments, the exemplary embodiment for delivery system is arranged to precisely delivery an implant into a blood vessel such as a blood vessel of the brain, a patent blood vessel, or other locations.

The foregoing description and accompanying drawings set forth a number of examples of representative embodiments at the present time. Various modifications and alternative designs will become apparent to those skilled in the art in light of the foregoing teachings without departing from the spirit hereof, or exceeding the scope hereof, which is indicated by the following claims rather than by the foregoing description. All changes and variations that fall within the meaning and range of equivalency of the claims are to be embraced within their scope.

We claim:

1. A medical system for delivering and deploying an implant into a patient, the medical system comprising:
   a medical implant having a proximal engagement loop;
   an implant delivery system having an implant pusher shaft and an engagement wire;
   wherein the implant pusher shaft comprises an elongated lumen with a proximal end, a distal end, and an interface joining the distal end, and wherein the interface comprises two fingers joining by a cross pin;
   wherein the engagement wire comprises an elongated body with a proximal end and a distal end, and is configured to slidably dispose within the longitudinal lumen of the implant pusher shaft;
   wherein the medical system has a first configuration where a portion of the engagement loop extends proximally beyond the cross pin at its first side, and the proximal end of the engagement wire extends distally first through the engagement loop and then further distally beyond the cross pin at its second side, and the cross pin is pushing onto the proximal end of the medical implant.

2. The medical system of claim 1, wherein the medical system has a second configuration where the proximal end of the engagement wire extends proximally away from the cross pin and disengages the medical implant.

3. The medical system of claim 1, wherein in the first configuration, a portion of the engagement loop extends proximally beyond the cross pin at its first side, and the proximal end of the engagement wire extends distally first through the engagement loop and then further distally beyond the cross pin at its second side.

4. The medical system of claim 1, wherein the implant delivery system further comprises an implant release control mechanism fixedly joining the proximal end of the engagement wire.

5. The medical system of claim 4, wherein in the first configuration, the implant release control mechanism attaches the proximal end of the implant pusher shaft.

6. The medical system of claim 4, wherein in the second configuration, the implant release control mechanism disconnects the proximal end of the implant pusher shaft.

7. A medical system for delivery and deploying an implant into a patient, the medical system comprising:
   a medical implant having a proximal engagement loop;
   an implant delivery system having an implant pusher shaft and an engagement wire;
   wherein the implant pusher shaft comprises an elongated lumen with a proximal end, a distal end, and an interface joining the distal end, and wherein the interface comprises two fingers joining by a cross pin;
   wherein the engagement wire comprises an elongated body with a proximal end and a distal end, and is configured to slidably dispose within the longitudinal lumen of the implant pusher shaft;
   wherein the medical system has a first configuration where a portion of the engagement loop extends to a location proximal to the cross pin, and the engagement wire interacts with the cross pin and thereby prevents unintended distal movement of the portion of the engagement loop, and the cross pin is pushing onto the proximal end of the medical implant during implant delivery.

8. The medical system of claim 7, wherein the engagement wire interacts with the cross pin by extending through the engagement loop of the medical implant and further distally so that the distal end of the engagement wire is distal to the cross pin.

9. The medical system of claim 7, wherein the engagement wire interacts with the cross pin by extending through the engagement loop of the implant and adjoins a surface of the cross pin.

10. The medical system of claim 1, wherein the implant delivery system further comprises an implant release control mechanism fixedly joining the proximal end of the engagement wire.

11. The medical system of claim 10, wherein in the first configuration, the implant release control mechanism attaches the proximal end of the implant pusher shaft.

12. The medical system of claim 10, wherein in the second configuration, the implant release control mechanism disconnects the proximal end of the implant pusher shaft.

13. The medical system of claim 10, wherein as the medical system in its first configuration, the distal end of the engagement wire is at its most distal position.

14. The medical system of claim 10, wherein as the medical system transitioning from the first configuration to the second configuration, the distal end of the engagement wire retracts proximally.

\* \* \* \* \*